United States Patent
Huang et al.

(10) Patent No.: US 8,426,595 B2
(45) Date of Patent: Apr. 23, 2013

(54) GAMMA SECRETASE MODULATORS

(76) Inventors: Xianhai Huang, Warren, NJ (US); Anandan Palani, Bridgewater, NJ (US); Robert G. Aslanian, Rockaway, NJ (US)

(*) Notice: Subject to any disclaimer, the term of this patent is extended or adjusted under 35 U.S.C. 154(b) by 212 days.

(21) Appl. No.: 12/747,011

(22) PCT Filed: Dec. 9, 2008

(86) PCT No.: PCT/US2008/086058
§ 371 (c)(1),
(2), (4) Date: Jul. 29, 2010

(87) PCT Pub. No.: WO2009/076352
PCT Pub. Date: Jun. 18, 2009

(65) Prior Publication Data
US 2010/0297128 A1    Nov. 25, 2010

Related U.S. Application Data

(60) Provisional application No. 61/012,857, filed on Dec. 11, 2007.

(51) Int. Cl.
*C07D 498/02* (2006.01)
*A61K 31/44* (2006.01)

(52) U.S. Cl.
USPC .................................. 546/118; 514/303

(58) Field of Classification Search .................. None
See application file for complete search history.

(56) References Cited

U.S. PATENT DOCUMENTS

| | | | |
|---|---|---|---|
| 5,883,096 A | 3/1999 | Lowe et al. |
| 5,889,006 A | 3/1999 | Lowe et al. |
| 5,935,958 A | 8/1999 | Kozlowski et al. |
| 5,952,349 A | 9/1999 | Asberom et al. |
| 5,977,138 A | 11/1999 | Wang et al. |
| 6,037,352 A | 3/2000 | Lowe et al. |
| 6,043,255 A | 3/2000 | Lowe et al. |
| 6,066,636 A | 5/2000 | Kozlowski et al. |
| 6,294,544 B1 | 9/2001 | Araie et al. |
| 6,458,812 B1 | 10/2002 | McKittrick et al. |
| 2005/0042284 A1 | 2/2005 | Hobden et al. |
| 2005/0043290 A1 | 2/2005 | Cumming et al. |
| 2005/0119227 A1 | 6/2005 | Cumming et al. |
| 2006/0004013 A1 | 1/2006 | Kimura et al. |
| 2006/0040948 A1 | 2/2006 | Stamford et al. |
| 2006/0040994 A1 | 2/2006 | Huang et al. |
| 2006/0111370 A1 | 5/2006 | Zhu et al. |
| 2006/0281729 A1 | 12/2006 | Iserloh et al. |
| 2006/0281730 A1 | 12/2006 | Zhu et al. |
| 2006/0287294 A1 | 12/2006 | Zhu et al. |
| 2007/0010667 A1 | 1/2007 | McKittrick et al. |
| 2007/0060575 A1 | 3/2007 | Zhu et al. |
| 2007/0072852 A1 | 3/2007 | Zhu et al. |
| 2007/0099875 A1 | 5/2007 | Zhu et al. |
| 2007/0099898 A1 | 5/2007 | Zhu et al. |
| 2007/0117798 A1 | 5/2007 | Kimura et al. |
| 2007/0117839 A1 | 5/2007 | Kimura et al. |

FOREIGN PATENT DOCUMENTS

| | | |
|---|---|---|
| WO | 03/002122 A | 1/2003 |
| WO | WO 03/002122 | 1/2003 |
| WO | 03031412 A1 | 4/2003 |
| WO | 03042214 A | 5/2003 |
| WO | WO 03/042214 | 5/2003 |
| WO | 2004071431 A2 | 8/2004 |
| WO | 2004110350 A2 | 12/2004 |
| WO | 2005014540 A1 | 2/2005 |
| WO | 2005016876 A2 | 2/2005 |
| WO | 2005058311 A1 | 6/2005 |
| WO | 2005110422 A2 | 11/2005 |
| WO | 2006001877 A2 | 1/2006 |
| WO | 2006014762 A1 | 2/2006 |
| WO | 2006014944 A1 | 2/2006 |
| WO | 2006045554 A1 | 5/2006 |
| WO | 2006065277 A2 | 6/2006 |
| WO | 2006138192 A1 | 12/2006 |
| WO | 2006138195 A1 | 12/2006 |
| WO | 2006138217 A1 | 12/2006 |
| WO | 2006138230 A2 | 12/2006 |
| WO | 2006138264 A2 | 12/2006 |
| WO | 2006138265 A2 | 12/2006 |
| WO | 2006138266 A2 | 12/2006 |
| WO | 2007050721 A2 | 5/2007 |
| WO | 2007053506 A1 | 5/2007 |
| WO | 2007120454 A | 10/2007 |
| WO | WO 2007/120454 | 10/2007 |
| WO | WO 2007120454 A1 * | 10/2007 |

OTHER PUBLICATIONS

International Search Report for PCT/US2008/086058 mailed on Mar. 5, 2009.
Written Opinion for International Application No. PCT/US2008/086058 mailed Mar. 5, 2009.
Berge, et al., "Pharmaceutical Salts," Journal of Pharmaceutical Sciences, vol. 66, No. 1, pp. 1-19, 1977.

(Continued)

*Primary Examiner* — Janet Andres
*Assistant Examiner* — Heidi Reese
(74) *Attorney, Agent, or Firm* — Susan L. Hess; Henry Jeanette; Gerard M. Devlin

(57) ABSTRACT

This invention provides novel compounds that are modulators of gamma secretase. The compounds have the formula [Chemical formula should be inserted here as it appears on abstract in electronic form.] Also disclosed are methods of modulating gamma secretase activity and methods of treating Alzheimer's disease using the compounds of formula (I).

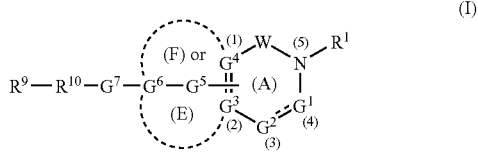

8 Claims, No Drawings

OTHER PUBLICATIONS

Bingham, et al., "Over one hundred solvates of sulfathiazole," Chem. Comm., pp. 603-604, 2001.

Caira, et al., "Preparation and Crystal Characterization of a Polymorph, a Monohydrate, and an Ethyl Acetate Solvate of the Antifungal Fluconazole," J. Pharmaceutical Sci., vol. 93, vol. 3, pp. 601-611, 2004.

Forman, et al., Differential Effects of the Swedish Mutant Amyloid Precursor Protein on β-Amyloid Accumulation and Secretion in Neurons and Nonneuronal Cells., The Journal of Biological Chemistry, vol. 272, No. 51, pp. 32247-32253, 1997.

Frangione, et al., "Familial cerebral amyloid angiopathy related to stroke and dementia," Amyloid: J. Protein Folding Disord. 8,Suppl. 1, pp. 36-42, 2001.

Getchell, et al. "3-Nitrotyrosine immunoreactivity in olfactory receptor neurons of patients with Alzhemier's disease: implications for impaired odor sensitivity," Neurobiology of Aging, vol. 24, pp. 663-673, 2003.

Glenner, et al., "Alzheimer's Disease: Initial Report of the Purification and Characterization of a Novel Cerebrovascular Amyloid Protein," Biochem and Biophys. Res. Comm., vol. 120, No. 3, pp. 885-890, 1984.

Gong, et al., "Alzheimer's disease-affected brain: Presence of oligonumeric Aβ ligands (ADDLs) suggests a molecular basis for reversible memory loss," PNAS, vol. 100, No. 18, pp. 10417-10422, 2003.

Gould, "Salt selection for basic drugs," Interrnational Journal of Pharmaceutics, vol. 33, pp. 201-217, 1986.

Gouras, et al., Intraneuronal Aβ Accumulation in Human Brain, American Journal of Pathology, vol. 156, No. 1, pp. 15-20, 2000.

Guo, et al., "Targeting amyloid-β in glaucome treatment," PNAS, vol. 104, No. 33, pp. 13444-13449, 2007.

Hock, et al., "Antibodies against β-Amyloid Slow Cognitive Decline in Alzheimer's Disease," Neuron, vol. 38, pp. 547-554, 2003.

Jarrett, et al., "The Carboxy Terminus of the β Amyloid Protein Is Critical for the Seeding of Amyloid Formation: Implications for the Pathogenesis of Alzheimer's Disease," Biochemistry, vol. 32, No. 18, pp. 4693-4697, 1993.

Lambert, et al., "Diffusible, nonfibrillar ligands derived from Aβ1-42 are potent central nervous system neurotoxins," PNAS Sci. USA, vol. 95, pp. 6448-6453, 1998.

Masters, et al., "Amyloid plaque core protein in Alzheimer's disease and Down syndrome," PNAS Sci USA, vol. 82, pp. 4245-4249, 1985.

Scheuner, et al., "Secreted Amyloid β-protein simila to that in the senile plaques of Alzhemier's disease is increased in vivo by the presenilin 1 and 2 and APP mutations linked to familial Alzheimer's disease," Nature Medicine, vol. 2, No. 8, Aug. 1996.

Shearman, et al., "L-685,458, an Aspartyl Protease Transition State Mimic, Is a Potent Inhibitor of Amyloid β-Protein Precursor γ-Secretase Activity," Biochemistry, vol. 39, pp. 8698-8704, 2000.

von Tonder, et al., "Preparation and Physicochemical Characterization of 5 Niclosamide Solvates and 1 Hemisolvate," AAPS Pharm Sci Tech., vol. 5, No. 1, Article 12, 2004.

WO09076352 Search Report, 2009.

* cited by examiner

GAMMA SECRETASE MODULATORS

CROSS REFERENCE TO RELATED APPLICATION

This application is entered into national staqe examination under 37 U.S.C. 371 and stems from international patent application No. PCT/US2008/086058 filed on Dec. 9, 2008.

REFERENCE TO RELATED APPLICATION

This application claims the benefit of U.S. Provisional Application Ser. No. 61/012,857 filed Dec. 11, 2007.

FIELD OF THE INVENTION

The present invention relates to certain heterocyclic compounds useful as gamma secretase modulators (including inhibitors, antagonists and the like), pharmaceutical compositions containing the compounds, and methods of treatment using the compounds and compositions to treat various diseases including central nervous system disorders such as, for example, neurodegenerative diseases such as Alzheimer's disease and other diseases relating to the deposition of amyloid protein. They are especially useful for reducing Amyloid beta (hereinafter referred to as Aβ) production which is effective in the treatment of diseases caused by Aβ such as, for example, Alzheimers and Down Syndrome.

BACKGROUND OF THE INVENTION

Alzheimer's disease is a disease characterized by degeneration and loss of neurons and also by the formation of senile plaques and neurofibrillary change. Presently, treatment of Alzheimer's disease is limited to symptomatic therapies with a symptom-improving agent represented by an acetylcholinesterase inhibitor, and the basic remedy which prevents progress of the disease has not been developed. A method of controlling the cause of onset of pathologic conditions needs to be developed for creation of the basic remedy of Alzheimer's disease.

Aβ protein, which is a metabolite of amyloid precursor protein (hereinafter referred to as APP), is considered to be greatly involved in degeneration and loss of neurons as well as onset of demential conditions (for example, see Klein W L, et al *Proceeding National Academy of Science USA*, Sep. 2, 2003, 100(18), p. 10417-22, suggest a molecular basis for reversible memory loss.

Nitsch R M, and 16 others, *Antibodies against β-amyloid slow cognitive decline in Alzheimer's disease*, Neuron, May 22, 2003, 38(4), p. 547-554) suggest that the main components of Aβ protein are Aβ40 consisting of 40 amino acids and Aβ42 having two additional amino acids at the C-terminal. The Aβ40 and Aβ42 tend to aggregate (for example, see Jarrell J T et al, *The carboxy terminus of the β amyloid protein is critical for the seeding of amyloid formation: implications for the pathogenesis of Alzheimer's disease*, Biochemistry, May 11, 1993, 32(18), p. 4693-4697) and constitute the main components of senile plaques (for example, (Glenner G G, et al, *Alzheimer's disease: initial report of the purification and characterization of a novel cerebrovascular amyloid protein*, Biochemical and Biophysical Research Communications, May 16, 1984, 120(3), p. 885-90. See also Masters C L, et al, *Amyloid plaque core protein in Alzheimer disease and Down syndrome*, Proceeding National Academy of Science USA, June 1985, 82(12), p. 4245-4249.).

Furthermore, it is known that mutations of APP and presenelin genes, which is are observed in familial Alzheimer's disease, increase production of Aβ40 and Aβ42 (for example, see Gouras G K, et al, *Intraneuronal Aβ142 accumulation in human brain*, American Journal of Pathology, January 2000, 156(1), p. 15-20. Also, see Scheuner I D, et al, Nature Medicine, August 1996, 2(8), p. 864-870; and Forman M S, et al, *Differential effects of the Swedish mutant amyloid precursor protein on β-amyloid accumulation and secretion in neurons and normeuronal cells*, Journal of Biological Chemistry, Dec. 19, 1997, 272(51), p. 32247-32253.). Therefore, compounds which reduce production of Aβ40 and Aβ42 are expected to be agents for controlling progress of Alzheimer's disease or for preventing the disease.

These Aβs are produced when APP is cleaved by beta secretase and subsequently cleaved by gamma secretase. In consideration of this, creation of inhibitors of γ-secretase and β-secretase has been attempted for the purpose of reducing production of Aβs. Many of these known secretase inhibitors are peptides or peptidomimetics such as L-685,458. L-685, 458, an aspartyl protease transition state mimic, is a potent inhibitor of γ-secretase activity, Biochemistry, Aug. 1, 2000, 39(30), p, 8698-8704).

Also of interest in connection with the present invention are: US 2007/0117798 (Eisai, published May 24, 2007); US 2007/0117839 (Eisai, published May 24, 2007); US 2006/0004013 (Eisai, published Jan. 5, 2006); WO 2005/110422 (Boehringer Ingeiheim, published Nov. 24, 2005); WO 2006/045554 (Cellzone AG, published May 4, 2006); WO 2004/110350 (Neurogenetics, published Dec. 23, 2004); WO 2004/071431 (Myriad Genetics, published Aug. 26, 2004); US 200510042284 (Myriad Genetics, published Feb. 23, 2005) and WO 2006/001877 (Myriad Genetics, published Jan. 5, 2006).

There is a need for new compounds, formulations, treatments and therapies to treat diseases and disorders associated with Aβ. It is, therefore, an object of this invention to provide compounds useful in the treatment or prevention or amelioration of such diseases and disorders.

SUMMARY OF THE INVENTION

In its many embodiments, the present invention provides a novel class of compounds as gamma secretase modulators (including inhibitors, antagonists and the like), methods of preparing such compounds, pharmaceutical compositions comprising one or more such compounds, methods of preparing pharmaceutical formulations comprising one or more such compounds, and methods of treatment, prevention, inhibition or amelioration of one or more diseases associated with the Aβ using such compounds or pharmaceutical compositions.

This invention provides novel compounds, that are gamma secretase modulators, of the formula:

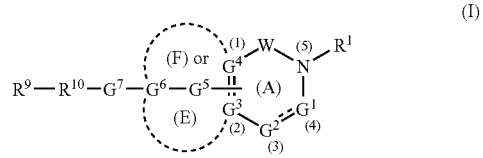

(I)

or a pharmaceutically acceptable salt, ester, or solvate thereof, wherein:

(1) Ring (E) comprises the moiety

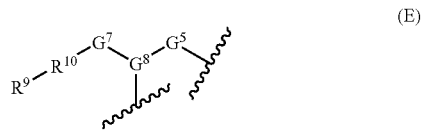

(E)

wherein $G^5$ is bound to $G^4$, and the rest of Ring (E) is formed between $G^6$ and $G^3$, and (2) Ring (F) comprises the moiety

(F)

wherein $G^5$ is bound to $G^3$, and the rest of Ring (F) is formed between $G^6$ and $G^4$, and (3) $G^1$, $G^2$, $G^3$, G, W, $R^1$, Ring (A), Ring (E), Ring (F), $G^5$, $G^6$, $G^7$, $R^9$, and $R^{10}$ are independently selected and are as defined below for formulas (IA) and (IB).

Thus, this invention provides novel compounds of formula (I)

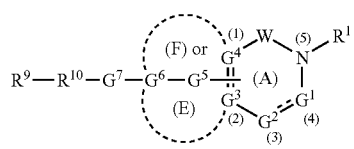

(I)

selected from the group consisting of:

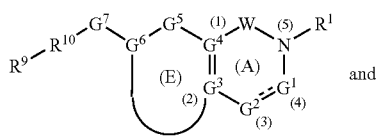

(IA)

and

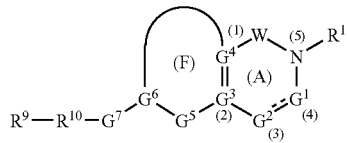

(IB)

or a pharmaceutically acceptable salt, ester, or solvate thereof, wherein all substituents are defined below.

This invention also provides compounds of formula (I).

This invention also provides compounds of formula (I) in pure and isolated form.

This invention also provides compounds of formula (I) selected from the group consisting of: compounds of formulas IA, IB, IA.1, IB.1, 43A to 54A, 43 to 54, 85.1, 88.1, 91.1, and 100 to 124.

This invention also provides compounds of formula (I) selected from the group consisting of: compounds of formulas 43A to 54A, 43 to 54, 85.1, 88.1, 91.1, and 100 to 124.

This invention also provides compounds of formula (I) selected from the group consisting of: compounds of formulas IA, IB, IA.1, and IB.1.

This invention also provides compounds of formula (I) selected from the group consisting of: compounds of formulas 43A to 54A.

This invention also provides compounds of formula (I) selected from the group consisting of: compounds of formulas 43 to 54.

This invention also provides compounds of formula (I) selected from the group consisting of: compounds of formulas 85.1, 88.1, 91.1, and 100 to 124.

This invention also provides pharmaceutical compositions comprising an effective amount of one or more (e.g., one) compounds of formula (I), or a pharmaceutically acceptable salt, ester or solvate thereof, and a pharmaceutically acceptable carrier.

This invention also provides pharmaceutical compositions comprising an effective amount of one or more (e.g., one) compounds of formula (I), or a pharmaceutically acceptable salt, ester or solvate thereof, and an effective amount of one or more (e.g., one) other pharmaceutically active ingredients (e.g., drugs), and a pharmaceutically acceptable carrier.

The compounds of formula (I) can be useful as gamma secretase modulators and can be useful in the treatment and prevention of diseases such as, for example, central nervous system disorders such as Alzheimers disease and Downs Syndrome.

Thus, this invention also provides methods for: (1) method for modulating (including inhibiting, antagonizing and the like) gamma-secretase; (2) treating one or more neurodegenerative diseases; (3) inhibiting the deposition of amyloid protein (e.g., amyloid beta protein) in, on or around neurological tissue (e.g., the brain); (4) Alzheimer's disease; and (5) treating Downs syndrome; wherein each method comprises administering an effective amount of one or more (e.g., one) compounds of formula (I) to a patient in need of such treatment.

This invention also provides combination therapies for (1) modulating gamma-secretase, or (2) treating one or more neurodegenerative diseases, or (3) inhibiting the deposition of amyloid protein (e.g., amyloid beta protein) in, on or around neurological tissue (e.g., the brain), or (4) treating Alzheimer's disease. The combination therapies are directed to methods comprising the administration of an effective amount of one or more (e.g. one) compounds of formula (I) and the administration of an effective amount of one or more (e.g., one) other pharmaceutical active ingredients (e.g., drugs).

This invention also provides methods for: (1) treating mild cognitive impairment; (2) treating glaucoma; (3) treating cerebral amyloid angiopathy; (4) treating stroke; (5) treating dementia; (6) treating microgliosis; (7) treating brain inflammation; and (8) treating olfactory function loss; wherein each method comprises administering an effective amount of one or more (e.g., one) compounds of formula (I) to a patient in need of such treatment.

This invention also provides a kit comprising, in separate containers, in a single package, pharmaceutical compositions for use in combination, wherein one container comprises an effective amount of a compound of formula (I) in a pharmaceutically acceptable carrier, and another container (i.e., a second container) comprises an effective amount of another pharmaceutically active ingredient (as described below), the combined quantities of the compound of formula (I) and the other pharmaceutically active ingredient being effective to treat the diseases or conditions mentioned in any of the above methods.

This invention also provides any of the above mentioned methods, pharmaceutical compositions or kit wherein the compound of formula (I) is selected from the group consisting of: compounds of formulas IA, IB, IA.1, IB.1, 43A to 54A, 43 to 54, 85.1, 88.1, and 91.1.

This invention also provides any of the above mentioned methods, pharmaceutical compositions or kit wherein the compound of formula (I) is selected from the group consisting of: compounds 43A to 54A, 43 to 54, 85.1, 88.1, and 91.1.

This invention also provides any of the above mentioned methods, pharmaceutical compositions or kit wherein the compound of formula (I) is selected from the group consisting of: compounds IA, a IA.1, and IB.1.

This invention also provides any of the above mentioned methods, pharmaceutical compositions or kit wherein the compound of formula (I) is selected from the group consisting of: compounds 43A to 54A.

This invention also provides any of the above mentioned methods, pharmaceutical compositions or kit wherein the compound of formula (I) is selected from the group consisting of: compounds 43 to 54.

This invention also provides any of the above mentioned methods, pharmaceutical compositions or kit wherein the compound of formula (I) is selected from the group consisting of: compounds 85.1, 88.1, 91.1, and 100 to 124.

This invention is also directed to any of the embodiments described above wherein the compound of formula (I) is a compound of formula (IA).

This invention is also directed to any of the embodiments described above wherein the compound of formula (I) is a compound of formula (IB).

DETAILED DESCRIPTION OF THE INVENTION

This invention provides novel compounds, that are gamma secretase modulators, of the formula:

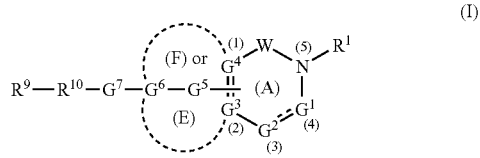
(I)

selected from the group consisting of compounds:

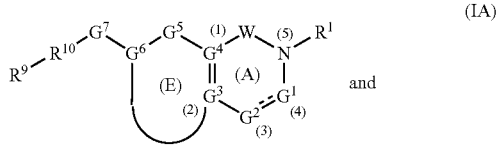
(IA)

and

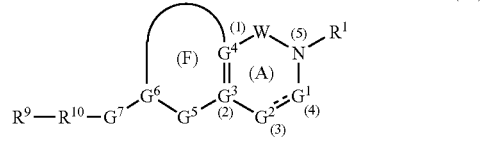
(IB)

or a pharmaceutically acceptable salt, ester, or solvate thereof, wherein:

$G^2$, $G^3$, $G^4$, W, $R^1$, Ring (A), Ring (E), Ring (F), $G^5$, $G^6$, $G^7$, $R^9$, and $R^{10}$ are independently selected;

letters (A), (E) and (F) in the formulas are reference letters to identify the rings;

the dotted line between $G^1$ and $G^2$ represents an optional bond;

the numbers (1), (2), (3), (4), and (5) are reference numbers to identify positions of the Ring (A); $G^4$ is at position (1), $G^3$ is at position (2), $G^2$ is at position (3), $G^1$ is at position (4) and the N is at position (5);

when $G^5$ is bound to $G^4$ (formula IA) then $G^4$ is a —C—, and when $G^5$ is bound to $G^3$ (formula IB) then $G^3$ is a —C—;

in said Ring (E): (a) $G^3$ is C (i.e., $G^3$ is —C($R^{21}$)$_q$— and q is 0), and $G^4$ is C (i.e., $G^4$ is —C($R^{21}$)$_q$— and q is 0), or (b) $G^3$ is N and $G^4$ is C and the double bond between $G^3$ and $G^4$ is tautomerized to Ring (E), in said Ring (F): (a) $G^3$ is C (i.e., $G^3$ is —C($R^{21}$)$_q$— and q is 0), and $G^4$ is C (i.e., $G^4$ is —C($R^{21}$)$_q$— and q is 0), or (b) $G^4$ is N and $G^3$ is C and the double bond between $G^3$ and $G^4$ is tautomerized to Ring (F), said Ring (E) or (F) is a 4 to 10 (and in one example 5 to 6) membered heteroaryl, aryl, cycioalkenyl, or heterocycloalkenyl ring;

when said Ring (E) or (F) is a heterocycloalkenyl ring or a heteroaryl ring, said Ring optionally comprises at least one (e.g., 1 to 4, 1 to 3, or 1 to 2, or 1) other heteroatom selected from the group consisting of: —N$R^2$—, —O—, —S—, —S(O)—, and —S(O)$_2$—;

said Ring (E) or (F) is optionally substituted with 1 to 6 independently selected $R^{21}$ substituents;

d is 0 or 1 (and those skilled in the art will appreciate that when d is 0 in the —N($R^2$)$_d$-moiety there is no substituent on the N, thus, the moiety —N($R^2$)$_d$— is —N= or —NH— when d is 0, i.e., when d is 0 in a moiety there is the appropriate number of H atoms on the N to fill the required valences);

m is 0 to 6;

n is 1 to 5;

p is 0 to 5;

q is 0, 1 or 2, and each q is independently selected (and those skilled in the art will appreciate that when q is 0 in the moiety —C($R^{21}$)$_q$ this means that there is no $R^{21}$ substituent on the carbon, and the —C($R^{21}$)$_q$ moiety is —CH= or —CH$_2$—, i.e., when q is 0 in a moiety there is the appropriate number of H atoms on the carbon to fill the required valences);

r is 1 to 3;

t is 1 or 2;

W is selected from the group consisting of: —C(O)—, —S(O)$_2$—, —S(O)—, and —C(=N$R^2$)— (and in one example W is —C(O)—);

$G^1$ is selected from the group consisting of: a direct bond, —O—, —S—, —C($R^{21}$)$_q$—, —N($R^2$)$_d$—, —C(O)—, S(O), S(O)$_2$, —C(N($R^2$)$_2$)— (wherein each $R^2$ is independently selected), and —C(=N$R^2$)—; and with the provisos that:

(1) when the optional bond between $G^1$ and $G^2$ is absent (i.e., there is a single bond between $G^1$ and $G^2$) then $G^1$ is not —C(N($R^2$)$_2$)—; and (2) when the optional bond between $G^1$ and $G^2$ is present (i.e., there is a double bond between $G^1$ and $G^2$) then:

(a) q for the —C($R^{21}$)$_q$ group is 0 or 1 (and when q is 0 then there is a H on the carbon), and (b) d for the —N($R^2$)$_d$— group is 0 (and there is no H on the N due to the double bond between $G^1$ and $G^2$ (i.e., between positions (3) and (4)); and (c) $G^1$ is not a direct bond, —O—, —S—, —C(O)—, —C(=N$R^2$)—, —S(O)$_2$—, or —S(O)—:

$G^2$ is selected from the group consisting of: a direct bond, —O—, —S—, —C($R^{21}$)$_q$, —N($R^2$)$_d$—, —C(O)—, S(O), S(O)$_2$, —C(N($R^2$)$_2$)— (wherein each $R^2$ is independently selected), and —C(=N$R^2$)—; and with the provisos that:

(1) when the optional bond between $G^1$ and $G^2$ is absent (i.e., there is a single bond between $G^1$ and $G^2$) then $G^2$ is not —C(N($R^2$)$_2$)—; and (2) when the optional bond between $G^1$ and $G^2$ is present (i.e., there is a double bond between $G^1$ and $G^2$), then:

(a) q for the —C($R^{21}$)$_q$ group is 0 or 1 (and when q is 0 then there is a H on the carbon), and (b) d for the —N($R^2$)$_d$— group is 0 (and there is no H on the N due to the double bond between positions (3) and (4)); and (c) $G^2$ is not a direct bond, —O—, —S—, —C(O)—, —C(=N$R^2$)—-, —S(O)$_2$—, or —S(O)—;

G$^5$ is selected from the group consisting of: direct bond, CH, —C(R$^{21}$)$_q$—, —N(R$^2$)$_d$—, —O—, —S—, —S(O)$_t$; —C(O)—, —(C=NR$^2$)—, —CHR$^3$—, C(R$^4$)$_2$, —CF$_2$—, —N(R$^2$)—, —CR$^4$(OH)—, —CR$^4$(OR$^4$)—, cycloalkyl, and heteracycloalkyl;

G$^6$ is selected from the group consisting of: C, CR$^3$, and N;

G$^7$ is selected from the group consisting of: a direct bond, —C(O)—, —(C=NR$^2$)—, —CHR$^3$—, C(R$^4$)$_2$, —CF$_2$—, —N(R$^2$)—, —O—, —S—, —S(O)$_t$, —CR$^4$(OH)—, —CR$^4$(OR$^4$)—, —C≡C—, alkynyl, —(CH$_2$)$_r$N(R$^2$)—, —(CHR$^4$)$_r$N(R$^2$)—, —(C(R$^4$)$_2$)$_r$N(R$^2$)—, —N(R$^2$)(CH$_2$)$_r$—, —N(R$^2$)(CHR$^4$)$_r$—N(R$^2$)(C(R$^4$)$_2$)$_r$—(CH$_2$)$_r$—O—, —(CHR$^4$)$_r$—O—, —(C(R$^4$)$_2$)$_r$—O—, —O—(CH$_2$)$_r$—, —O—(CHR$^4$)$_r$—, —O—(C(R$_4$)$_2$)$_r$—, —C(O)NR$^5$—, —O—C(O)—, —C(O)—O—, —O—C(O)—NR$^5$—, —NR$^5$C(O)—, —(CH$_2$)$_r$NR$^5$—C(O)—, —(CHR$^4$)$_r$NR$^5$—C(O)—, —(C(R$^4$)$_2$)$_r$NR$^5$—C(O)—, —C(O)NR$^5$(CH$_2$)$_r$—, —C(O)NR$^5$(CHR$^4$)$_r$—, —C(O)NR$^5$(C(R$^4$)$_2$)$_r$—, —NR$^5$S(O)$_t$—, —(CH$_2$)$_r$NR$^5$S(O)$_t$—, —(CHR$^4$)$_r$NR$^5$S(O)$_t$—, —(C(R$^4$)$_2$)$_r$NR$^5$S(O)$_t$—, —S(O)$_t$NR$^5$—, —S(O)$_t$NR$^5$(CH$_2$)$_r$—, —S(O)$_t$NR$^5$(CHR$^4$)$_r$—, —S(O)$_t$NR$^5$(C(R$^4$)$_2$)$_r$—, —NR$^5$—C(O)—O—, —NR$^5$—C(O)—NR$^5$—, —NR$^5$—S(O)$_t$—NR$^5$—, —NR$^5$—C(=NR$^2$)—NR$^5$—, —NR$^S$—C(=NR$^2$)—NR$^5$—, —O—C(=NR$^2$)—O—, —O—N=C(R$^4$)—, —O—C(R$^4$)=N—, —N=C(R$^4$)—O—, —(CH$_2$)$_2$—, —(C(R$^4$)$_2$)$_2$—, —(CHR$^4$)$_2$—, —(CH$_2$)$_3$—, —(C(R$^4$)$_2$)$_3$—, —(CHR$^4$)$_3$—, cycloalkyl, and heterocycloalkyl:

provided that 0 to 2 of the G$^1$, G$^2$, G$^3$, and G$^4$ moieties are —N(R$^2$)$_d$— and each R$^2$ is independently selected and each d is independently selected, and provided that Ring (A) does not have three consecutive ring nitrogen atoms;

R$^1$ is selected from the group consisting of: alkyl-, alkenyl-, alkynyl-, aryl-, arylalkyl-, alkylaryl-, cycloalkyl-, cycloalkenyl, cycloalkylalkyl-, fused benzocycloalkyl (i.e., benzofusedcycloalkyl), fused benzoheterocycloalkyl (i.e., benzofusedhetero-cycloalkyl), fused heteroarylcycloalkyl (i.e., heteroarylfusedcycloalkyl), fused heteroarylheterocycloalkyl (i.e., heteroarylfusedheterocycloalkyl), fused cycloalkylaryl (i.e., cycloalkyfusedlaryl), fused heterocycloalkylaryl (i.e., hetero-cycloalkylfusedaryl), fused cycloalkylheteroaryl (i.e., cycloalkylfusedheteroaryl), fused heterocycloalkylheteroaryl (i.e., heterocycloalkylfusedheteroaryl), fused benzocycloalkyl alkyl (i.e., benzofusedcycloalkyl alkyl), fused benzoheterocycloalkyl alkyl (i.e., benzofusedhetero-cycloalkyl alkyl), fused heteroarylcycloalkyl alkyl (i.e., heteroarylfusedcycloalkyl alkyl), fused heteroaryiheterocycloalkyl alkyl (i.e., heteroarylfusedheterocycloalkyl alkyl), fused cycloalkylaryl alkyl (i.e., cycloalkyfusedlaryl alkyl), fused heterocycloalkylaryl alkyl (i.e., hetero-cycloalkylfusedaryl alkyl), fused cycloalkylheteroaryl alkyl (i.e., cycloalkylfusedheteroaryl alkyl), fused heterocycloalkylheteroaryl alkyl (i.e., heterocycloalkylfusedheteroaryl alkyl), heteroaryl-, heteroarylalkyl-, heterocyclyl-, heterocyclenyl, -and heterocyclyalkyl-; wherein each of said alkyl-, alkenyl- and alkynyl-, aryl-, arylalkyl-, alkylaryl-, cycloalkyl-, cycloalkenyl-, cycloalkylalkyl-, fused benzocycloalkyl, fused benzoheterocycloalkyl, fused heteroarylcycloalkyl, fused heteroarylheterocycloalkyl, fused cycloalkylaryl, fused heterocycloalkylaryl, fused cycloalkylheteroaryl, fused heterocycloalkylheteroaryl, fused benzocycloalkyl alkyl, fused benzoheterocycloalkyl alkyl, fused heteroarylcycloalkyl alkyl, fused heteroarylheterocycloalkyl alkyl, fused cycloalkylaryl alkyl, fused heterocycloalkylaryl alkyl, fused cycloalkylheteroaryl alkyl, fused heterocycloalkylheteroaryl alkyl, heteroaryl-, heteroarylalkyl-, heterocyclyl-, heterocyclenyl and heterocyclyalkyl-R$^1$ groups is optionally substituted with 1-5 independently selected R$^{21}$ groups;

Each R$^2$ is independently selected from the group consisting of: H, —OH, —O-alkyl (i.e., alkoxy), —O-(halo substituted alky) (such as, for example, —O-fluoroalkyl), —NH(R$^4$), —N(R$^4$)$_2$ (wherein each R$^4$ is independently selected), —NH$_2$, —S(O)R$^4$, —S(O)(OR$^4$), —S(O)$_2$R$^4$, —S(O)$_2$(OR$^4$), —S(O)NHR$^4$, —S(O)N(R$_4$)$_2$ (wherein each R$^4$ is independently selected), —S(O)NH$_2$, —S(O)$_2$NHR$^4$, —S(O)$_2$N(R$^4$)$_2$ (wherein each R$^4$ is independently selected), —S(O)$_2$NH$_2$, —CN, —C(O)$_2$R$^4$, —C(O)NHR$^4$, —C(O)N(R$^4$)$_2$ (wherein each R$^4$ is independently selected), —C(O)NH$_2$, —C(O)R$^4$, unsubstituted aryl, substituted aryl, unsubstituted heteroaryl, substituted heteroaryl, unsubstituted substituted alkyl, unsubstituted arylalkyl-, substituted arylalkyl-, unsubstituted heteroarylalkyl-, substituted heteroarylalkyl-, unsubstituted alkenyl, substituted alkenyl, unsubstituted alkynyl, substituted alkynyl, unsubstituted cycloalkyl, and substituted cycloalkyl, wherein said substituted aryl, heteroaryl, alkyl, arylalkyl-, heteroarylalkyl-, alkenyl, alkynyl and cycloalkyl groups are substituted with 1 to 5 independently selected R$^{21}$ groups;

R$^3$ is selected from the group consisting of: H, —OH, halo, —O-alkyl (i.e., alkoxy), —O-(halo substituted alky) (such as, for example, —O-fluoroalkyl), —NH(R$^4$), —N(R$^4$)$_2$ (wherein each R$^4$ is independently selected), —NH$_2$, —S(R$^4$), —S(O)R$^4$, —S(O)(OR$^4$), —S(O)$_2$R$^4$, —S(O)$_2$(OR$^4$), —S(O)NHR$^4$, —S(O)N(R$^4$)$_2$ (wherein each R$^4$ is independently selected), —S(O)NH$_2$, —S(O)$_2$NHR$^4$, —S(O)$_2$N(R$^4$)$_2$ (wherein each R$^4$ is independently selected), —S(O)$_2$NH$_2$, —CN, —C(O)$_2$R$^4$, —C(O)NHR$^4$, —C(O)N(R$^4$)$_2$ (wherein each R$^4$ is independently selected), —C(O)NH$_2$, —C(O)R$^4$, unsubstituted aryl, substituted aryl, unsubstituted heteroaryl, substituted heteroaryl, unsubstituted alkyl, substituted alkyl, unsubstituted arylalkyl-, substituted arylalkyl-, unsubstituted heteroarylalkyl-, substituted heteroarylalkyl-, unsubstituted alkenyl, substituted alkenyl, unsubstituted alkynyl, substituted alkynyl, unsubstituted cycloalkyl, and substituted cycloalkyl, wherein said substituted aryl, heteroaryl, alkyl, arylalkyl-, heteroarylalkyl-, alkenyl, alkynyl and cycloalkyl groups are substituted with 1 to 5 independently selected R$^{21}$ groups;

each R$^4$ is independently selected from the group consisting of: unsubstituted aryl, substituted aryl, unsubstituted heteroaryl, substituted heteroaryl, unsubstituted alkyl, substituted alkyl, unsubstituted arylalkyl-, substituted arylalkyl-, unsubstituted heteroarylalkyl-, substituted heteroarylalkyl-, unsubstituted alkenyl, substituted alkenyl, unsubstituted alkynyl, substituted alkynyl, unsubstituted cycloalkyl, and substituted cycloalkyl, wherein said substituted aryl, heteroaryl, alkyl, arylalkyl-, heteroarylalkyl-, alkenyl, alkynyl and cycloalkyl groups are substituted with 1 to 5 independently selected R$^{21}$ groups;

each R$^5$ is independently selected from the group consisting of: H, unsubstituted alkyl, substituted alkyl, unsubstituted alkenyl, substituted alkenyl, unsubstituted alkynyl, substituted alkynyl, unsubstituted cycloalkyl, substituted cycloalkyl, unsubstituted aryl, substituted aryl, unsubstituted heteroaryl and substituted heteroaryl; wherein said substituted groups are substituted with one or more (e.g., 1 to 5) substituents independently selected from: R$^2$;

Each R$^6$ is independently selected from the group consisting of: H, halo, —CF$_3$, —O-alkyl (i.e., alkoxy), —O-(halo substituted alky) (such as, for example, —O-fluoroalkyl), —S(O)R$^4$, —S(O)(OR$^4$), —S(O)NHR$^4$, —S(O)N(R$^4$)$_2$ (wherein each R$^4$ is independently selected), —S(O)NH$_2$, —S(O)₂NHR⁴, —S(O)₂N(R⁴)₂ (wherein each R⁴ is independently selected), —S(O)₂NH₂, —C(=NOR²⁴)R²⁵, and —S(O)₂R²⁴; —CN, —C(O)₂R⁴, —C(O)NHR⁴, —C(O)N(R⁴)₂ (wherein each R⁴ is independently selected), —C(O)NH₂, —C(O)R⁴, unsubstituted aryl, substituted aryl, unsubstituted heteroaryl, substituted heteroaryl, unsubstituted alkyl, substituted alkyl, unsubstituted arylalkyl-, substituted arylalkyl-, unsubstituted heteroarylalkyl-, substituted heteroarylalkyl-, unsubstituted alkenyl, substituted alkenyl, unsubstituted alkynyl, substituted alkynyl, unsubstituted cycloalkyl, and substituted cycloalkyl, wherein said substituted aryl, heteroaryl, arylalkyl-, heteroarylalkyl-, alkenyl, alkynyl and cycloalkyl groups are substituted with 1 to 5 independently selected R²¹ groups;

R⁹ is selected from the group consisting of: arylalkoxy-, heteroarylalkoxy-, arylalkylamino-, heteroarylalkylamino-, aryl-, arylalkyl-, cycloalkyl-, cycloalkenyl, cycloalkylalkyl-, heteroaryl-, heteroarylalkyl-, heterocyclyl-, heterocyclenyl-, and heterocyclylalkyl-, wherein each of said R⁹ arylalkoxy-, heteroarylalkoxy-, arylalkylamino-, heteroarylalkylamino-, aryl-, arylalkyl-, cycloalkyl-, cycloalkenyl, cycloalkylalkyl-, heteroaryl-, heteroarylalkyl-, heterocyclyl-, heterocyclenyl-, heterocyclyalkyl- and heterocyclylalkyl- is optionally substituted with 1-5 independently selected R²¹ groups;

R¹⁰ is selected from the group consisting of: aryl- (e.g., phenyl), heteroaryl- (e.g., pyridyl), cycloalkyl-, cycloalkenyl, cycloalkylalkyl-, heterocyclyl-, heterocyclenyl-, heterocyclylalkyl-, heterocyclylalkenyl-, fused benzocycloalkyl- (i.e., benzofusedcycloalkyl-), fused benzoheterocycloalkyl- (i.e., benzofusedheterocycloalkyl-), fused heteroarylcycloalkyl- (i.e., heteroarylfusedcycloalkyl-), fused heteroarylheterocycloalkyl- (i.e., heteroarylfusedheterocycloalkyl-), fused cycloalkylaryl (i.e., cycloalkyfusedlaryl-), fused heterocycloalkylaryl- (i.e. heterocycloalkylfusedaryl-), fused cycloalkylheteroaryl- (i.e., cycloalkylfusedheteroaryl-), fused heterocycloalkylheteroaryl- (i.e., heterocycloalkylfusedheteroaryl-),

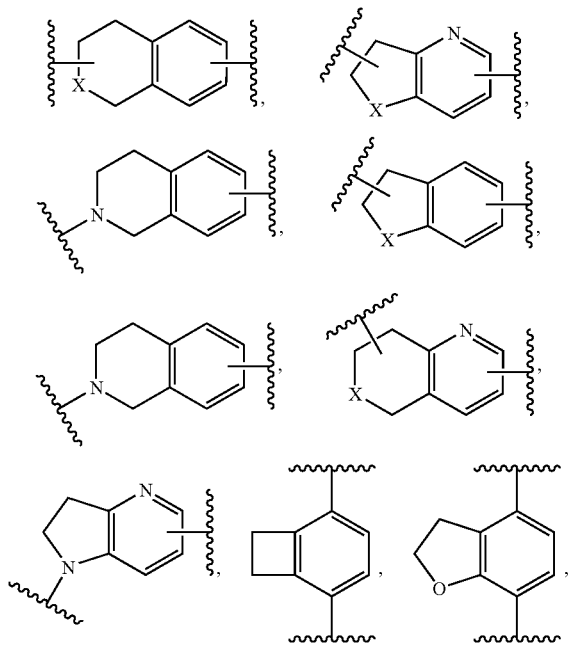

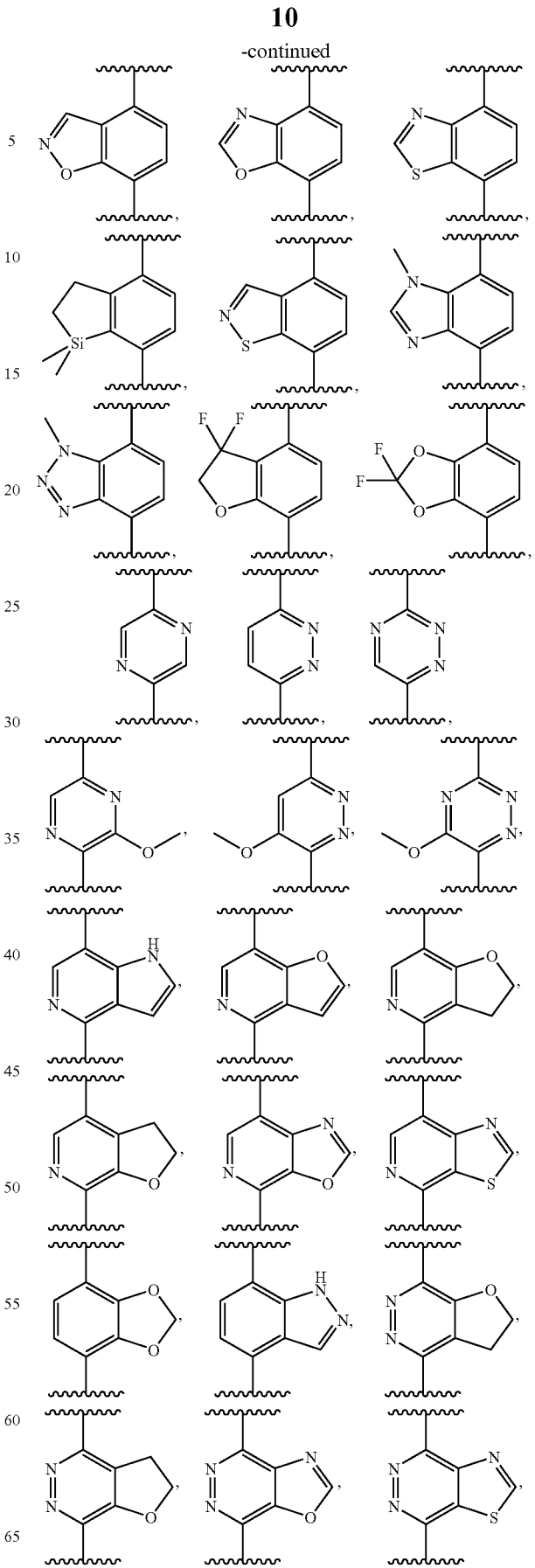

-continued

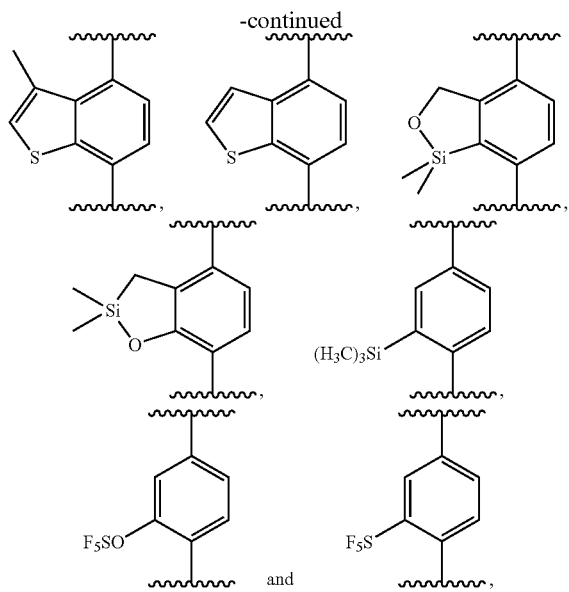

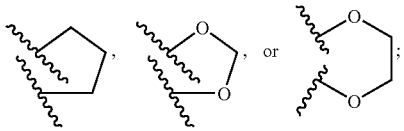

wherein X is selected from the group consisting of: O, —N($R^{14}$)— and —S—; and wherein each of said $R^{10}$ moieties is optionally substituted with 1-5 independently selected $R^{21}$ groups; or $R^9$ and $R^{10}$ are linked together to form a fused tricyclic ring system wherein $R^9$ and $R^{10}$ are as defined above and the ring linking $R^9$ and $R^{10}$ is an alkyl ring, or a heteroalkyl ring, or an aryl ring, or a heteroaryl ring, or an alkenyl ring, or a heteroalkenyl ring (for example, the tricyclic ring system is formed by linking the atoms adjacent to the atoms by which $R^9$ and $R^{10}$ are bound together);

$R^{14}$ is selected from the group consisting of H, alkyl, alkenyl, alkynyl, cycloalkyl, cycloalkylalkyl, cycloalkenyl, heterocyclyl, heterocyclenyl, heterocyclylalkyl, heterocyclyalkenyl-, aryl, arylalkyl, heteroaryl, heteroarylalkyl, —CN, —C(O)$R^{15}$, —C(O)O$R^{15}$, —C(O)N($R^{15}$)($R^{16}$), —S(O)N($R^{15}$)($R^{16}$), —S(O)$_2$N($R^{15}$)($R^{16}$), —C(=NO$R^{15}$)$R^{16}$, and —P(O)(O$R^{15}$)(O$R^{16}$);

$R^{15A}$ and $R^{16A}$ are independently selected from the group consisting of alkyl, alkenyl, alkynyl, cycloalkyl, cycloalkylalkyl, heterocyclyl, heterocyclylalkyl, aryl, arylalkyl, heteroaryl, heteroarylalkyl, arylcycloalkyl, arylheterocyclyl, ($R^{18}$)$_n$-alkyl, ($R^{18}$)$_n$-cycloalkyl, ($R^{18}$)$_n$-cycloalkylalkyl, ($R^{18}$)$_n$-heterocyclyl, ($R^{18}$)$_n$-heterocyclylalkyl, ($R^{18}$)$_n$-aryl, ($R^{18}$)$_n$-arylalkyl, ($R^{18}$)$_n$-heteroaryl and ($R^{18}$)$_n$-heteroarylalkyl; or $R^{15}$, $R^{16}$ and $R^{17}$ are independently selected from the group consisting of H, alkyl, alkenyl, alkynyl, cycloalkyl, cycloalkylalkyl, heterocyclyl, heterocyclylalkyl, aryl, arylalkyl, heteroaryl, heteroarylalkyl, arylcycloalkyl, arylheterocyclyl, ($R^{18}$)$_n$-alkyl, ($R^{18}$)$_n$-cycloalkyl, ($R^{18}$)$_n$-cycloalkylalkyl, ($R^{18}$)$_n$-heterocyclyl, ($R^{18}$)$_n$-heterocyclylalkyl, ($R^{18}$)$_n$-aryl, ($R^{18}$)$_n$-arylalkyl, ($R^{18}$)$_n$-heteroaryl and ($R^{18}$)$_n$-heteroarylalkyl;

each $R^{18}$ is independently selected from the group consisting of alkyl, alkenyl, alkynyl, aryl, arylalkyl, arylalkenyl, arylalkynyl, —NO$_2$, halo, heteroaryl, HO-alkyoxyalkyl, —CF$_3$, —ON, alkyl-CN, —C(O)$R^{19}$, —C(O)OH, —C(O)O$R^{19}$, —C(O)NH$R^{20}$, —C(O)NH$_2$, —C(O)NH$_2$—C(O)N(alkyl)$_2$, —C(O)N(alkyl)(aryl), —C(O)N(alkyl)(heteroaryl), —S$R^{19}$, —S(O)$_2R^{20}$—S(O)NH(alkyl), —S(O)N(alkyl)(alkyl), —S(O)NH(aryl), —S(O)$_2$NH$_2$, —S(O)$_2$NH$R^{19}$, —S(O)$_2$NH(heterocyclyl), —S(O)$_2$N(alkyl)$_2$, —S(O)$_2$N(alkyl)(aryl), —OCF$_3$, —OH, —O$R^{20}$, —O-heterocyclyl, —O-cycloalkylalkyl, —O-heterocyclylalkyl, —NH$_2$, —NH$R^{20}$, —N(alkyl)$_2$, —N(arylalkyl)$_2$, —N(arylalkyl)-(heteroarylalkyl), —NHC(O)$R^{20}$, —NHC(O)NH$_2$, —NHC(O)NH(alkyl), —NHC(O)N(alkyl)(alkyl), —N(alkyl)C(O)NH(alkyl), —N(alkyl)C(O)N(alkyl)(alkyl), —NHS(O)$_2R^{20}$, —NHS(O)$_2$NH(alkyl), —NHS(O)$_2$N(alkyl)(alkyl), —N(alkyl)S(O)$_2$NH(alkyl) and —N(alkyl)S(O)$_2$N(alkyl)(alkyl); or two $R^{18}$ moieties on adjacent carbons can be linked together to form a

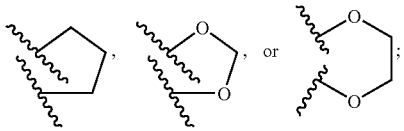 [SMILES: *CCC* ; *OCO* ; *OCCO*]

$R^{19}$ is selected from the group consisting of: alkyl, cycloalkyl, aryl, arylalkyl and heteroarylalkyl;

$R^{20}$ is selected from the group consisting of: alkyl, cycloalkyl, aryl, halo substituted aryl, arylalkyl, heteroaryl and heteroarylalkyl;

each $R^{21}$ is independently selected from the group consisting of: alkyl, alkenyl, alkynyl, cycloalkyl, cycloalkylalkyl, cycloalkenyl, heterocycloalkyl, heterocycloalkylalkyl, aryl, arylalkyl, heteroaryl, heteroarylalkyl, halo, —ON, —O$R^{15}$, —C(O)$R^{15}$, —C(O)O$R^{15}$, —C(O)N($R^{15}$)($R^{16}$), —S$R^{15}$, —P(O)(CH$_3$)$_2$, —SO(=N$R^{15}$)$R^{16}$—, —SF$_5$, —OSF$_5$, —Si($R^{15A}$)$_3$ wherein each $R^{15A}$ is independently selected —S(O)N($R^{15}$)($R^{16}$), —CH($R^{15}$)($R^{16}$), —S(O)$_2$N($R^{15}$)($R^{16}$), —C(=NO$R^{15}$)$R^{16}$, —P(O)(O$R^{15}$)(O$R^{16}$), —N($R^{15}$)($R^{16}$), -alkyl-N($R^{15}$)($R^{16}$), —N($R^{15}$)C(O)$R^{16}$, —CH$_2$—N($R^{15}$)C(O)$R^{16}$, —CH$_2$—N($R^{15}$)C(O)N($R^{16}$)($R^{17}$), —CH$_2$—$R^{15}$; —CH$_2$N($R^{15}$)($R^{16}$), —N($R^{15}$)S(O)$R^{16A}$, —N($R^{15}$)S(O)$_2R^{16A}$, —CH$_2$—N($R^{15}$)S(O)$_2R^{16A}$, —N($R^{15}$)S(O)$_2$N($R^{16}$)($R^{17}$), —N($R^{15}$)S(O)N($R^{16}$)($R^{17}$), —N($R^{15}$)C(O)N($R^{16}$)($R^{17}$), —CH$_2$—N($R^{15}$)C(O)N($R^{16}$)($R^{17}$), —N($R^{15}$)C(O)O$R^{16}$, —CH$_2$—N($R^{15}$)C(O)O$R^{16}$, —S(O)$R^{15A}$, =NO$R^{15}$, —N$_3$, —NO$_2$, —S(O)$_2R^{15A}$, —O—N=C($R^4$)$_2$ (wherein each $R^4$ is independently selected), and —O—N=C($R^4$)$_2$ wherein $R^4$ is taken together with the carbon atom to which they are bound to form a 5 to 10 membered ring, said ring optionally containing 1 to 3 heteroatoms selected from the group consisting of —O—, —S—, —S(O)—, —S(O)$_2$—, and —N$R^2$—; wherein each of said alkyl, alkenyl, alkynyl, cycloalkyl, cycloalkylalkyl, cycloalkenyl, heterocycloalkyl, heterocycloalkylalkyl, aryl, arylalkyl, heteroaryl, and heteroarylalkyl $R^{21}$ groups is optionally substituted with 1 to 5 independently selected $R^{22}$ groups;

each $R^{22}$ group is independently selected from the group consisting of alkyl, cycloalkyl, cycloalkenyl, heterocycloalkyl, aryl, heteroaryl, halo, —CF$_3$, —CN, —O$R^{15}$, —C(O)$R^{15}$, —C(O)O$R^{15}$, -alkyl-C(O)O$R^{15}$, C(O)N($R^{15}$)($R^{16}$), —S$R^{15}$, —S(O)N($R^{15}$)($R^{16}$), —S(O)$_2$N($R^{15}$)($R^{16}$), —C(=NO$R^{15}$)$R^{16}$, —P(O)(O$R^{15}$)(O$R^{16}$), —N($R^{15}$)($R^{16}$), -alkyl-N($R^{15}$)($R^{16}$), —N($R^{15}$)C(O)$R^{16}$, —CH$_2$—N($R^{15}$)C(O)$R^{16}$, —N($R^{15}$)S(O)$R^{16A}$, —N($R^{15}$)S(O)$_2R^{16A}$, —CH$_2$—N($R^{15}$)S(O)$_2R^{16A}$, —N($R^{15}$)S(O)$_2$N($R^{16}$)($R^{17}$), —N($R^{15}$)S(O)N($R^{16}$)($R^{17}$), —N($R^{15}$)C(O)N($R^{16}$)($R^{17}$), —CH$_2$—N($R^{15}$)C(O)N($R^{16}$)($R^{17}$), —N($R^{15}$)C(O)O$R^{16}$, —CH$_2$—N($R^{15}$)C(O)O$R^{16}$, —N$_3$, =NO$R^{15}$, —NO$_2$, —S(O)$R^{15A}$ and —S(O)$_2R^{15A}$; and provided that:

Ring (A) does not have any —S—S—, —S—S(O)—, —S—S(O)$_2$—, —S(O)—S(O)—, —S(O)—S(O)$_2$—, or —S(O)$_2$—S(O)$_2$— bonds in the ring;

Ring (A) does not have any —O—O— bonds in the ring;

Ring (A) does not have any —O—S—, —O—S(O)—, or —O—S(O)$_2$— bonds in the ring;

Ring (A) does not have any —N—S—N— bonds in the ring;

Ring (A) does not have any —N—O—N— bonds in the ring; and

Ring (A) does not have three adjacent nitrogent atoms in the ring.

The compounds of this invention are useful for treating central nervous system disorders such as, for example, neurodegenerative diseases such as Alzheimer's disease and other diseases relating to the deposition of amyloid protein. They are especially useful for reducing Amyloid beta (hereinafter referred to as Aβ) production which is effective in the treatment of diseases caused by Aβ such as, for example, Alzheimers and Down Syndrome.

Thus, for example, the compounds of this invention can be used to treat the following diseases or conditions: Alzheimers disease, mild cognitive impairment (MCI), Downs Syndrome, Glaucoma (Guo et. al., Proc. Natl. Acad. Sci. USA 104, 13444-13449 (2007)), Cerebral amyloid angiopathy, stroke or dementia (Frangione et al., Amyloid: J. Protein folding Disord. 8, suppl. 1, 36-42 (2001), Microgliosis and brain inflammation (M P Lamber, Proc. Natl. Acad. Sci, USA 95, 6448-53 (1998)), and Olfactory function loss (Getchell, et. al. Neurobiology of Aging, 663-673, 24, 2003).

In one embodiment of the invention, $R^1$ is selected from the group consisting of: alkyl-, alkenyl-, alkynyl-, aryl-, arylalkyl-, alkylaryl-, cycloalkyl-, cycloalkenyl, cycloalkylalkyl-, fused benzocycloalkyl (i.e., benzofusedcycloalkyl), fused benzoheterocycloalkyl (i.e., benzofusedhetero-cycloalkyl), fused heteroarylcycloalkyl (i.e., heteroarylfusedcycloalkyl), fused heteroarylheterocycloalkyl (i.e., heteroarylfusedheterocycloalkyl), heteroaryl-, heteroarylalkyl-, heterocyclyl-, heterocyclenyl, -and heterocyclyalkyl-; and wherein each of said alkyl-, alkenyl- and alkynyl-, aryl-, arylalkyl-, alkylaryl-, cycloalkyl-, cycloalkenyl-, cycloalkylalkyl-, fused benzocycloalkyl, fused benzoheterocycloalkyl, fused heteroarylcycloalkyl, fused heteroarylheterocycloalkyl, heteroaryl-, heteroarylalkyl-, heterocyclyl-, heterocyclenyl and heterocyclyalkyl-$R^1$ groups is optionally substituted with 1-5 independently selected $R^{21}$ groups.

Examples of moieties formed when $R^{10}$ and $R^9$ are linked together to form a fused tricyclic ring system include, but are not limited to:

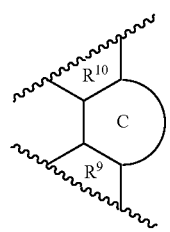

wherein $R^{10}$ and $R^9$ are as defined for formula (I), and Ring C is the ring linking $R^{10}$ and $R^9$, that is Ring C is an alkyl ring, or a heteroalkyl ring, or an aryl ring, or a heteroaryl ring, or an alkenyl ring, or a heteroalkenyl ring.

Examples of moieties formed when $R^{10}$ and $R^9$ are linked together to form a fused tricyclic ring system include, but are not limited to:

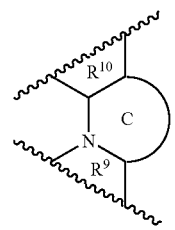

wherein $R^{10}$ and $R^9$ are as defined for formula (I), and Ring C is the ring linking $R^{10}$ and $R^9$, that is Ring C is a heteroalkyl ring, or a heteroaryl ring, or a heteroalkenyl ring.

In one example, the fused tricyclic ring system formed when $R^{10}$ and $R^9$ are linked together is

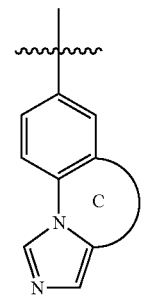

wherein Ring C is a heteroalkyl ring, or a heteroaryl ring, or a heteroalkenyl ring, thus, for example, the tricyclic ring system is formed by linking the atoms adjacent to the atoms by which $R^{10}$ and $R^9$ are bound together), and wherein said fused tricyclic ring system is optionally substituted with 1 to 5 independently selected $R^{21}$ groups.

Other examples of moieties formed when $R^{10}$ and $R^9$ are linked together to form a fused tricyclic ring system include, but are not limited to:

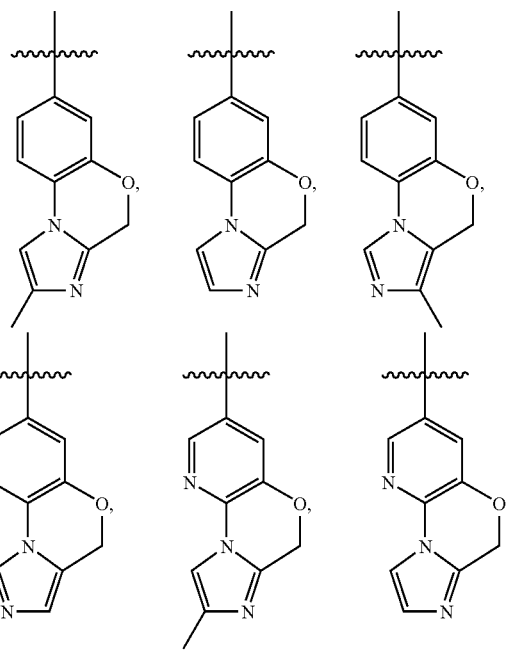

Another embodiment of this is directed to compounds of formula (I) wherein at least one (e.g., 1 to 3, or 1-2, or 1) group selected from the group consisting of: —SF$_5$, —OSF$_5$, and —Si(R$^{15A}$)$_3$ is present, and wherein each R$^{15A}$ is independently selected, and wherein when there is more than one group, each group is independently selected.

Another embodiment of this is directed to compounds of formula (I) wherein at least one (e.g., 1 to 3, or 1-2, or 1) group selected from the group consisting of: —SF$_5$ and —OSF$_5$ is present, and wherein when there is more than one group, each group is independently selected.

In one embodiment of this invention one group selected from the group consisting of: —SF$_5$, —OSF$_5$, and —Si(R$^{15A}$)$_3$ (wherein each R$^{15A}$ is independently selected) is present in the compounds of formula (I).

In another embodiment of this invention two groups selected from the group consisting of: —SF$_5$, —OSF$_5$, and —Si(R$^{15A}$)$_3$ (wherein each R$^{15A}$ is independently selected) are present in the compounds of formula (I).

In another embodiment of this invention three groups selected from the group consisting of: —SF$_5$, —OSF$_5$, and —Si(R$^{15A}$)$_3$ (wherein each R$^{15A}$ is independently selected) are present in the compounds of formula (I).

In another embodiment of this invention two groups selected from the group consisting of: —SF$_5$, —OSF$_5$, and —Si(R$^{15A}$)$_3$ (wherein each R$^{15A}$ is independently selected) are present in the compounds of formula (I), wherein at least one group is other than —Si(R$^{15A}$)$_3$.

In another embodiment of this invention three groups selected from the group consisting of: —SF$_5$, —OSF$_5$, and —Si(R$^{15A}$)$_3$ (wherein each R$^{15A}$ is independently selected) are present in the compounds of formula (I), wherein at least one group is other than —Si(R$^{15A}$)$_3$.

In another embodiment of this invention one group selected from the group consisting of: —SF$_5$, —OSF$_5$, and —Si(R$^{15A}$)$_3$ (wherein each R$^{15A}$ is independently selected from the group consisting of alkyl (e.g., methyl and ethyl) and aryl (e.g., phenyl)) is present in the compounds of formula (I).

In another embodiment of this invention two groups selected from the group consisting of: —SF$_5$, —OSF$_5$, and —Si(R$^{15A}$)$_3$ (wherein each R$^{15A}$ is independently selected from the group consisting of alkyl (e.g., methyl and ethyl) and aryl (e.g., phenyl)) are present in the compounds of formula (I).

In another embodiment of this invention three groups selected from the group consisting of: —SF$_5$, —OSF$_5$, and —Si(R$^{15A}$)$_3$ (wherein each R$^{15A}$ is independently selected from the group consisting of alkyl (e.g., methyl and ethyl) and aryl (e.g., phenyl)) are present in the compounds of formula (I).

In another embodiment of this invention two groups selected from the group consisting of: —SF$_5$, —OSF$_5$, and —Si(R$^{15A}$)$_3$ (wherein each R$^{15A}$ is independently selected from the group consisting of alkyl (e.g., methyl and ethyl) and aryl (e.g., phenyl)) are present in the compounds of formula (I), wherein at least one group is other than —Si(R$^{15A}$)$_3$.

In another embodiment of this invention three groups selected from the group consisting of: —SF$_5$, —OSF$_5$, and —Si(R$^{15A}$)$_3$ (wherein each R$^{15A}$ is independently selected from the group consisting of alkyl (e.g., methyl and ethyl) and aryl (e.g., phenyl)) are present in the compounds of formula (I), wherein at least one group is other than —Si(R$^{15A}$)$_3$.

In another embodiment of this invention one group selected from the group consisting of: —SF$_5$, —OSF$_5$, and —Si(R$^{15A}$)$_3$ (wherein each R$^{15A}$ is independently selected from the group consisting of methyl, ethyl and phenyl) is present in the compounds of formula (I).

In another embodiment of this invention two groups selected from the group consisting of: —SF$_5$, —OSF$_5$, and —Si(R$^{15A}$)$_3$ (wherein each R$^{15A}$ is independently selected from the group consisting of methyl, ethyl and phenyl) are present in the compounds of formula (I).

In another embodiment of this invention three groups selected from the group consisting of: —SF$_5$, —OSF$_5$, and —Si(R$^{15A}$)$_3$ (wherein each R$^{15A}$ is independently selected from the group consisting of methyl, ethyl and phenyl) are present in the compounds of formula (I).

In another embodiment of this invention two groups selected from the group consisting of: —SF$_5$, —OSF$_5$, and —Si(R$^{15A}$)$_3$ (wherein each R$^{15A}$ is independently selected from the group consisting of methyl, ethyl and phenyl) are present in the compounds of formula (I), wherein at least one group is other than —Si(R$^{15A}$)$_3$.

In another embodiment of this invention three groups selected from the group consisting of: —SF$_5$, —OSF$_5$, and —Si(R$^{15A}$)$_3$ (wherein each R$^{15A}$ is independently selected from the group consisting of methyl, ethyl and phenyl) are present in the compounds of formula (I), wherein at least one group is other than —Si(R$^{15A}$)$_3$.

In another embodiment of this invention one group selected from the group consisting of: —SF$_5$, —OSF$_5$, and —Si(R$^{15A}$)$_3$ (wherein each R$^{15A}$ is independently selected from the group consisting of methyl and ethyl) is present in the compounds of formula (I).

In another embodiment of this invention two groups selected from the group consisting of: —SF$_5$, —OSF$_5$, and —Si(R$^{15A}$)$_3$ (wherein each R$^{15A}$ is independently selected from the group consisting of methyl and ethyl) are present in the compounds of formula (I).

In another embodiment of this invention three groups selected from the group consisting of: —SF$_5$, —OSF$_5$, and —Si(R$^{15A}$)$_3$ (wherein each R$^{15A}$ is independently selected from the group consisting of methyl and ethyl) are present in the compounds of formula (I).

In another embodiment of this invention two groups selected from the group consisting of: —SF$_5$, —OSF$_5$, and —Si(R$^{15A}$)$_3$ (wherein each R$^{15A}$ is independently selected from the group consisting of methyl and ethyl) are present in the compounds of formula (I), wherein at least one group is other than —Si(R$^{15A}$)$_3$.

In another embodiment of this invention three groups selected from the group consisting of: —SF$_5$, —OSF$_5$, and —Si(R$^{15A}$)$_3$ (wherein each R$^{15A}$ is independently selected from the group consisting of methyl and ethyl) are present in the compounds of formula (I), wherein at least one group is other than —Si(R$^{15A}$)$_3$.

In another embodiment of this invention one group selected from the group consisting of: —SF$_5$, —OSF$_5$, and —Si(R$^{15A}$)$_3$ is present in the compounds of formula (I), and said —Si(R$^{15A}$)$_3$ group is selected from the group consisting of: —Si(CH$_3$)$_3$, —Si(CH$_3$)$_2$-phenyl, and —Si(CH$_2$CH$_3$)$_2$CH$_3$.

In another embodiment of this invention two groups selected from the group consisting of: —SF$_5$, —OSF$_5$, and —Si(R$^{15A}$)$_3$ are present in the compounds of formula (I), and said —Si(R$^{15A}$)$_3$ group is selected from the group consisting of: —Si(CH$_3$)$_3$, —Si(CH$_3$)$_2$-phenyl, and —Si(CH$_2$CH$_3$)$_2$CH$_3$.

In another embodiment of this invention three groups selected from the group consisting of: —SF$_5$, —OSF$_5$, and —Si(R$^{15A}$)$_3$ are present in the compounds of formula (I), and said —Si(R$^{15A}$)$_3$ group is selected from the group consisting of: —Si(CH$_3$)$_3$, —Si(CH$_3$)$_2$-phenyl, and —Si(CH$_2$CH$_3$)$_2$CH$_1$ In another embodiment of this invention two groups selected from the group consisting of: —SF$_5$, —OSF$_5$, and —Si(R$^{15A}$)$_3$ are present in the compounds of formula (I), wherein at least one group is other than —Si(R$^{15A}$)$_3$, and said —Si(R$^{15A}$)$_3$ group is selected from the group consisting of: —Si(CH$_3$)$_3$, —Si(CH$_3$)$_2$-phenyl, and —Si(CH$_2$CH$_3$)$_2$CH$_3$.

In another embodiment of this invention three groups selected from the group consisting of: —SF$_5$, —OSF$_5$, and —Si(R$^{15A}$)$_3$ are present in the compounds of formula (I), wherein at least one group is other than —Si(R$^{15A}$)$_3$, and said —Si(R$^{15A}$)$_3$ group is selected from the group consisting of: —Si(CH$_3$)$_3$, —Si(CH$_3$)$_2$-phenyl, and —Si(CH$_2$CH$_3$)$_2$CH$_3$.

In another embodiment of this invention one group selected from the group consisting of: —SF$_5$, —OSF$_5$, and —Si(R$^{15A}$)$_3$ is present in the compounds of formula (I), and said —Si(R$^{15A}$)$_3$ group is selected from the group consisting of: —Si(CH$_3$)$_3$ and —Si(CH$_2$CH$_3$)$_2$CH$_3$ In another embodiment of this invention two groups selected from the group consisting of: —SF$_5$, —OSF$_5$, and —Si(R$^{15A}$)$_3$ are present in the compounds of formula (I), and said —Si(R$^{15A}$)$_3$ group is selected from the group consisting of: —Si(CH$_3$)$_3$ and —Si(CH$_2$CH$_3$)$_2$CH$_3$.

In another embodiment of this invention three groups selected from the group consisting of: —SF$_5$, —OSF$_5$, and —Si(R$^{15A}$)$_3$ are present in the compounds of formula (I) and said —Si(R$^{15A}$)$_3$ group is selected from the group consisting of: —Si(CH$_3$)$_3$ and —Si(CH$_2$CH$_3$)$_2$CH$_3$.

In another embodiment of this invention two groups selected from the group consisting of: —SF$_5$, —OSF$_5$, and —Si(R$^{15A}$)$_3$ are present in the compounds of formula (I), wherein at least one group is other than —Si(R$^{15A}$)$_3$, and said —Si(R$^{15A}$)$_3$ group is selected from the group consisting of: —Si(CH$_3$)$_3$ and —Si(CH$_2$CH$_3$)$_2$CH$_3$.

In another embodiment of this invention three groups selected from the group consisting of: —SF$_5$, —OSF$_5$, and —Si(R$^{15A}$)$_3$ are present in the compounds of formula (I), wherein at least one group is other than —Si(R$^{15A}$)$_3$, and said —Si(R$^{15A}$)$_3$ group is selected from the group consisting of: —Si(CH$_3$)$_3$, —Si(CH$_3$)$_2$-phenyl, and —Si(CH$_2$CH$_3$)$_2$CH$_3$.

In another embodiment of this invention one group selected from the group consisting of: —SF$_5$, —OSF$_5$, and —Si(CH$_3$)$_3$ is present.

In another embodiment of this invention two groups selected from the group consisting of: —SF$_5$, —OSF$_5$, and —Si(CH$_3$)$_3$ are present in the compounds of formula (I).

In another embodiment of this invention three groups selected from the group consisting of: —SF$_5$, —OSF$_5$, and —Si(CH$_3$)$_3$ are present in the compounds of formula (I).

In another embodiment of this invention two groups selected from the group consisting of: —SF$_5$, —OSF$_5$, and —Si(CH$_3$)$_3$ are present in the compounds of formula (I), wherein at least one group is other than —Si(CH$_3$)$_3$.

In another embodiment of this invention three groups selected from the group consisting of: —SF$_5$, —OSF$_5$, and —Si(R$^{24}$)$_3$ are present in the compounds of formula (I), wherein at least one group is other than —Si(CH$_3$)$_3$ In another embodiment of this invention one group selected from the group consisting of: —SF$_5$ and —OSF$_5$ is present in the compounds of formula (I).

In another embodiment of this invention two groups selected from the group consisting of: —SF$_5$ and —OSF$_5$ are present in the compounds of formula (I).

In another embodiment of this invention three groups selected from the group consisting of: —SF$_5$ and —OSF$_5$ are present in the compounds of formula (I)

In another embodiment of this invention one —SF$_5$ group is present in the compounds of formula (I).

In another embodiment of this invention two —SF$_5$ groups are present in the compounds of formula (I).

In another embodiment of this invention three —SF$_5$ groups are present in the compounds of formula (I).

In another embodiment of this invention one —OSF$_5$ group is present in the compounds of formula (I).

In another embodiment of this invention two —OSF$_5$ groups are present in the compounds of formula (I).

In another embodiment of his invention three —OSF$_5$ groups are present in the compounds of formula (I).

In another embodiment of this invention one —Si(R$^{15a}$)$_3$ (wherein each R$^{15A}$ is independently selected) group is present in the compounds of formula (I).

In another embodiment of this invention two —Si(R$^{15A}$)$_3$ (wherein each R$^{15A}$ is independently selected) groups are present in the compounds of formula (I).

In another embodiment of this invention three —Si(R$^{15A}$)$_3$ (wherein each R$^{15A}$ is independently selected) groups are present in the compounds of formula (I).

In another embodiment of this invention one —Si(R$^{15A}$)$_3$ (wherein each R$^{15A}$ is independently selected from the group consisting of alkyl (e.g., methyl and ethyl) and aryl (e.g., phenyl)) is present in the compounds of formula (I).

In another embodiment of this invention two —Si(R$^{15A}$)$_3$ (wherein each R$^{15A}$ is independently selected from the group consisting of alkyl (e.g., methyl and ethyl) and aryl (e.g., phenyl)) is present in the compounds of formula (I).

In another embodiment of this invention three —Si(R$^{15A}$)$_3$ (wherein each R$^{15A}$ is independently selected from the group consisting of alkyl (e.g., methyl and ethyl) and aryl (e.g., phenyl)) is present in the compounds of formula (I).

In another embodiment of this invention one —Si(R$^{15A}$)$_3$ (wherein each R$^{15A}$ is independently selected from the group consisting of methyl, ethyl and phenyl) is present in the compounds of formula (I).

In another embodiment of this invention two —Si(R$^{15A}$)$_3$ (wherein each R$^{15A}$ is independently selected from the group consisting of methyl, ethyl and phenyl) is present in the compounds of formula (I).

In another embodiment of this invention three —Si(R$^{15A}$)$_3$ (wherein each R$^{15A}$ is independently selected from the group consisting of methyl, ethyl and phenyl) is present in the compounds of formula (I).

In another embodiment of this invention one —Si(R$^{15A}$)$_3$ (wherein each R$^{15A}$ is independently selected from the group consisting of methyl and ethyl) is present in the compounds of formula (I).

In another embodiment of this invention two —Si(R$^{15A}$)$_3$ (wherein each R$^{15A}$ is independently selected from the group consisting of methyl and ethyl) is present in the compounds of formula (I).

In another embodiment of this invention three —Si(R$^{15A}$)$_3$ (wherein each R$^{15A}$ is independently selected from the group consisting of methyl and ethyl) is present in the compounds of formula (I).

In another embodiment of this invention one —Si(R$^{15A}$)$_3$ group is present in the compounds of formula (I), and said —Si(R$^{15A}$)$_3$ group is selected from the group consisting of: —Si(CH$_3$)$_3$, —Si(CH$_3$)$_2$-phenyl, and —Si(CH$_2$CH$_3$)$_2$CH$_3$.

In another embodiment of this invention two —Si(R$^{15A}$)$_3$ groups are present in the compounds of formula (I), and said —Si(R$^{15A}$)$_3$ groups are independently selected from the group consisting of: —Si(CH$_3$)$_3$, —Si(CH$_3$)$_2$-phenyl, and —Si(CH$_2$CH$_3$)$_2$CH$_3$.

In another embodiment of this invention three —Si(R$^{15A}$)$_3$ groups are present in the compounds of formula (I), and said —Si(R$^{15A}$)$_3$ groups are independently selected from the group consisting of: —Si(CH$_3$)$_3$, —Si(CH$_3$)$_2$-phenyl, and —Si(CH$_2$CH$_3$)$_2$CH$_3$.

In another embodiment of this invention one —Si(R$^{15A}$)$_3$ group is present in the compounds of formula (I), and said —Si(R$^{15A}$)$_3$ group is selected from the group consisting of: —Si(CH$_3$)$_3$ and —Si(CH$_2$CH$_3$)$_2$CH$_3$.

In another embodiment of this invention two —Si(R$^{15A}$)$_3$ groups are present in the compounds of formula (I), and said —Si(R$^{15A}$)$_3$ groups are independently selected from the group consisting of: —Si(CH$_3$)$_3$ and —Si(CH$_2$CH$_3$)$_2$CH$_3$.

In another embodiment of this invention three —Si(R$^{15A}$)$_3$ groups are present in the compounds of formula (I), and said —Si(R$^{15A}$)$_3$ groups are independently selected from the group consisting of: —Si(CH$_3$)$_3$ and —Si(CH$_2$CH$_3$)$_2$CH$_3$.

In another embodiment of this invention one —Si(R$^{15A}$)$_3$ group is present in the compounds of formula (I), and said —Si(R$^{15A}$)$_3$ group is —Si(CH$_3$)$_3$.

In another embodiment of this invention two —Si(R$^{15A}$)$_3$ groups are present in the compounds of formula (I), and said —Si(R$^{15A}$)$_3$ groups are —Si(CH$_3$)$_3$.

In another embodiment of this invention three —Si(R$^{15A}$)$_3$ groups are present in the compounds of formula (I), and said —Si(R$^{15A}$)$_3$ groups are —Si(CH$_3$)$_3$.

In another embodiment of this invention one group selected from the group consisting of: —SF$_5$, —OSF$_5$, —Si(CH$_3$)$_3$, —Si(CH$_3$)$_2$-phenyl, and —Si(CH$_2$CH$_3$)$_2$CH$_3$) is present in the compounds of formula (I), In another embodiment of this invention one group selected from the group consisting of: —SF$_5$, —OSF$_5$, —Si(CH$_3$)$_3$, and —Si(CH$_2$CH$_3$)$_2$CH$_3$) is present in the compounds of formula (I).

In another embodiment of this invention one group selected from the group consisting of: —SF$_5$, —OSF$_5$, and —Si(CH$_3$)$_3$, is present in the compounds of formula (I).

In another embodiment of this invention one —SF$_5$ group is present in the compounds of formula (I), and one or two additional groups selected from the group consisting of: —SF$_5$, —OSF$_5$, and —Si(R$^{15A}$)$_3$ (wherein each R$^{15A}$ is independently selected) are also present in the compounds of formula (I).

In another embodiment of this invention one —SF$_5$ group is present in the compounds of formula (I), and one or two additional groups selected from the group consisting of: —OSF$_5$, and —Si(R$^{15A}$)$_3$ (wherein each R$^{15A}$ is independently selected) are also present in the compounds of formula (I).

In another embodiment of this invention one —OSF$_5$ group is present in the compounds of formula (I), and one or two additional groups selected from the group consisting of: —SF$_5$, —OSF$_5$, and —Si(R$^{15A}$)$_3$ (wherein each R$^{15A}$ is independently selected) are also present in the compounds of formula (I).

In another embodiment of this invention one —OSF$_5$ group is present in the compounds of formula (I), and one or two additional groups selected from the group consisting of: —SF$_5$ and —Si(R$^{15A}$)$_3$ (wherein each R$^{15A}$ is independently selected) are also present in the compounds of formula (I).

In another embodiment of this invention one —SF$_5$ group is present in the compounds of formula (I), and one or two additional groups selected from the group consisting of: —SF$_5$ and —OSF$_5$ are also present in the compounds of formula (I).

In another embodiment of this invention one —OSF$_5$ group is present in the compounds of formula (I), and one or two additional groups selected from the group consisting of: —SF$_5$ and —OSF$_5$ are also present in the compounds of formula (I).

In another embodiment of this invention one —Si(R$^{15A}$)$_3$ (wherein each R$^{15A}$ is independently selected) group is present in the compounds of formula (I), and one or two groups selected from the group consisting of: —SF$_5$, —OSF$_5$, and —Si(R$^{15A}$)$_3$ (wherein each R$^{15A}$ is independently selected) are also present in the compounds of formula (I).

In another embodiment of this invention one —Si(R$^{15A}$)$_3$ (wherein each R$^{15A}$ is independently selected) group is present in the compounds of formula (I), and one or two groups selected from the group consisting of: —SF$_5$ and —OSF$_5$ are also present in the compounds of formula (I).

In another embodiment of this invention at least one group selected from the group consisting of: —SF$_5$, —OSF$_5$, and —Si(R$^{15A}$)$_3$ (wherein each R$^{15A}$ is independently selected from the group consisting of alkyl (e.g., methyl and ethyl) and aryl (e.g., phenyl)) is present in the compounds of formula (I).

In another embodiment of this invention at least one group selected from the group consisting of: —SF$_5$, —OSF$_5$, and —Si(R$^{15A}$)$_3$ (wherein each R$^{15A}$ is independently selected from the group consisting of alkyl (e.g., methyl and ethyl) and phenyl) is present in the compounds of formula (I).

In another embodiment of this invention at least one group selected from the group consisting of: —SF$_5$, —OSF$_5$, and —Si(R$^{15A}$)$_3$ (wherein each R$^{15A}$ is independently selected from the group consisting of methyl, ethyl and phenyl) is present in the compounds of formula (I).

In another embodiment of this invention at least one group selected from the group consisting of: —SF$_5$, —OSF$_5$, —Si(CH$_3$)$_3$, —Si(CH$_3$)$_2$-phenyl, and —Si(CH$_2$CH$_3$)$_2$CH$_3$) is present in the compounds of formula (I).

In another embodiment of this invention at least one group selected from the group consisting of: —SF$_5$, —OSF$_5$, and —Si(CH$_3$)$_3$ is present in the compounds of formula (I).

In another embodiment of this invention one group selected from the group consisting of: —SF$_5$, —OSF$_5$, and —Si(R$^{15A}$)$_3$ (wherein each R$^{15A}$ is independently selected) is present in the compounds of formula (I).

In another embodiment of this invention one group selected from the group consisting of: —SF$_5$, —OSF$_5$, and —Si(R$^{15A}$)$_3$ (wherein each R$^{15A}$ is independently selected from the group consisting of alkyl (e.g., methyl and ethyl) and aryl (e.g., phenyl)) is present in the compounds of formula (I).

In another embodiment of this invention one group selected from the group consisting of: —SF$_5$, —OSF$_5$, and —Si(R$^{15A}$)$_3$ (wherein each R$^{15A}$ is independently selected from the group consisting of alkyl (e.g., methyl and ethyl) and phenyl) is present in the compounds of formula (I).

In another embodiment of this invention one group selected from the group consisting of: —SF$_5$, —OSF$_5$, and —Si(R$^{15A}$)$_3$ (wherein each R$^{15A}$ independently selected from the group consisting of methyl, ethyl and phenyl) is present in the compounds of formula (I).

In another embodiment of this invention one group selected from the group consisting of: —SF$_5$, —OSF$_5$, —Si(CH$_3$)$_3$, —Si(CH$_3$)$_2$-phenyl, and —Si(CH$_2$CH$_3$)$_2$CH$_3$) is present in the compounds of formula (I).

In another embodiment of this invention one group selected from the group consisting of: —SF$_5$, —OSF$_5$, —Si(CH$_3$)$_3$, and —Si(CH$_2$CH$_3$)$_2$CH$_3$) is present in the compounds of formula (I).

In another embodiment of this invention one group selected from the group consisting of: —SF$_5$, —OSF$_5$, and —Si(CH$_3$)$_3$, is present in the compounds of formula (I).

In another embodiment of this invention two groups selected from the group consisting of: —SF$_5$, —OSF$_5$, and —Si(R$^{15A}$)$_3$ (wherein each R$^{15A}$ is independently selected) are present in the compounds of formula (I).

In another embodiment of this invention two groups independently selected from the group consisting of: —SF$_5$, —OSF$_5$, and —Si(R$^{15A}$)$_3$ (wherein each R$^{15A}$ is independently selected from the group consisting of alkyl (e.g., methyl and ethyl) and aryl (e.g., phenyl)) are present in the compounds of formula (I).

In another embodiment of this invention two groups independently selected from the group consisting of: —SF$_5$, —OSF$_5$, and —Si(R$^{15A}$)$_3$ (wherein each R$^{15A}$ is independently selected from the group consisting of alkyl (e.g., methyl and ethyl) and phenyl) are present in the compounds of formula (I).

In another embodiment of this invention two groups selected from the group consisting of: —SF$_5$, —OSF$_5$, and —Si(R$^{15A}$)$_3$ (wherein each R$^{15A}$ is independently selected from the group consisting of methyl, ethyl and phenyl) are present in the compounds of formula (I).

In another embodiment of this invention two groups independently selected from the group consisting of: —SF$_5$, —OSF$_5$, —Si(CH$_3$)$_3$, —Si(CH$_3$)$_2$-phenyl, and —Si(CH$_2$CH$_3$)$_2$CH$_3$) is present in the compounds of formula (I).

In another embodiment of this invention two groups independently selected from the group consisting of: —SF$_5$, —OSF$_5$, —Si(CH$_3$)$_3$, and —Si(CH$_2$CH$_3$)$_2$CH$_3$) are present in the compounds of formula (I).

In another embodiment of this invention two groups independently selected from the group consisting of: —SF$_5$, —OSF$_5$, and —Si(C$_{1-13}$)$_3$ are present in the compounds of formula (I).

In another embodiment of this invention three groups selected from the group consisting of: —SF$_5$, —OSF$_5$, and —Si(R$^{15A}$)$_3$ (wherein each R$^{15A}$ is independently selected) are present in the compounds of formula (I)I.

In another embodiment of this invention three groups independently selected from the group consisting of: —SF$_5$, —OSF$_5$, and —Si(R$^{15A}$)$_3$ (wherein each R$^{15A}$ is independently selected from the group consisting of alkyl (e.g., methyl and ethyl) and aryl (e.g., phenyl)) are present in the compounds of formula (I).

In another embodiment of this invention three groups independently selected from the group consisting of: —SF$_5$, —OSF$_5$, and —Si(R$^{15A}$)$_3$ (wherein each R$^{15A}$ is independently selected from the group consisting of alkyl (e.g., methyl and ethyl) and phenyl) are present in the compounds of formula (I).

In another embodiment of this invention three groups selected from the group consisting of: —SF$_5$, —OSF$_5$, and —Si(R$^{15A}$)$_3$ (wherein each R$^{15A}$ is independently selected from the group consisting of methyl, ethyl and phenyl) are present in the compounds of formula (I).

In another embodiment of this invention three groups independently selected from the group consisting of: —SF$_5$, —OSF$_5$, —Si(CH$_3$)$_3$, —Si(CH$_3$)$_2$phenyl, and —Si(CH$_2$CH$_3$)$_2$CH$_3$) is present in the compounds of formula (I).

In another embodiment of this invention three groups independently selected from the group consisting of: —SF$_5$, —OSF$_5$, —Si(CH$_3$)$_3$, and —Si(CH$_2$CH$_3$)$_2$CH$_3$) are present in the compounds of formula (I).

In another embodiment of this invention three groups independently selected from the group consisting of: —SF$_5$, —OSF$_5$, and —Si(CH$_3$)$_3$ are present in the compounds of formula (I).

In another embodiment of this invention at least one group selected from the group consisting of: —SF$_5$, —OSF$_5$, and —Si(R$^{15A}$)$_3$ (wherein each R$^{15A}$ is the same or different alkyl group) is present in the compounds of formula (O.

In another embodiment of this invention at least one group selected from the group consisting of: —SF$_5$, —OSF$_5$, and —Si(R$^{15A}$)$_3$ (wherein each R$^{15A}$ is independently selected from the group consisting of methyl and ethyl) is present in the compounds of formula (I).

In another embodiment of this invention one —SF$_5$ group is present in the compounds of formula (I), and one or two groups selected from the group consisting of: —SF$_5$ and —OSF$_5$ are also present in the compounds of formula (I).

In another embodiment of this invention one —OSF$_5$ group is present in the compounds of formula (I), and one or two groups selected from the group consisting of: —SF$_5$ and —OSF$_5$ are also present in the compounds of formula (I).

Those skilled in the art will appreciate that when W is —S(O)—, the —S(O)-moiety can be:

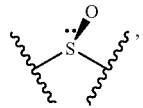

or the —S(O)-moiety can be;

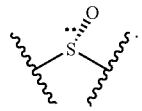

The compounds of formula (I) do not have three consecutive nitrogen atoms in the ring. Thus, including the nitrogen to which R$^1$ is bound, there are up to two additional nitrogens in the ring (i.e., up to two —N(R$^2$)$_d$— groups in the ring) provided that the nitrogens are not in consecutive ring positions. Thus, (a) when $G^1$ is $—N(R^2)_d—$ then $G^2$ is not $—N(R^2)_d—$, and (b) when $G^3$ is $—N(R^2)_d—$ and $G^2$ is $—N(R^2)_d—$ then $G^1$ is not $—N(R^2)_d—$, and (c) when $G^3$ is $—N(R^2)_d—$ and $G^1$ is $—N(R^2)_d—$ then $G^2$ is not $—N(R^2)_d—$).

In formula (I), 0 to 2 of the $G^1$, $G^2$, $G^3$, and $G^4$ moieties are $—N(R^2)_d—$ wherein each d and each $R^2$ is independently selected. Thus Ring (A) in formula (I) comprises a total of 1 to 3 nitrogen atoms (the $—NR^1$-moiety and 0 to 2 $—N(R^2)_d$- moieties) in the ring such that the Ring (A) does not comprise three consecutive ring nitrogens, and each d and each $R^2$ is independently selected.

One embodiment of this invention is directed to compounds of formula (IA):

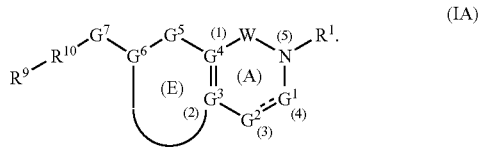

Another embodiment of this invention is directed to compounds of formula (IB):

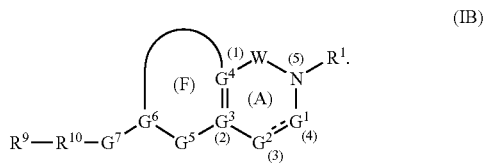

Another embodiment of this invention is directed to compounds of formula (IA) having the formula:

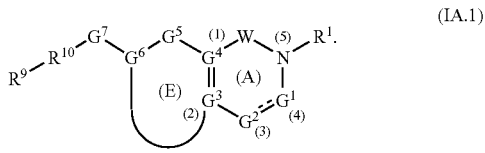

Another embodiment of this invention is directed to compounds of formula (IB) having the formula:

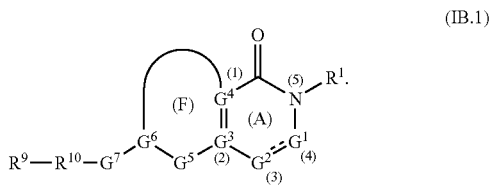

In another embodiment of this invention $G^1$ is $—C(R^{21})_q—$.

In another embodiment of this invention $G^1$ is $—N(R^2)_d—$.

In another embodiment of this invention $G^1$ is a direct bond.

In another embodiment of this invention $G^1$ is $—O—$.

In another embodiment of this invention $G^1$ is $—S—$.

In another embodiment of this invention $G^2$ is $—C(R^{21})_q—$.

In another embodiment of this invention $G^2$ is $—N(R^2)_d—$.

In another embodiment of this invention $G^2$ is a direct bond.

In another embodiment of this invention $G^2$ is $—O—$.

In another embodiment of this invention $G^2$ is $—S—$.

In another embodiment of this invention W is $—C(O)—$.

In another embodiment of this invention W is $—S(O)—$.

In another embodiment of this invention W is $—S(O)_2—$.

In another embodiment of this invention W is $—C(=NR^2)—$.

In another embodiment of this invention $G^1$ is $—N(R^2)_d—$, and W is $—C(O)—$.

In another embodiment of this invention $G^1$ is $—C(O)—$, and W is $—C(O)—$.

In another embodiment of this invention $G^1$ is $—S(O)—$, and W is $—C(O)—$.

In another embodiment of this invention $G^1$ is $—S(O)_2—$, and W is $—C(O)—$.

In another embodiment of this invention $G^1$ is $—C(=NR^2)—$, and W is $—C(O)—$.

In another embodiment of this invention $G^1$ is $—C(N(R^2)_2)—$ wherein each $R^2$ is independently selected, and W is $—C(O)—$.

In another embodiment of this invention $G^1$ is a direct bond, and W is $—C(O)—$.

In another embodiment of this invention $G^1$ is $—O—$, and W is $—C(O)—$.

In another embodiment of this invention $G^1$ is $—S—$, and W is $—C(O)—$.

In another embodiment of this invention $G^2$ is $—C(R^{21})_q—$, and W is $—C(O)—$.

In another embodiment of this invention $G^2$ is $—N(R^2)_d—$, and W is $—C(O)—$.

In another embodiment of this invention $G^2$ is $—C(O)—$, and W is $—C(O)—$.

In another embodiment of this invention $G^2$ is $—S(O)—$, and W is $—C(O)—$.

In another embodiment of this invention $G^2$ is $—S(O)_2—$, and W is $—C(O)—$.

In another embodiment of this invention $G^2$ is $—C(=NR^2)—$, and W is $—C(O)—$.

In another embodiment of this invention $G^2$ is $—C(N(R^2)_2)—$ wherein each $R^2$ is independently selected, and W is $—C(O)—$.

In another embodiment of this invention $G^2$ is a direct bond, and W is $—C(O)—$.

In another embodiment of this invention $G^2$ is $—O—$, and W is $—C(O)—$.

In another embodiment of this invention $G^2$ is $—S—$, and W is $—C(O)—$.

In another embodiment of this invention $G^5$ is $—CH—$.

In another embodiment of this invention $G^5$ is $—NH—$.

In another embodiment of this invention $G^5$ is $—N=$.

In another embodiment of this invention $G^5$ is $—O—$.

In another embodiment of this invention $G^5$ is $—S—$.

In another embodiment of this invention $G^5$ is $—S(O)—$.

In another embodiment of this invention $G^5$ is $—S(O)_2—$.

In another embodiment of this invention $G^6$ is C.

In another embodiment of this invention $G^6$ is CH.

In another embodiment of this invention $G^5$ is $—CH—$, and $G^6$ is C.

In another embodiment of this invention $G^5$ is $—NH—$, and $G^6$ is C.

In another embodiment of this invention $G^5$ is $—N=$, and $G^5$ is C.

In another embodiment of this invention $G^6$ is $—O—$, and $G^6$ is C.

In another embodiment of this invention $G^5$ is —S—, and $G^6$ is C.

In another embodiment of this invention $G^5$ is —S(O)—, and $G^6$ is C.

In another embodiment of this invention $G^5$ is —S(O)$_2$—, and $G^6$ is C.

In another embodiment of this invention $G^5$ is —CH—, and $G^6$ is CH.

In another embodiment of this invention $G^5$ is —NH—, and $G^6$ is CH.

In another embodiment of this invention $G^5$ is —N=, and $G^6$ is CH.

In another embodiment of this invention $G^5$ is —O—, and $G^6$ is CH.

In another embodiment of this invention $G^5$ is —S—, and $G^6$ is CH.

In another embodiment of this invention $G^5$ is —S(O)—, and $G^6$ is CH.

In another embodiment of this invention $G^5$ is —S(O)$_2$—, and $G^6$ is CH.

In another embodiment of this invention $G^7$ is a direct bond (i.e., $R^{10}$ is bound directly to $G^6$).

In another embodiment of this invention $G^7$ is —C(O)—.

In another embodiment of this invention $G^7$ is —(C=NR$^2$)—.

In another embodiment of this invention $G^7$ is —CHR$^3$—.

In another embodiment of this invention $G^7$ is C(R$^4$)$_2$.

In another embodiment of this invention $G^7$ is —CF$_2$—.

In another embodiment of this invention $G^7$ is —N(R$^2$)—.

In another embodiment of this invention $G^7$ is —O—.

In another embodiment of this invention $G^7$ is —S—.

In another embodiment of this invention $G^7$ is —S(O)$_t$.

In another embodiment of this invention $G^7$ is —CR$^4$(OH)—.

In another embodiment of this invention $G^7$ is —CR$^4$(OR$^4$)—.

In another embodiment of this invention $G^7$ is —C=C—.

In another embodiment of this invention $G^7$ is alkynyl.

In another embodiment of this invention $G^7$ is —(CH$_2$)$_r$N(R$^2$)—.

In another embodiment of this invention $G^7$ is —(CHR$^4$)$_r$N(R$^2$)—.

In another embodiment of this invention $G^7$ is —(C(R$^4$)$_2$)$_r$N(R$^2$)—.

In another embodiment of this invention $G^7$ is —N(R$^2$)(CH$_2$)$_r$—.

In another embodiment of this invention $G^7$ is —N(R$^2$)(CHR$^4$)$_r$—.

In another embodiment of this invention $G^7$ is —N(R$^2$)(C(R$^4$)$_2$)$_r$—.

In another embodiment of this invention $G^7$ is —(CH$_2$)$_r$—O—.

In another embodiment of this invention $G^7$ is —(CHR$^4$)$_r$—O—.

In another embodiment of this invention $G^7$ is —(C(R$^4$)$_2$)$_r$—O—.

In another embodiment of this invention $G^7$ is —O—(CH$_2$)$_r$—.

In another embodiment of this invention $G^7$ is —O—(CHR$^4$)$_r$—.

In another embodiment of this invention $G^7$ is —O—(C(R$^4$)$_2$)$_r$—.

In another embodiment of this invention $G^7$ is —C(O)NR$^5$—.

In another embodiment of this invention $G^7$ is —O—C(O)—.

In another embodiment of this invention $G^7$ is —C(O)—O—.

In another embodiment of this invention $G^7$ is —O—C(O)—NR$^5$—.

In another embodiment of this invention $G^7$ is —NR$^5$C(O)—.

In another embodiment of this invention $G^7$ is —(CH$_2$)$_r$NR$^5$—C(O)—.

In another embodiment of this invention $G^7$ is —(CHR$^4$)$_r$NR$^5$—C(O)—.

In another embodiment of this invention $G^7$ is —(C(R$^4$)$_2$)$_r$NR$^5$—C(O)—.

In another embodiment of this invention $G^7$ is —C(O)NR$^5$(CH$_2$)$_r$—.

In another embodiment of this invention $G^7$ is —C(O)NR$^5$(CHR$^4$)$_r$—.

In another embodiment of this invention $G^7$ is —C(O)NR$^5$(C(R$^4$)$_2$)$_r$—.

In another embodiment of this invention $G^7$ is —NR$^5$S(O)$_t$—.

In another embodiment of this invention $G^7$ is —(CH$_2$)$_r$NR$^5$S(O)$_t$.

In another embodiment of this invention $G^7$ is —(CHR$^4$)$_r$NR$^5$S(O)$_t$—.

In another embodiment of this invention $G^7$ is —(C(R$^4$)$_2$)$_r$NR$^5$S(O)$_t$—.

In another embodiment of this invention $G^7$ is —S(O)$_t$NR$^5$—.

In another embodiment of this invention $G^7$ is —S(O)$_t$NR$^5$(CH$_2$)$_r$—.

In another embodiment of this invention $G^7$ is —S(O)$_t$NR$^5$(CHR$^4$)$_r$—.

In another embodiment of this invention $G^7$ is —S(O)$_t$NR$^5$(C(R$^4$)$_2$)$_r$—.

In another embodiment of this invention $G^7$ is —NR$^5$—C(O)—O—.

In another embodiment of this invention $G^7$ is —NR$^5$—C(O)—NR$^5$—.

In another embodiment of this invention $G^7$ is —NR$^5$—S(O)$_t$NR$^5$—.

In another embodiment of this invention $G^7$ is —NR$^5$—C(=NR$^2$)—NR$^5$—.

In another embodiment of this invention $G^7$ is —NR$^5$—C(=NR$^2$)—O—.

In another embodiment of this invention $G^7$ is —O—C(=NR$^2$)—NR$^5$—.

In another embodiment of this invention $G^7$ is —C(R$^4$)=N—O—.

In another embodiment of this invention $G^7$ is —O—N=C(R$^4$)—.

In another embodiment of this invention $G^7$ is —O—C(R$^4$)=N—.

In another embodiment of this invention $G^7$ is —N=C(R$^4$)—O—.

In another embodiment of this invention $G^7$ is —(CH$_2$)$_2$—.

In another embodiment of this invention $G^7$ is —(C(R$^4$)$_2$)$_2$—.

In another embodiment of this invention $G^7$ is —(CHR$^4$)$_2$—.

In another embodiment of this invention $G^7$ is —(CH$_2$)$_3$—.

In another embodiment of this invention $G^7$ is —(C(R$^4$)$_2$)$_3$—.

In another embodiment of this invention $G^7$ is —(CHR$^4$)$_3$—.

In another embodiment of this invention $G^7$ is cycloalkyl.

In another embodiment of this invention $G^7$ is heterocycloalkyl.

In another embodiment of this invention t is 1.
In another embodiment of this invention t is 2.
In another embodiment of this invention r is 1.
In another embodiment of this invention r is 2.
In another embodiment of this invention r is 3.
In another embodiment of this invention Ring (E) is a five membered heteroaryl ring.
In another embodiment of this invention Ring (E) is a six membered heteroaryl ring.
In another embodiment of this invention Ring (E) is a five membered heterocycloalkyl ring.
In another embodiment of this invention Ring (E) is a six membered heterocycloalkyl ring.
In another embodiment of this invention Ring (E) is a five membered heterocycloalkenyl ring,
In another embodiment of this invention Ring (E) is a six membered heterocycloalkenyl ring.
In another embodiment of this invention Ring (F) is a five membered heteroaryl ring.
In another embodiment of this invention Ring (F) is a six membered heteroaryl ring.
In another embodiment of this invention Ring (F) is a five membered heterocycloalkyl ring.
In another embodiment of this invention Ring (F) is a six membered heterocycloalkyl ring.
In another embodiment of this invention Ring (F) is a five membered heterocycloalkenyl ring.
In another embodiment of this invention Ring (F) is a six membered heterocycloalkenyl ring.
In another embodiment of this invention $G^5$ is —CH—, and $G^6$ is C, and Ring (E) or Ring (F) is a five membered heteroaryl ring.
In another embodiment of this invention $G^5$ is —NH—, and $G^6$ is C, and Ring (E) or Ring (F) is a five membered heteroaryl ring.
In another embodiment of this invention $G^5$ is —N═, and $G^6$ is C, and Ring (E) or Ring (F) is a five membered heteroaryl ring.
In another embodiment of this invention $G^5$ is —O—, and $G^6$ is C, and Ring (E) or Ring (F) is a five membered heteroaryl ring.
In another embodiment of this invention $G^5$ is —S—, and $G^6$ is C, and Ring (E) or Ring (F) is a five membered heteroaryl ring.
In another embodiment of this invention $G^5$ is —S(O)—, and $G^6$ is C, and Ring (E) or Ring (F) is a five membered heteroaryl ring.
In another embodiment of this invention $G^5$ is —S(O)$_2$—, and $G^6$ is C, and Ring (E) or Ring (F) is a five membered heteroaryl ring.
In another embodiment of this invention $G^5$ is —CH—, and $G^6$ is C, and Ring (E) or Ring (F) is a six membered heteroaryl ring.
In another embodiment of this invention $G^5$ is —NH—, and $G^6$ is C, and Ring (E) or Ring (F) is a six membered heteroaryl ring.
In another embodiment of this invention $G^5$ is —N═, and $G^6$ is C, and Ring (E) or Ring (F) is a six membered heteroaryl ring.
In another embodiment of this invention $G^5$ is —O—, and $G^6$ is C, and Ring (E) or Ring (F) is a six membered heteroaryl ring.
In another embodiment of this invention $G^5$ is —S—, and $G^6$ is C, and Ring (E) or Ring (F) is a six membered heteroaryl ring.
In another embodiment of this invention $G^5$ is —S(O)—, and $G^6$ is C, and Ring (E) or Ring (F) is a six membered heteroaryl ring.
In another embodiment of this invention $G^5$ is —S(O)$_2$—, and $G^6$ is C, and Ring (E) or Ring (F) is a six membered heteroaryl ring.
In another embodiment of this invention $G^5$ is —CH—, and $G^6$ is CH, and Ring (E) or Ring (F) is a five membered heterocycloalkyl ring.
In another embodiment of this invention $G^5$ is —NH—, and $G^6$ is CH, and Ring (E) or Ring (F) is a five membered heterocycloalkyl ring.
In another embodiment of this invention $G^5$ is —N═, and $G^6$ is CH, and Ring (E) or Ring (F) is a five membered heterocycloalkyl ring.
In another embodiment of this invention $G^5$ is —O—, and $G^6$ is CH, and Ring (E) or Ring (F) is a five membered heterocycloalkyl ring.
In another embodiment of this invention $G^5$ is —S—, and $G^6$ is CH, and Ring (E) or Ring (F) is a five membered heterocycloalkyl ring.
In another embodiment of this invention $G^5$ is —S(O)—, and $G^6$ is CH, and Ring (E) or Ring (F) is a five membered heterocycloalkyl ring.
In another embodiment of this invention $G^5$ is —S(O)$_2$—, and $G^6$ is CH, and Ring (E) or Ring (F) is a five membered heterocycloalkyl ring.
In another embodiment of this invention $G^5$ is —CH—, and $G^6$ is CH, and Ring (E) or Ring (F) is a six membered heterocycloalkyl ring.
In another embodiment of this invention $G^5$ is —NH—, and $G^6$ is CH, and Ring (E) or Ring (F) is a six membered heterocycloalkyl ring,
In another embodiment of this invention $G^5$ is —N═, and $G^6$ is CH, and Ring (E) or Ring (F) is a six membered heterocycloalkyl ring.
In another embodiment of this invention $G^5$ is —O—, and $G^6$ is CH, and Ring (E) or Ring (F) is a six membered heterocycloalkyl ring.
In another embodiment of this invention $G^5$ is —S—, and $G^6$ is CH, and Ring (E) or Ring (F) is a six membered heterocycloalkyl ring.
In another embodiment of this invention $G^5$ is —S(O)—, and $G^6$ is CH, and Ring (E) or Ring (F) is a six membered heterocycloalkyl ring.
In another embodiment of this invention $G^5$ is —S(O)$_2$—, and $G^6$ is CH, and Ring (E) or Ring (F) is a six membered heterocycloalkyl ring.
In another embodiment of this invention $G^5$ is —CH—, and $G^6$ is CH.
In another embodiment of this invention $G^5$ is —NH—, and $G^6$ is CH.
In another embodiment of this invention $G^5$ is —N═, and $G^6$ is CH.
In another embodiment of this invention $G^5$ is —O—, and $G^6$ is CH.
In another embodiment of this invention $G^5$ is —S—, and $G^6$ is CH.
In another embodiment of this invention $G^5$ is —S(O)—, and $G^6$ is CH.
In another embodiment of this invention $G^5$ is —S(O)$_2$—, and $G^6$ is CH.
Other embodiments of this invention are directed to compounds of formula (IA) wherein $G^5$, $G^6$ and $G^7$ are as described in any of the above embodiments directed to $G^5$, $G^6$ and $G^7$.

Other embodiments of this invention are directed to compounds of formula (IB) wherein $G^5$, $G^6$ and $G^7$ are as described in any of the above embodiments directed to $G^5$, $G^6$ and $G^7$.

In another embodiment of this invention $R^{21}$ is selected from the group consisting of: alkyl, —$OR^{15}$, —$C(O)OR^{15}$, —$C(O)NR^{15}R^{16}$, and alkyl substituted with 1 to 5 independently selected $R^{22}$ groups (e.g., halo, such as, for example, F, Cl, and Br).

In another embodiment of this invention $R^{21}$ is selected from the group consisting of: alkyl, —$OR^{15}$, —$C(O)OR^{15}$, —$C(O)NR^{15}R^{16}$, and alkyl substituted with 1 to 5 independently selected $R^{22}$ groups (e.g., halo, such as, for example, F, Cl, and Br, and wherein in one example the alkyl substituted $R^{21}$ group is —$CF_3$), wherein $R^{15}$ and $R^{16}$ are independently selected from the group consisting of: H, alkyl, $(R^{18})_n$-arylalkyl- (wherein, for example, n is 1, and $R^{18}$ is —$OR^{20}$, and $R^{20}$ is alkyl (e.g., methyl), cycloalkyl (e.g., cyclobutyl), and $(R^{18})_n$-alkyl (e.g., n is 1, $R^{18}$ is —$OR^{20}$, and $R^{20}$ is alkyl (e.g., methyl).

In another embodiment of this invention $R^{21}$ is selected from the group consisting of: (a) alkyl, —$OR^{16}$ (wherein $R^{15}$ is alkyl, e.g., methyl and ethyl), (b) —$C(O)OR^{15}$ (wherein $R^{15}$ is alkyl, e.g., methyl), (c) —$C(O)NR^{15}R^{16}$ (wherein $R^{15}$ and $R^{16}$ are independently selected from the group consisting of: H, alkyl, $(R^{18})_n$-arylalkyl- (wherein, for example, n is 1, and $R^{18}$ is —$OR^{20}$, and $R^{20}$ is alkyl (e.g., methyl), cycloalkyl (e.g., cyclobutyl), and $(R^{18})_n$-alkyl (e.g., n is 1, $R^{18}$ is —$OR^{20}$, and $R^{20}$ is alkyl (e.g., methyl), and in one example, only one of $R^{15}$ and $R^{16}$ is H), and (d) alkyl substituted with 1 to 5 independently selected $R^{22}$ groups (e.g., halo, such as, for example, F, Cl, and Br, and wherein in one example the alkyl substituted $R^{21}$ group is —$CF_3$).

In one embodiment of this invention $R^{10}$ is selected from the group consisting of: aryl- (e.g., phenyl), heteroaryl- (e.g., pyridyl), cycloalkyl-, cycloalkenyl, cycloalkylalkyl-, heterocyclyl-, heterocyclenyl-, heterocyclylalkyl-, heterocyclyalkenyl-, fused benzocycloalkyl- (i.e., benzofusedcycloalkyl-), fused benzoheterocycloalkyl- (i.e., benzofusedheterocycloalkyl-), fused heteroarylcycloalkyl- (i.e., heteroarylfusedcycloalkyl-), fused heteroarylheterocycloalkyl- (i.e., heteroarylfusedheterocycloalkyl-), fused cycloalkylaryl (i.e., cycloalkyfusedlaryl-), fused heterocycloalkylaryl- (i.e., heterocycloalkylfusedaryl-), fused cycloalkylheteroaryl- (i.e., cycloalkylfusedheteroaryl-), and fused heterocycloalkylheteroaryl- (i.e., heterocycloalkylfusedheteroaryl-), and wherein each of said $R^{10}$ moieties is optionally substituted with 1-5 independently selected $R^{21}$ groups.

In another embodiment of this invention $R^{10}$ is selected from the group consisting of:

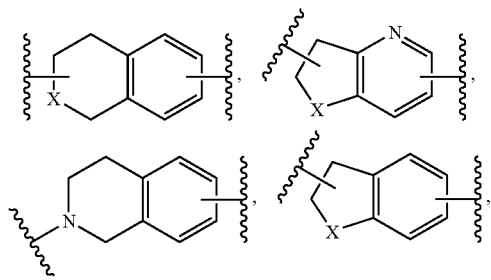

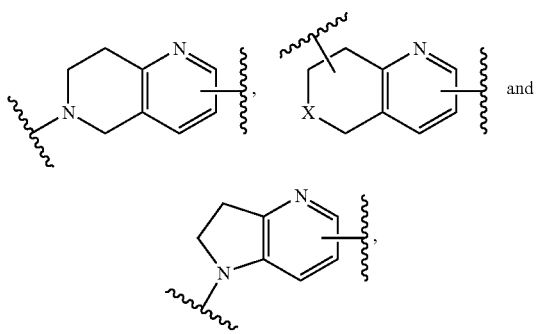

wherein X is selected from the group consisting of: O, —$N(R^{14})$— and —S—; and wherein each of said $R^{10}$ moieties is optionally substituted with 1-5 independently selected $R^{21}$ groups.

In another embodiment of this invention $R^{10}$ is selected from the group consisting of:

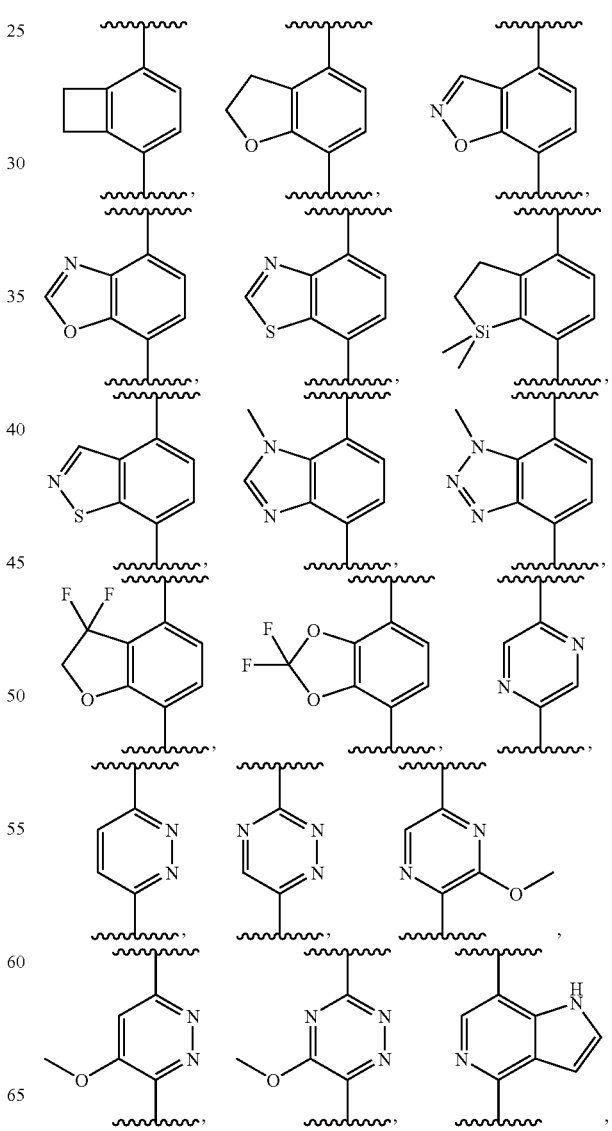

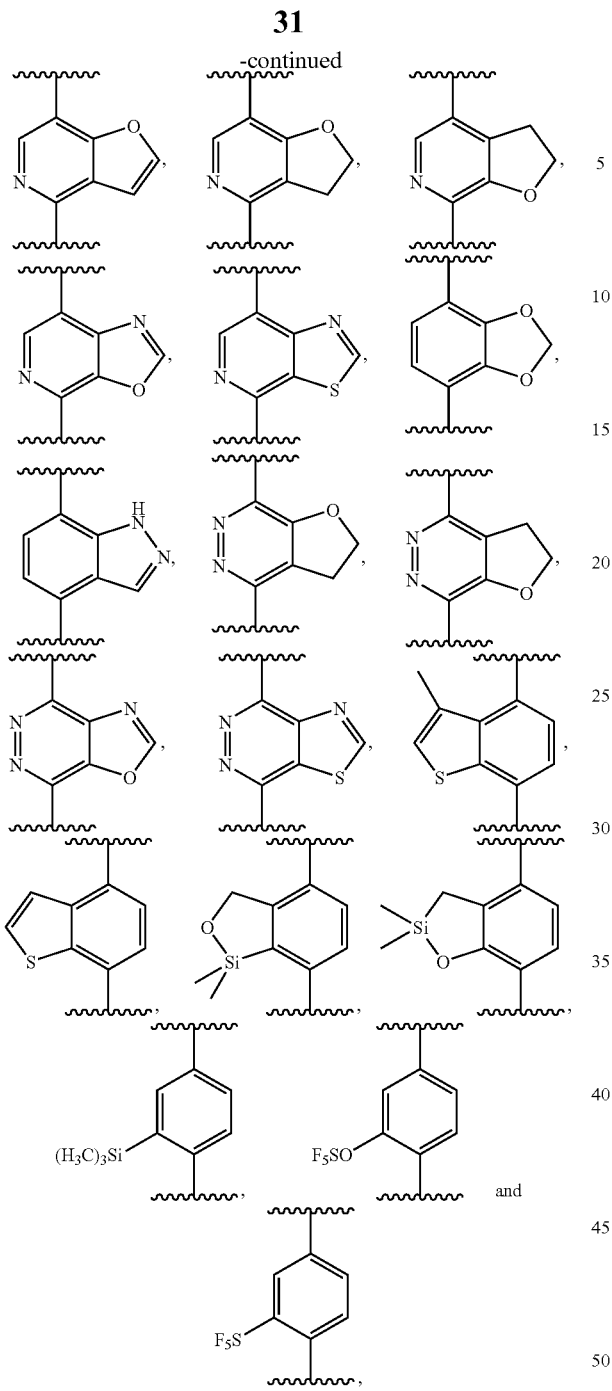
wherein each of said R[10] moieties is optionally substituted with 1-5 independently selected R[21] groups.
In another embodiment of this invention R[10] in formula (I) is selected from the group consisting of:
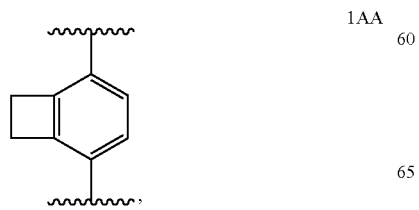
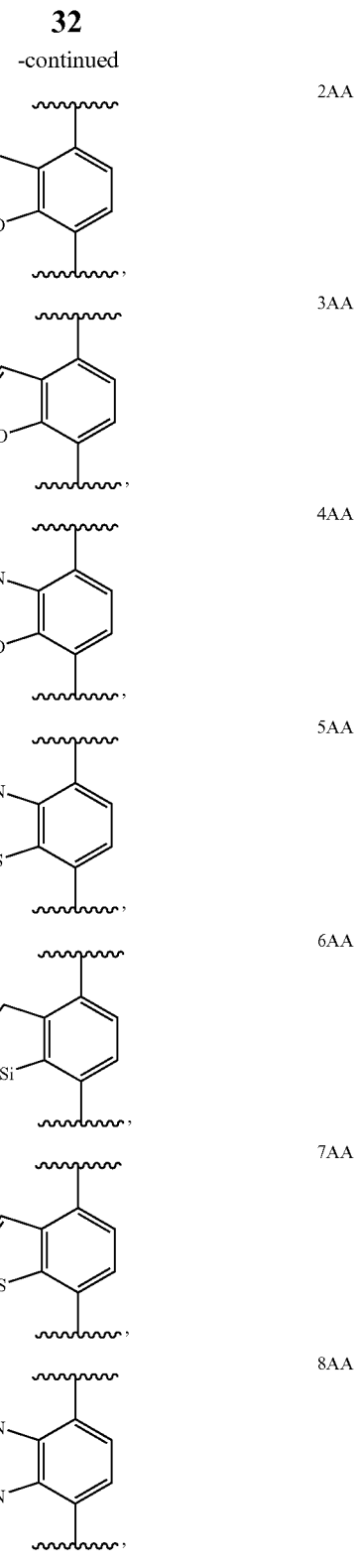
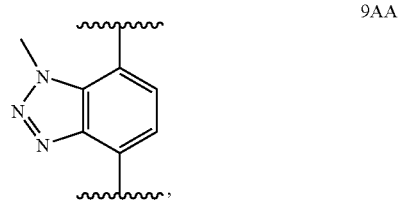

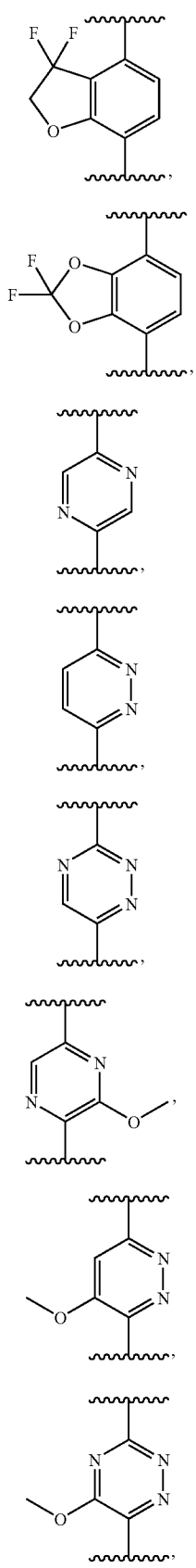
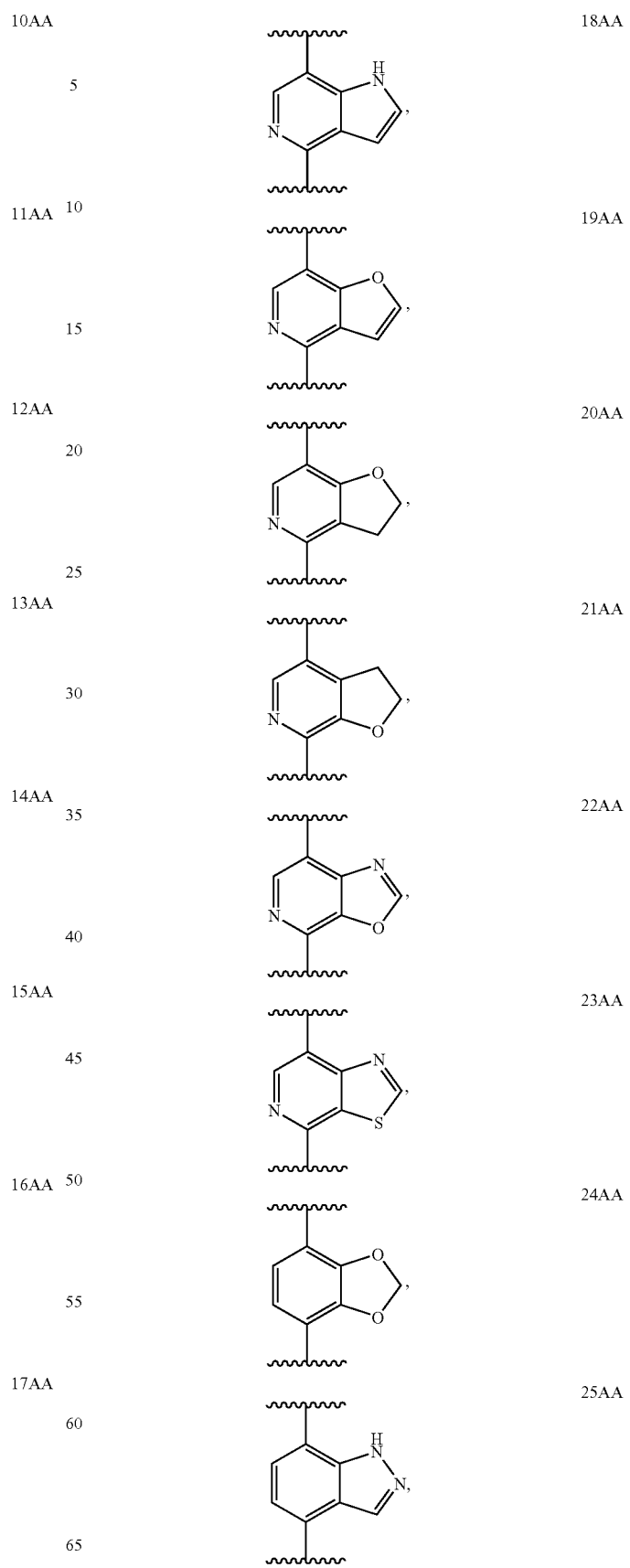

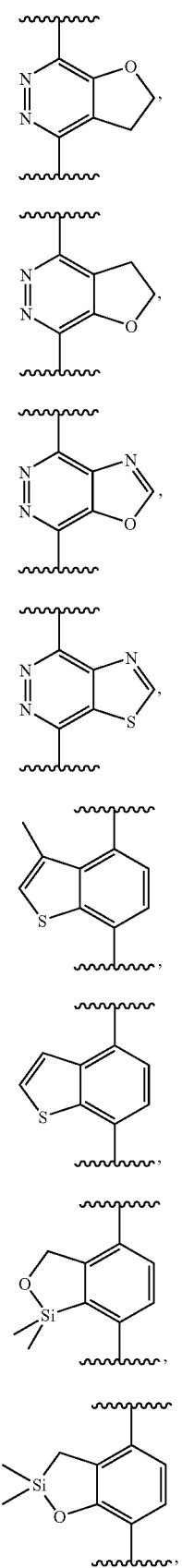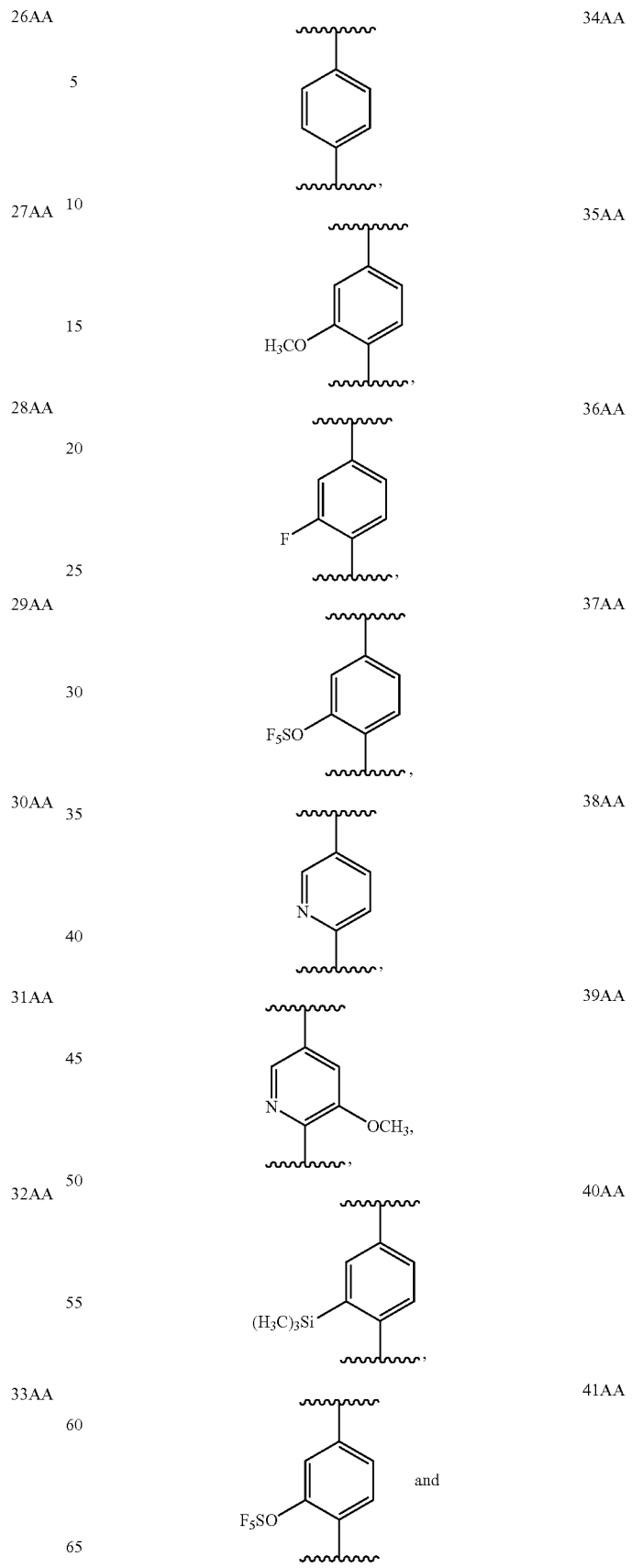

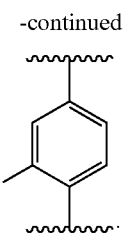
42AA

In another embodiment of this invention R¹⁰ is group 1AA. In another embodiment of this invention R¹⁰ is group 2AA. In another embodiment of this invention R¹⁰ is group 3AA. In another embodiment of this invention R¹⁰ is group 4AA. In another embodiment of this invention R¹⁰ is group 5AA. In another embodiment of this invention R¹⁰ is group 6AA. In another embodiment of this invention R¹⁰ is group 7AA. In another embodiment of this invention R¹⁰ is group 5AA. In another embodiment of this invention R¹⁰ is group 9AA. In another embodiment of this invention R¹⁰ is group 10AA. In another embodiment of this invention R¹⁰ is group 11AA. In another embodiment of this invention R¹⁰ is group 12AA. In another embodiment of this invention R¹⁰ is group 13AA. In another embodiment of this invention R¹⁰ is group 14AA. In another embodiment of this invention R¹⁰ is group 15AA. In another embodiment of this invention R¹⁰ is group 16AA. In another embodiment of this invention R¹⁰ is group 17AA. In another embodiment of this invention R¹⁰ is group 18AA. In another embodiment of this invention R¹⁰ is group 19AA. In another embodiment of this invention R¹⁰ is group 20AA. In another embodiment of this invention R¹⁰ is group 21AA. In another embodiment of this invention R¹⁰ is group 22AA. In another embodiment of this invention R¹⁰ is group 23AA. In another embodiment of this invention R¹⁰ is group 24AA. In another embodiment of this invention R¹⁰ is group 25AA. In another embodiment of this invention R¹⁰ is group 26AA. In another embodiment of this invention R¹⁰ is group 27AA. In another embodiment of this invention R¹⁰ is group 28AA. In another embodiment of this invention R¹⁰ is group 29AA. In another embodiment of this invention R¹⁰ is group 30AA. In another embodiment of this invention R¹⁰ is group 31AA. In another embodiment of this invention R¹⁰ is group 32AA. In another embodiment of this invention R¹⁰ is group 33AA. In another embodiment of this invention R¹⁰ is group 34AA. In another embodiment of this invention R¹⁰ is group 35AA. In another embodiment of this invention R¹⁰ is group 36AA. In another embodiment of this invention R¹⁰ is group 37AA. In another embodiment of this invention R¹⁰ is group 38AA. In another embodiment of this invention R¹⁰ is group 39A. In another embodiment of this invention R¹⁰ is group 40AA. In another embodiment of this invention R¹⁰ is group 41AA. In another embodiment of this invention R¹⁰ is group 42AA.

In another embodiment of this invention R¹⁰ is aryl.

In another embodiment of this invention R¹⁰ aryl is aryl and said aryl is phenyl.

In another embodiment of this invention R¹⁰ is aryl substituted with one or more R²¹ groups.

In another embodiment of this invention R¹⁰ is aryl substituted with one or more R²¹ groups, and said aryl is phenyl, i.e., said R¹⁰ group is phenyl substituted with one or more R²¹ groups.

In another embodiment of this invention R¹⁰ is phenyl substituted with one or more R²¹ groups, and each R²¹ group is the same or different —OR¹⁵ group.

In another embodiment of this invention R¹⁰ is phenyl substituted with one or more R²¹ groups, and each R²¹ group is the same or different —OR¹⁵ group, and said R¹⁵ is alkyl, and each alkyl is independently selected.

In another embodiment of this invention R¹⁰ is phenyl substituted with one R²¹ group, and said R²¹ group is —OR¹⁵, and said R¹⁵ is alkyl.

In another embodiment of this invention R¹⁰ is phenyl substituted with one R²¹ group, and said R²¹ group is —OR¹⁵, and said R¹⁵ is alkyl, and said alkyl is methyl.

In another embodiment of this invention R¹⁰ is phenyl substituted with one or more (e.g., one or two, or one) independently selected R²¹ halo groups.

In another embodiment of this invention R¹⁰ is phenyl substituted with one R²¹ group, and said R²¹ group is halo.

In another embodiment of this invention R¹⁰ is phenyl substituted with one R²¹ group, and said R²¹ group is F.

In another embodiment of this invention R¹⁰ is phenyl substituted with one R²¹ group and said R²¹ is an —OR¹⁵ group, and R¹⁵ is an (R¹⁸)ₙalkyl group, and R¹⁸ is halo, and it is 1 to 3, and each halo is independently selected.

In another embodiment of this invention R¹⁰ is phenyl substituted with one R²¹ group and said R²¹ is an —OR¹⁵ group, and R¹⁵ is an (R¹⁸)ₙalkyl group, and R¹⁸ is F, and n is 3.

In another embodiment of this invention R¹⁰ is phenyl substituted with one R²¹ group and said R²¹ is an —OR¹⁵ group, and R¹⁵ is an (R¹⁸)ₙalkyl group, and R¹⁸ is F, and n is 3, and the alkyl is methyl (i.e., the R²¹ substituent is —OCF₃).

In another embodiment of this invention R¹⁰ is heteroaryl.

In another embodiment of this invention R¹⁰ is heteroaryl substituted with one or more R²¹ groups.

In another embodiment of this invention R⁹ is selected from the group consisting of:

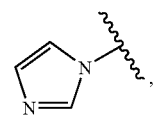
1gg

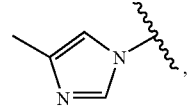
2gg

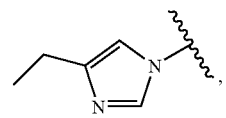
3gg

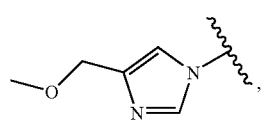
4gg

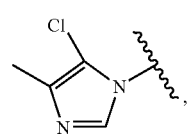
5gg

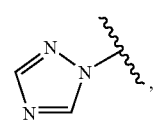
6gg

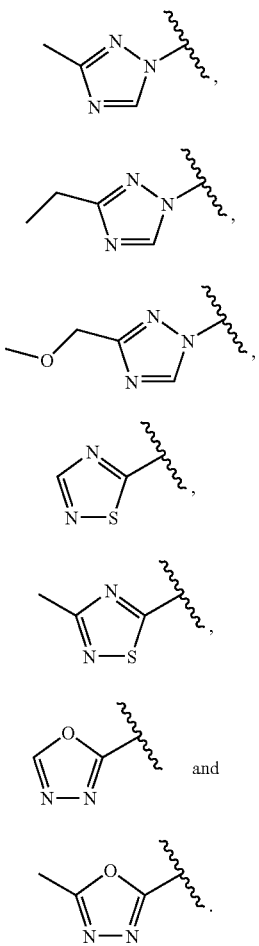
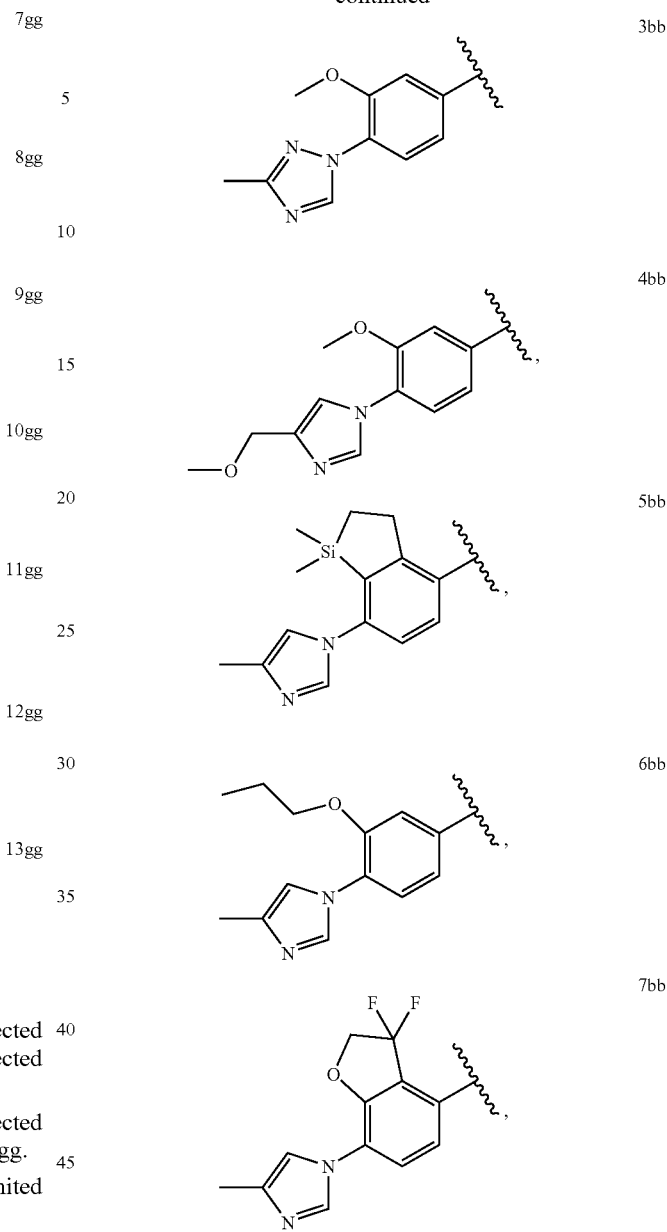
In another embodiment of this invention $R^{10}$ is selected from the group consisting of 1AA to 42AA, and $R^9$ is selected from the group consisting of 1gg to 13gg.
In another embodiment of this invention $R^{10}$ is selected from the group consisting of 1AA to 42AA, and $R^9$ is 2gg.
Examples of the $R^9$-$R^{10}$-moiety include, but are not limited to:
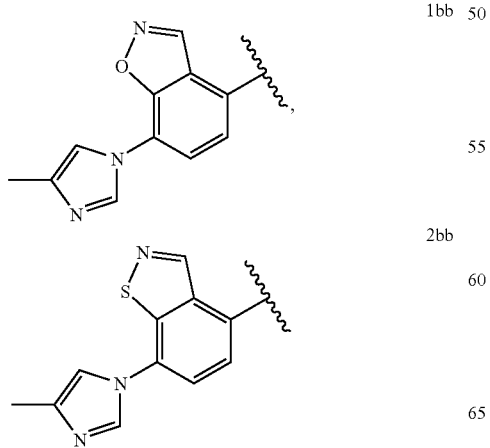
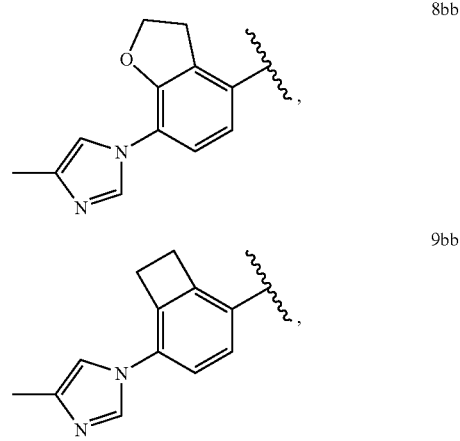

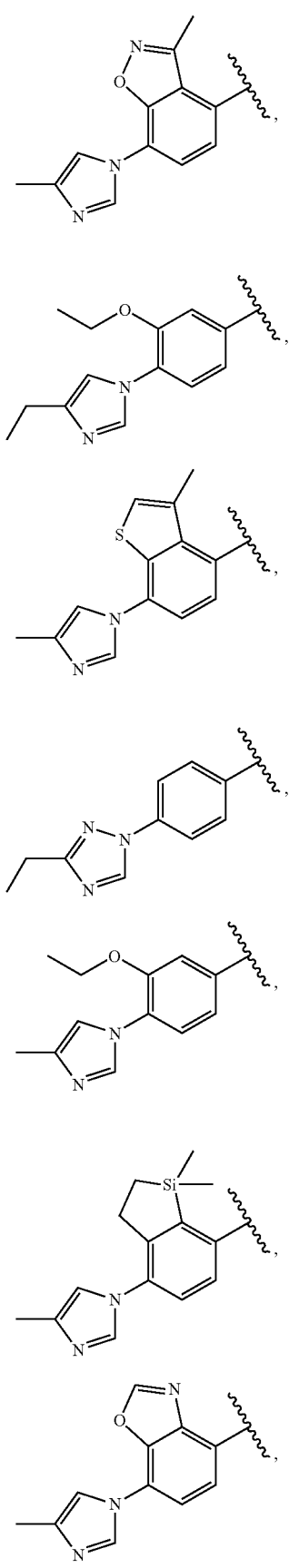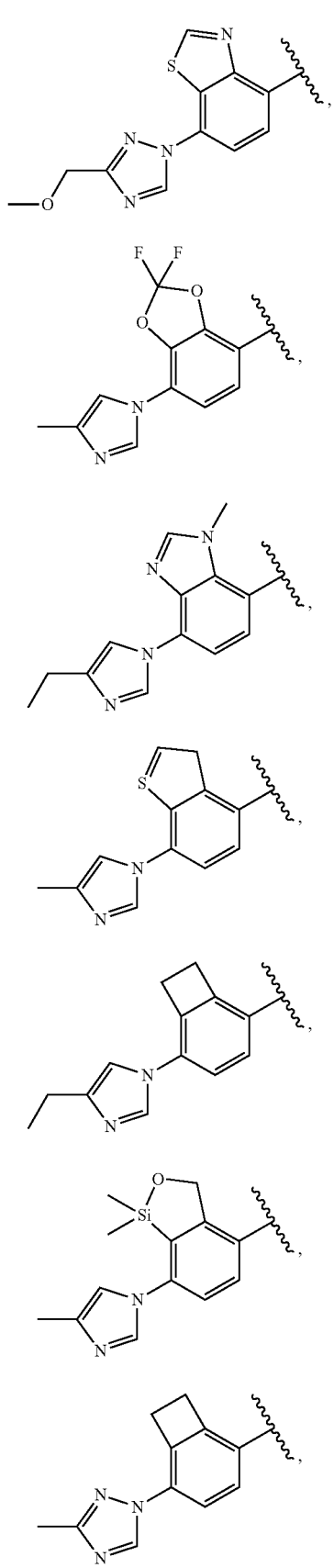

24bb
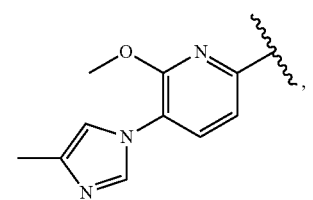
25bb
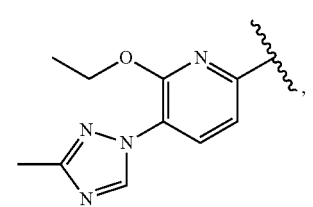
26bb
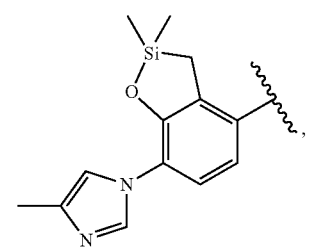
27bb
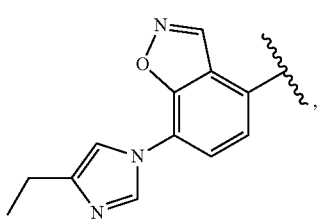
28bb
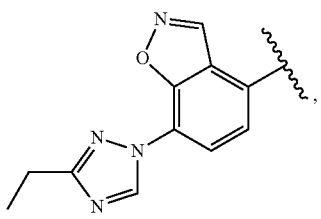
29bb
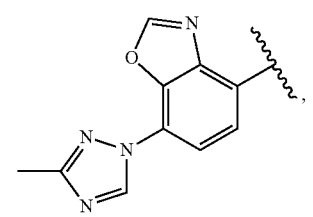
30bb
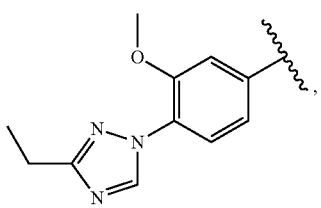
31bb
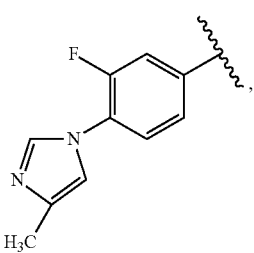
32bb
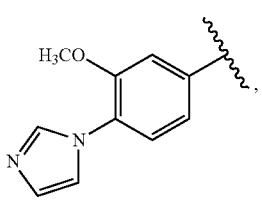
33bb
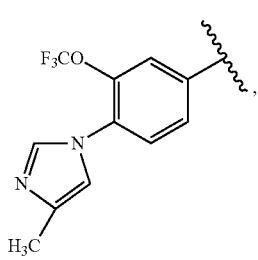
34bb
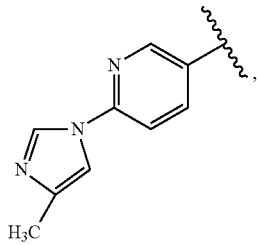
35bb
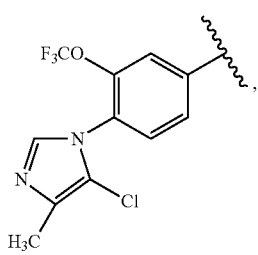
36bb

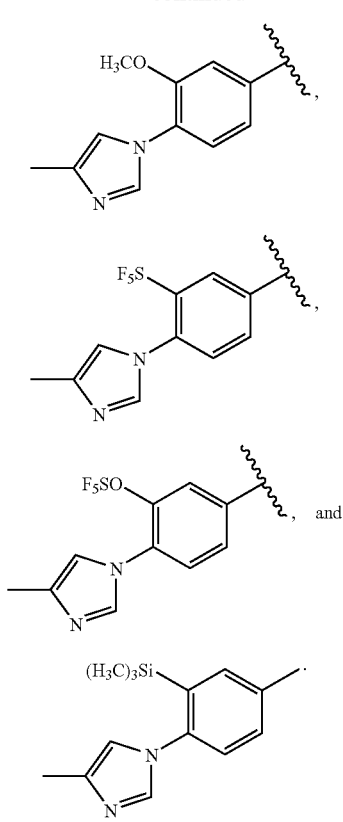

37bb

38bb

39bb, and

40bb.

In another embodiment the $R^9$-$R^{10}$-moiety is 1bb. In another embodiment the $R^9$-$R^{10}$-moiety is 2bb. In another embodiment the $R^9$-$R^{10}$-moiety is 3bb. In another embodiment the $R^9$-$R^{10}$-moiety is 4bb. In another embodiment the $R^9$-$R^{10}$-moiety is 5bb. In another embodiment the $R^9$-$R^{10}$-moiety is ebb. In another embodiment the $R^9$-$R^{10}$-moiety is 7bb. In another embodiment the $R^9$-$R^{10}$-moiety is ebb. In another embodiment the $R^9$-$R^{10}$-moiety is 9bb. In another embodiment the $R^9$-$R^{10}$-moiety is 10bb. In another embodiment the $R^9$-$R^{10}$-moiety is 11 bb. In another embodiment the $R^9$-$R^{10}$-moiety is 12bb. In another embodiment the $R^9$-$R^{10}$-moiety is 13bb. In another embodiment the $R^9$-$R^{10}$-moiety is 14bb. In another embodiment the $R^9$-$R^{10}$-moiety is 15bb. In another embodiment the $R^9$-$R^{10}$-moiety is 16bb. In another embodiment the $R^9$-$R^{10}$-moiety is 17bb. In another embodiment the $R^9$-$R^{10}$-moiety is 18bb. In another embodiment the $R^9$-$R^{10}$-moiety is 19bb. In another embodiment the $R^9$-$R^{10}$-moiety is 20bb. In another embodiment the $R^9$-$R^{10}$-moiety is 21 bb. In another embodiment the $R^9$-$R^{10}$-moiety is 22bb. In another embodiment the $R^9$-$R^{10}$-moiety is 23bb. In another embodiment the $R^9$-$R^{10}$-moiety is 24bb. In another embodiment the $R^9$-$R^{10}$-moiety is 25bb. In another embodiment the $R^9$-$R^{10}$-moiety is 26bb. In another embodiment the $R^9$-$R^{10}$-moiety is 27bb. In another embodiment the $R^9$-$R^{10}$-moiety is 28bb. In another embodiment the $R^9$-$R^{10}$-moiety is 29bb. In another embodiment the $R^9$-$R^{10}$-moiety is 30bb. In another embodiment the $R^9$-$R^{10}$-moiety is 31 bb. In another embodiment the $R^9$-$R^{10}$-moiety is 32bb. In another embodiment the $R^9$-$R^{10}$-moiety is 33bb. In another embodiment the $R^9$-$R^{10}$-moiety is 34bb. In another embodiment the $R^9$-$R^{10}$-moiety is 35bb. In another embodiment the $R^9$-$R^{10}$-moiety is 36bb. In another embodiment the $R^9$-$R^{10}$-moiety is 37bb. In another embodiment the $R^9$-$R^{10}$-moiety is 38bb. In another embodiment the $R^9$-$R^{10}$-moiety is 39bb. In another embodiment the $R^9$-$R^{10}$-moiety is 40bb.

In another embodiment of this invention $R^9$ is heteroaryl.

In another embodiment of this invention $R^9$ is heteroaryl substituted with one or more $R^{21}$ groups.

In another embodiment of this invention $R^9$ is heteroaryl substituted with one or more $R^{21}$ groups, and said $R^{21}$ groups are the same or different alkyl.

In another embodiment of this invention $R^9$ is heteroaryl substituted with one $R^{21}$ group, and said $R^{21}$ is alkyl.

In another embodiment of this invention $R^9$ is heteroaryl substituted with one $R^{21}$ group, and said $R^{21}$ is alkyl, and said alkyl is methyl.

In another embodiment of this invention $R^9$ is and said heteroaryl is imidazoyl.

In another embodiment of this invention $R^9$ is imidazolyl substituted with one or more $R^{21}$ groups.

In another embodiment of this invention $R^9$ is imidazolyl substituted with one or more $R^{21}$ groups, and said $R^{21}$ groups are the same or different alkyl.

In another embodiment of this invention $R^9$ is imidazolyl substituted with one $R^{21}$ group, and said $R^{21}$ is alkyl.

In another embodiment of this invention $R^9$ is imidazolyl substituted with one $R^{21}$ group, and said $R^{21}$ is alkyl, and said alkyl is methyl.

In another embodiment of this invention $R^{10}$ is selected from the group consisting of aryl and aryl substituted with one or more $R^{21}$ groups, and said $R^9$ group is selected from the group consisting of heteroaryl and heteroaryl substituted with one or more $R^{21}$ groups, wherein each $R^{21}$ is independently selected.

In another embodiment of this invention $R^{10}$ is phenyl substituted with one or more $R^{21}$ groups, and said $R^9$ is imidazolyl substituted with one or more $R^{21}$ groups, wherein each $R^{21}$ is independently selected.

In another embodiment of this invention $R^{10}$ is phenyl substituted with one $R^{21}$ group, and said $R^9$ is imidazolyl substituted with one $R^{21}$ group, wherein each $R^{21}$ is independently selected.

In another embodiment of this invention $R^{10}$ is phenyl substituted with one or more independently selected —$OR^{15}$ groups, and said $R^9$ is imidazolyl substituted with one or more independently selected alkyl groups.

In another embodiment of this invention $R^{10}$ is phenyl substituted with one or more independently selected —$OR^{15}$ groups, and said $R^9$ is imidazolyl substituted with one or more independently selected alkyl groups, and each $R^{15}$ is the same or different alkyl group.

In another embodiment of this invention $R^{10}$ is phenyl substituted with one —$OR^{15}$ group, and said $R^9$ is imidazolyl substituted with one alkyl group.

In another embodiment of this invention $R^{10}$ is phenyl substituted with one —$OR^{15}$ group, and said $R^9$ is imidazolyl substituted with one alkyl group, and $R^{15}$ is alkyl, and wherein the $R^{15}$ alkyl group, and the alkyl group on said imidazolyl are independently selected.

In another embodiment of this invention $R^{10}$ is phenyl substituted with one —$OR^{15}$ group, and said $R^9$ is imidazolyl substituted with one methyl group, and $R^{15}$ is methyl, and wherein the $R^{15}$ alkyl group, and the alkyl group on said imidazolyl are independently selected.

In another embodiment of this invention the R⁹—R¹⁰-moiety is:

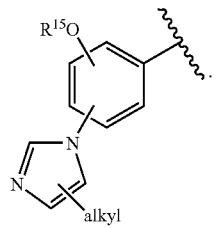

In another embodiment of this invention the R⁹-R¹⁰-moiety is:

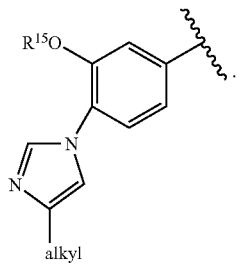

In another embodiment of this invention the R⁹-R¹⁰-moiety is:

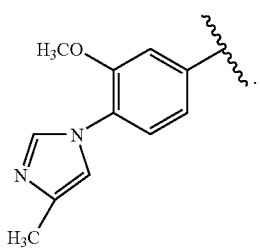

In another embodiment of this invention the R⁹-R¹⁰-moiety is:

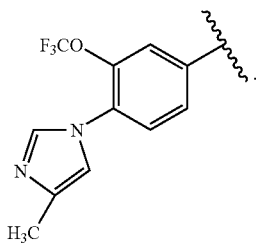 [SMILES: *c1ccc(-n2cnc(C)c2)c(OC(F)(F)F)c1]

In another embodiment of this invention the R⁹-R¹⁰-moiety is:

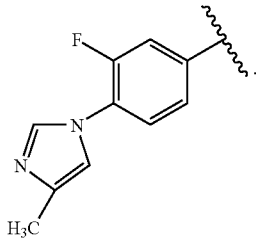 [SMILES: *c1ccc(-n2cnc(C)c2)c(F)c1]

In another embodiment of this invention the R⁹-R¹⁰-moiety is:

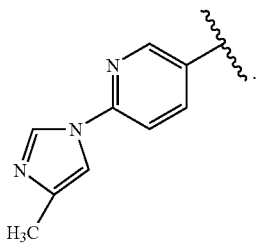 [SMILES: *c1ccc(-n2cnc(C)c2)nc1]

In another embodiment of this invention $R^1$ is an alkyl group substituted with one or more independently selected $R^{21}$ groups.

In another embodiment of this invention $R^1$ is:

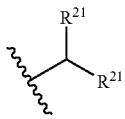

wherein each $R^{21}$ is independently selected, and each $R^{21}$ is independently unsubstituted or substituted with one or more independently selected $R^{22}$ groups.

In another embodiment of this invention $R^1$ is:

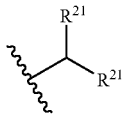

wherein one $R^{21}$ is an unsubstituted or substituted alkyl group.

In another embodiment of this invention $R^1$ is:

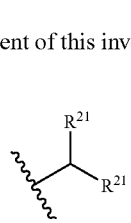

wherein one $R^{21}$ is an unsubstituted alkyl group.

In another embodiment of this invention $R^1$ is:

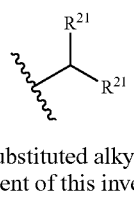

wherein one $R^{21}$ is a substituted alkyl group.

In another embodiment of this invention $R^1$ is:

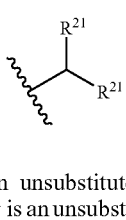

wherein one $R^{21}$ is an unsubstituted or substituted alkyl group, and the other $R^{21}$ is an unsubstituted or substituted aryl (e.g., phenyl) group.

In another embodiment of this invention $R^1$ is:

$$\begin{array}{c} CH_2OH \\ | \\ {\sim}{\sim}{-}C{-}R^{21} \\ | \\ {\sim}{\sim} \end{array}$$

and $R^{21}$ is unsubstituted or substituted with one or more independently selected $R^{22}$ groups.

In another embodiment of this invention $R^1$ is:

$$\begin{array}{c} CH_2OH \\ | \\ {\sim}{\sim}{-}C{-}R^{21} \\ | \\ {\sim}{\sim} \end{array}$$

and $R^{21}$ is unsubstituted aryl (e.g., phenyl) or aryl (e.g., phenyl) substituted with one or more independently selected $R^{22}$ groups.

In another embodiment of this invention $R^1$ is an alkyl group substituted with one $R^{21}$ group.

In another embodiment of this invention $R^1$ is an alkyl group substituted with one $R^{21}$ group, and said $R^{21}$ group is substituted with one or more independently selected $R^{22}$ groups.

In another embodiment of this invention $R^1$ is:

$$\begin{array}{c} \\ | \\ {\sim}{\sim}{-}C{-}R^{21} \\ | \\ {\sim}{\sim} \end{array}$$

wherein $R^{21}$ is unsubstituted or substituted with one or more independently selected $R^{22}$ groups.

In another embodiment of this invention $R^1$ is an alkyl group substituted with one $R^{21}$ group, and said $R^{21}$ group is an aryl group.

In another embodiment of this invention $R^1$ is an alkyl group substituted with one $R^{21}$ group, and said $R^{21}$ group is an aryl group, said aryl is phenyl.

In another embodiment of this invention $R^1$ is an ethyl group substituted with one $R^{21}$ group, and said $R^{21}$ group is an aryl group, said aryl is phenyl.

In another embodiment of this invention $R^1$ is an methyl group substituted with one $R^{21}$ group, and said $R^{21}$ group is an aryl group, said aryl is phenyl.

In another embodiment of this invention $R^1$ is an alkyl group substituted with one $R^{21}$ group, and said $R^{21}$ group is an aryl group, and said aryl group is substituted with one or more independently selected $R^{22}$ groups.

In another embodiment of this invention $R^1$ is an alkyl group substituted with one $R^{21}$ group, and said $R^{21}$ group is an aryl group, and said aryl group is substituted with one or more $R^{22}$ groups, and each $R^{22}$ group is the same or different halo.

In another embodiment of this invention $R^1$ is an alkyl group substituted with one $R^{21}$ group, and said $R^{21}$ group is an aryl group, and said aryl group is substituted with 1 to 3 $R^{22}$ groups, and each $R^{22}$ group is the same or different halo.

In another embodiment of this invention $R^1$ is an alkyl group substituted with one $R^{21}$ group, and said $R^{21}$ group is an aryl group, and said aryl group is substituted with one or two $R^{22}$ halo groups, and each $R^{22}$ group is the same or different halo, In another embodiment of this invention $R^1$ is an alkyl group substituted with one $R^{21}$ group, and said $R^{21}$ group is an aryl group, and said aryl group is substituted with one or two $R^{22}$ F groups.

In another embodiment of this invention $R^1$ is an alkyl group substituted with one $R^{21}$ group, and said $R^{21}$ group is phenyl, and said phenyl is substituted with one or more independently selected $R^{22}$ groups.

In another embodiment of this invention $R^1$ is an alkyl group substituted with one $R^{21}$ group, and said $R^{21}$ group is phenyl, and said phenyl is substituted with one or more $R^{22}$ groups, and each $R^{22}$ group is the same or different halo.

In another embodiment of this invention $R^1$ is an alkyl group substituted with one $R^{21}$ group, and said $R^{21}$ group is phenyl, and said phenyl is substituted with one or two $R^{22}$ halo groups, and each $R^{22}$ group is the same or different halo.

In another embodiment of this invention $R^1$ is an alkyl group substituted with one $R^{21}$ group, and said $R^{21}$ group is phenyl, and said phenyl is substituted with one or two $R^{22}$ F groups.

In another embodiment of this invention $R^1$ is an alkyl group substituted with one $R^{21}$ group, and said $R^{21}$ group is phenyl, and said phenyl is substituted with three $R^{22}$ halo groups, and each $R^{22}$ group is the same or different halo.

In another embodiment of this invention $R^1$ is an alkyl group substituted with one $R^{21}$ group, and said $R^{21}$ group is phenyl, and said phenyl is substituted with three $R^{22}$ F groups.

In another embodiment of this invention $R^1$ is an ethyl group substituted with one $R^{21}$ group, and said $R^{21}$ group is an aryl group, and said aryl group is substituted with one or more independently selected $R^{22}$ groups.

In another embodiment of this invention $R^1$ is a methyl group substituted with one $R^{21}$ group, and said $R^{21}$ group is an aryl group, and said aryl group is substituted with one or more independently selected $R^{22}$ groups.

In another embodiment of this invention $R^1$ is an ethyl group substituted with one $R^{21}$ group, and said $R^{21}$ is phenyl, and said phenyl is substituted with one or more independently selected $R^{22}$ groups.

In another embodiment of this invention $R^1$ is a methyl group substituted with one $R^{21}$ group, and said $R^{21}$ group is phenyl, and said phenyl is substituted with one or more independently selected $R^{22}$ groups.

In another embodiment of this invention $R^1$ is an ethyl group substituted with one $R^{21}$ group, and said $R^{21}$ group is phenyl, and said phenyl is substituted with one or two $R^{22}$ halo groups, and each $R^{22}$ group is the same or different halo.

In another embodiment of this invention $R^1$ is a methyl group substituted with one $R^{21}$ group, and said $R^{21}$ group is phenyl, and said phenyl is substituted with one or two $R^{22}$ halo groups, and each $R^{22}$ group is the same or different halo.

In another embodiment of this invention $R^1$ is an ethyl group substituted with one $R^{21}$ group, and said $R^{21}$ group is phenyl, and said phenyl is substituted with one or two $R^{22}$ F groups.

In another embodiment of this invention $R^1$ is a methyl group substituted with one $R^{21}$ group, and said $R^{21}$ group is phenyl, and said phenyl is substituted with one or two $R^{22}$ F groups.

In another embodiment of this invention $R^1$ is an ethyl group substituted with one $R^{21}$ group, and said $R^{21}$ group is phenyl, and said phenyl is substituted with one $R^{22}$ halo group.

In another embodiment of this invention $R^1$ is a methyl group substituted with one $R^{21}$ group, and said $R^{21}$ group is phenyl, and said phenyl is substituted with one $R^{22}$ halo group.

In another embodiment of this invention R¹ is an ethyl group substituted with one $R^{21}$ group, and said $R^{21}$ group is phenyl, and said phenyl is substituted with one $R^{22}$ F group.

In another embodiment of this invention R¹ is a methyl group substituted with one $R^{21}$ group, and said $R^{21}$ group is phenyl, and said phenyl is substituted with one $R^{22}$ F group.

In another embodiment of this invention R¹ is an ethyl group substituted with one $R^{21}$ group, and said $R^{21}$ group is phenyl, and said phenyl is substituted with three independently selected $R^{22}$ halo groups.

In another embodiment of this invention R¹ is a methyl group substituted with one $R^{21}$ group, and said $R^{21}$ group is phenyl, and said phenyl is substituted with three $R^{22}$ independently selected halo groups.

In another embodiment of this invention R¹ an ethyl group substituted with one $R^{21}$ group, and said $R^{21}$ group is phenyl, and said phenyl is substituted with three $R^{22}$ F groups.

In another embodiment of this invention R¹ is a methyl group substituted with one $R^{21}$ group, and said $R^{21}$ group is phenyl, and said phenyl is substituted with three $R^{22}$ F groups.

In another embodiment of this invention R¹ is selected from the group consisting of:

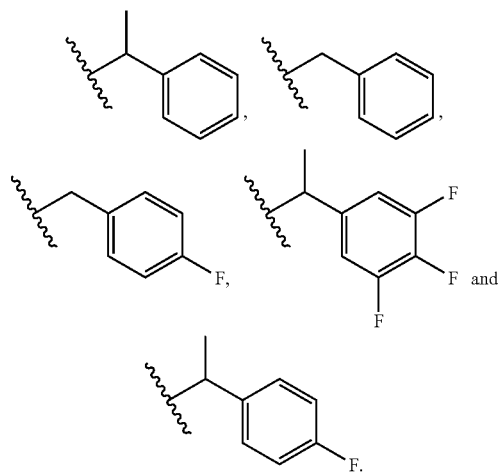

In another embodiment of this invention R¹ is an alkyl group (and in one example R¹ is methyl, and in another example R¹ is ethyl) substituted with a group selected from the group consisting of:

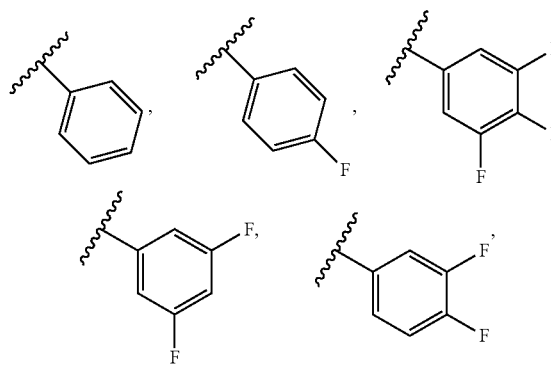

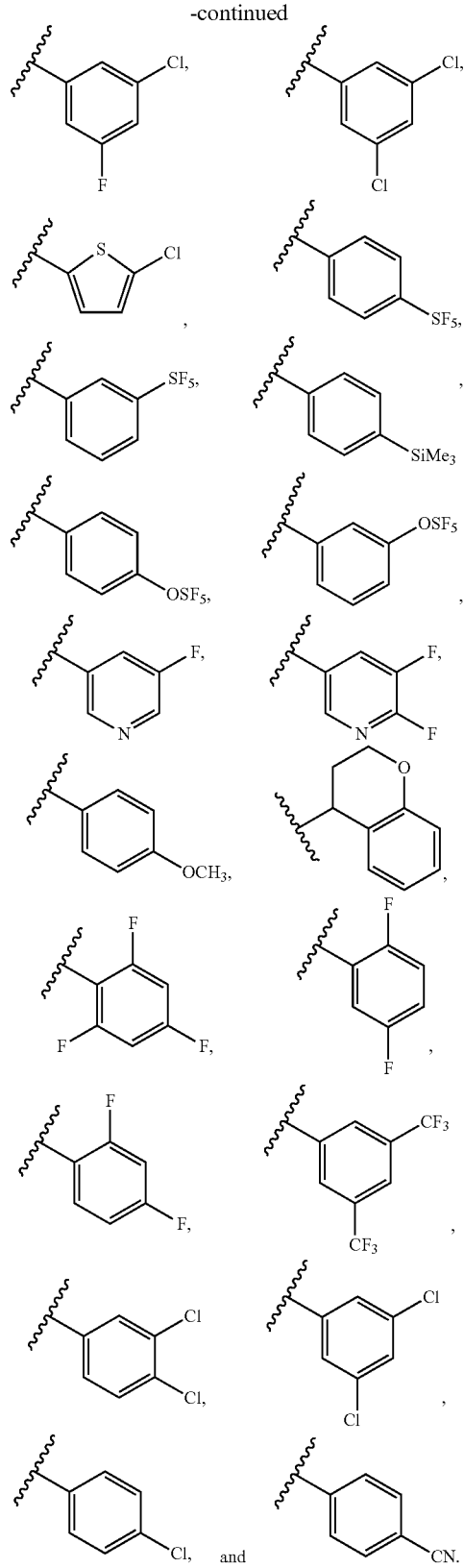

In another embodiment of this invention R¹ is an alkyl group (and in one example R¹ is methyl, and in another example R¹ is ethyl) substituted with a group selected from the group consisting of:

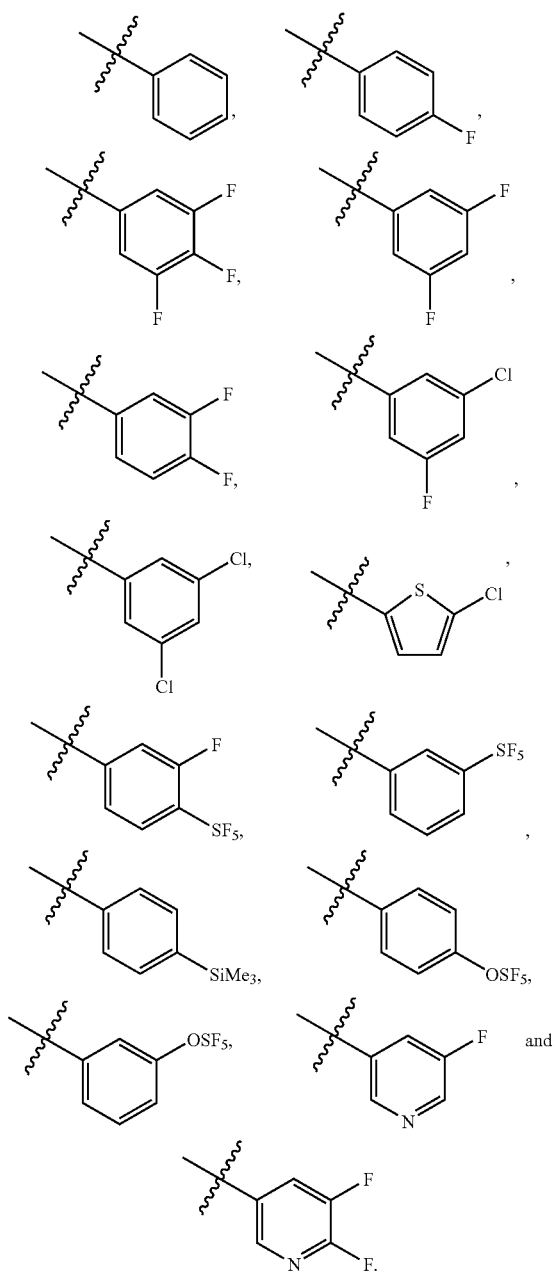

In another embodiment of this invention R¹ is an alkyl group (and in one example R¹ is methyl, and in another example R¹ is ethyl) substituted with

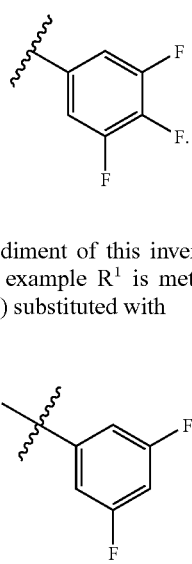

In another embodiment of this invention R¹ is an alkyl group (and in one example R¹ is methyl; and in another example R¹ is ethyl) substituted with

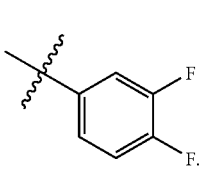 [SMILES: *c1ccc(F)c(F)c1]

In another embodiment of this invention R¹ is an alkyl group (and in one example R¹ is methyl, and in another example R¹ is ethyl) substituted with

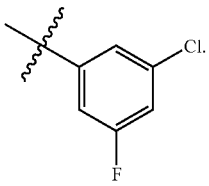 [SMILES: *c1cc(F)cc(Cl)c1]

In another embodiment of this invention R¹ is an alkyl group (and in one example R¹ is methyl, and in another example R¹ is ethyl) substituted with

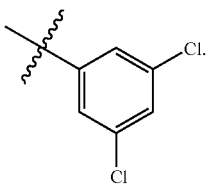 [SMILES: *c1cc(Cl)cc(Cl)c1]

In another embodiment of this invention R¹ is an alkyl group (and in one example R¹ is methyl, and in another example R¹ is ethyl) substituted with

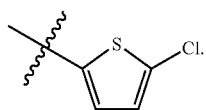 [SMILES: *c1ccc(Cl)s1]

In another embodiment of this invention R¹ is an alkyl group (and in one example R¹ is methyl, and in another example R¹ is ethyl) substituted with

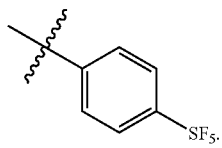

In another embodiment of this invention R¹ is an alkyl group (and in one example R¹ is methyl, and in another example R¹ is ethyl) substituted with

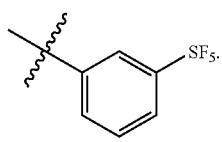

In another embodiment of this invention R¹ is an alkyl group (and in one example R¹ is methyl, and in another example R¹ is ethyl) substituted with

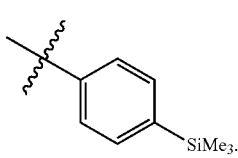

In another embodiment of this invention R¹ is an alkyl group (and in one example R¹ is methyl, and in another example R¹ is ethyl) substituted with

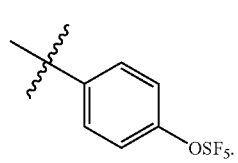

In another embodiment of this invention R¹ is an alkyl group (and in one example R¹ is methyl, and in another example R¹ is ethyl) substituted with

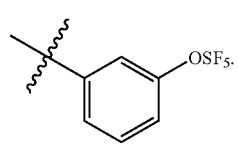

In another embodiment of this invention R¹ is an alkyl group (and in one example R¹ is methyl, and in another example R¹ is ethyl) substituted with

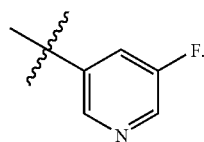 [SMILES: *c1cncc(F)c1]

In another embodiment of this invention R¹ is an alkyl group (and in one example R¹ is methyl, and in another example R¹ is ethyl) substituted with

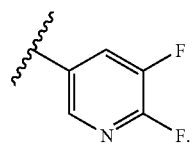 [SMILES: *c1cnc(F)c(F)c1]

In another embodiment of this invention R¹ is an alkyl group (and in one example R¹ is methyl, and in another example R¹ is ethyl) substituted with

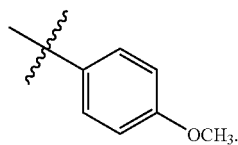 [SMILES: *c1ccc(OC)cc1]

In another embodiment of this invention R¹ is an alkyl group (and in one example R¹ is methyl, and in another example R¹ is ethyl) substituted with

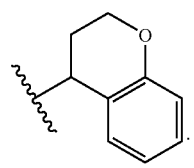 [SMILES: *C1CCOc2ccccc21]

In another embodiment of this invention R¹ is an alkyl group (and in one example R¹ is methyl, and in another example R¹ is ethyl) substituted with

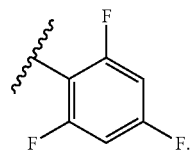 [SMILES: *c1c(F)cc(F)cc1F]

In another embodiment of this invention R¹ is an alkyl group (and in one example R¹ is methyl, and in another example R¹ is ethyl) substituted with

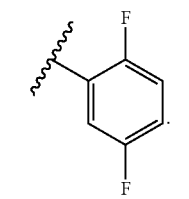 [SMILES: *c1cc(F)ccc1F]

In another embodiment of this invention R¹ is an alkyl group (and in one example R¹ is methyl, and in another example R¹ is ethyl) substituted with

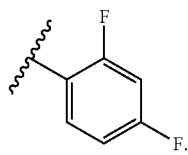 [SMILES: *c1ccc(F)cc1F]

In another embodiment of this invention R¹ is an alkyl group (and in one example R¹ is methyl, and in another example R¹ is ethyl) substituted with

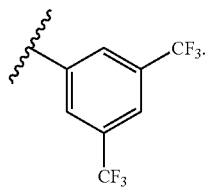 [SMILES: *c1cc(C(F)(F)F)cc(C(F)(F)F)c1]

In another embodiment of this invention R¹ is an alkyl group (and in one example R¹ is methyl, and in another example R¹ is ethyl) substituted with

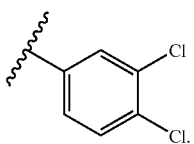 [SMILES: *c1ccc(Cl)c(Cl)c1]

In another embodiment of this invention R¹ is an alkyl group (and in one example R¹ is methyl, and in another example R¹ is ethyl) substituted with

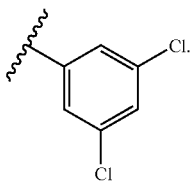 [SMILES: *c1cc(Cl)cc(Cl)c1]

In another embodiment of this invention R¹ is an alkyl group (and in one example R¹ is methyl, and in another example R¹ is ethyl) substituted with

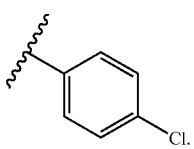 [SMILES: *c1ccc(Cl)cc1]

In another embodiment of this invention R¹ is an alkyl group (and in one example R¹ is methyl, and in another example R¹ is ethyl) substituted with

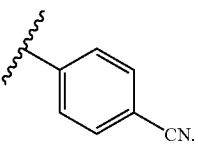 [SMILES: *c1ccc(C#N)cc1]

In another embodiment of this invention R¹ is an alkyl group (and in one example R¹ is methyl, and in another example R¹ is ethyl) substituted with a phenyl that is substituted with 1-3 halos independently selected from the group consisting of F and Cl. In one example said phenyl is substituted with one F and one Cl.

In another embodiment of this invention R¹ is an alkyl group (and in one example R¹ is methyl, and in another example R¹ is ethyl) substituted with an aryl (e.g., phenyl) that is substituted with 1 to 3 independently selected $R^{21}$ moieties wherein at least one $R^{21}$ moiety is selected from the group consisting of $-SF_5$, $-OSF_5$ and $-Si(R^{15A})_3$ (and in one example each $R^{15A}$ is the same or different alkyl, and in another example the $-Si(R^{24})_3$ group is $-Si(CH_3)_3$ or $-Si(CH_2CH_3)_2CH_3$, and in another example the $-Si(R^{24})_3$ group is $-Si(CH_3)_3$).

In another embodiment of this invention R¹ is an alkyl group (and in one example R¹ is methyl, and in another example R¹ is ethyl) substituted with an aryl (e.g., phenyl) that is substituted with 1 to 3 independently selected $R^{21}$ moieties wherein at least one $R^{21}$ moiety is selected from the group consisting of $-SF_5$ and $-OSF_5$.

In another embodiment of this invention R¹ is an alkyl group (and in one example R¹ is methyl, and in another example R¹ is ethyl) substituted with an aryl (e.g., phenyl) that is substituted with 1 to 3 $R^{21}$ moieties independently selected from the group consisting of: halo (e.g., F), $-SF_5$, $-OSF_5$ and $-Si(R^{15A})_3$ (and in one example each $R^{15A}$ is the same or different alkyl, and in another example the $-Si(R^{15A})_3$ group is $-Si(CH_3)_3$ or $-Si(CH_2CH_3)_2CH_3$, and in another example the $-Si(R^{15A})_3$ group is $-Si(CH_3)_3$), and wherein at least one $R^{21}$ moiety is selected from the group consisting of $-SF_5$, $-OSF_5$ and $-Si(R^{15A})_3$ (and in one example each $R^{15A}$ is the same or different alkyl, and in another example the $-Si(R^{15A})_3$ group is $-Si(CH_3)_3$ or $-Si(CH_2CH_3)_2CH_3$, and in another example the $-Si(R^{24})_3$ group is $-Si(CH_3)_3$).

In another embodiment of this invention R¹ is an alkyl group (and in one example R¹ is methyl, and in another example R¹ is ethyl) substituted with an aryl (e.g., phenyl) that is substituted with 1 to 3 $R^{21}$ moieties independently selected from the group consisting of: halo (e.g., F), $-SF_5$ and $-OSF_5$, and wherein at least one $R^{21}$ moiety is selected from the group consisting of $-SF_5$ and $-OSF_5$.

In another embodiment of this invention R¹ is an alkyl group (and in one example R¹ is methyl, and in another example R¹ is ethyl) substituted with an aryl (e.g., phenyl) that is substituted with 1 to 3 independently selected $R^{21}$ moieties wherein at least one $R^{21}$ moiety is selected from the group consisting of $-SF_5$, $-OSF_5$ and $-Si(R^{15A})_3$ (and in one example each $R^{15A}$ is the same or different alkyl, and in another example the $-Si(R^{15A})_3$ group is $-Si(CH_3)_3$ or $-Si(CH_2CH_3)_2CH_3$, and in another example the $-Si(R^{15A})_3$ group is $-Si(CH_3)_3$).

In another embodiment of this invention R¹ is an alkyl group (and in one example R¹ is methyl, and in another example R¹ is ethyl) substituted with a phenyl that is substituted with 1-3 $R^{21}$ groups independently selected from the group consisting of halos, $-SF_5$ and $-OSF_5$, wherein at least one $R^{21}$ group is $-SF_5$ or $-OSF_5$.

In another embodiment of this invention R¹ is an alkyl group (and in one example R¹ is methyl, and in another example R¹ is ethyl) substituted with a phenyl that is substituted with 1-3 $R^{21}$ groups independently selected from the group consisting of halos, $-SF_5$ and $-OSF_5$, wherein at least one $R^{21}$ group is $-SF_5$ or $-OSF_5$.

In another embodiment of this invention R¹ is an alkyl group (and in one example R¹ is methyl, and in another example R¹ is ethyl) substituted with a phenyl that is substituted with 1-3 $R^{21}$ groups independently selected from the group consisting of F, Cl, —$SF_5$ and —$OSF_5$.

In another embodiment of this invention $R^1$ is an alkyl group (and in one example $R^1$ is methyl, and in another example $R^1$ is ethyl) substituted with a phenyl that is substituted with 1-3 $R^{21}$ groups independently selected from the group consisting of —$SF_5$ and —$OSF_5$.

In another embodiment of this invention $R^1$ is an alkyl group (and in one example $R^1$ is methyl, and in another example $R^1$ is ethyl) substituted with a phenyl substituted with 1-3 $R^{21}$ groups independently selected from the group consisting of F, —$SF_5$ and —$OSF_5$, wherein at least one $R^{21}$ group is —$SF_5$ or —$OSF_5$.

In another embodiment of this invention $R^1$ is an alkyl group (and in one example $R^1$ is methyl, and in another example $R^1$ is ethyl) substituted with a phenyl that is substituted with one —$SF_5$ group.

In another embodiment of this invention $R^1$ is an alkyl group (and in one example $R^1$ is methyl, and in another example $R^1$ is ethyl) substituted with a phenyl that is substituted with two —$SF_5$ groups.

In another embodiment of this invention $R^1$ is an alkyl group (and in one example $R^1$ is methyl, and in another example $R^1$ is ethyl) substituted with a phenyl that is substituted with three —$SF_5$ groups.

In another embodiment of this invention $R^1$ is an alkyl group (and in one example $R^1$ is methyl, and in another example $R^1$ is ethyl) substituted with a phenyl that is substituted with one —$OSF_5$ group.

In another embodiment of this invention $R^1$ is an alkyl group (and in one example $R^1$ is methyl, and in another example $R^1$ is ethyl) substituted with a phenyl that is substituted with two —$OSF_5$ groups.

In another embodiment of this invention $R^1$ is an alkyl group (and in one example $R^1$ is methyl, and in another example $R^1$ is ethyl) substituted with a phenyl that is substituted with three —$OSF_5$ groups.

In another embodiment of this invention $R^1$ is an alkyl group (and in one example $R^1$ is methyl, and in another example $R^1$ is ethyl) substituted with a phenyl that is substituted with 1 F.

In another embodiment of this invention $R^1$ is an alkyl group (and in one example $R^1$ is methyl, and in another example $R^1$ is ethyl) substituted with a phenyl that is substituted with 1 F, and also substituted with 1 to 2 groups independently selected from the group consisting of —$SF_5$ and —$OSF_5$.

In another embodiment of this invention $R^1$ is an alkyl group (and in one example $R^1$ is methyl, and in another example $R^1$ is ethyl) substituted with a phenyl that is substituted with 2 F.

In another embodiment of this invention $R^1$ is an alkyl group (and in one example $R^1$ is methyl, and in another example $R^1$ is ethyl) substituted with a phenyl that is substituted with 3F.

In another embodiment of this invention $R^1$ is an unsubstituted or substituted aryl (e.g., phenyl) group.

In another embodiment of this invention $R^1$ is an unsubstituted aryl (e.g., phenyl) or aryl (e.g., phenyl) substituted with one or more independently selected $R^{21}$ groups.

In another embodiment of this invention $R^1$ is an aryl group.

In another embodiment of this invention $R^1$ is an aryl group, and said aryl group is substituted with one or more independently selected $R^{21}$ groups.

In another embodiment of this invention $R^1$ is an aryl group, and said aryl group is substituted with 1 to 3 independently selected $R^{21}$ groups.

In another embodiment of this invention $R^1$ is an aryl group, and said aryl group is substituted with one or more $R^{21}$ groups, and each $R^{21}$ group is the same or different halo.

In another embodiment of this invention $R^1$ is an aryl group, and said aryl group is substituted with 1 to 3 $R^{21}$ groups, and each $R^{21}$ group is the same or different halo.

In another embodiment of this invention $R^1$ is an aryl group, and said aryl group is substituted with three $R^{21}$ halo groups, and each $R^{21}$ group is the same or different halo.

In another embodiment of this invention $R^1$ is an aryl group, and said aryl group is substituted with two $R^{21}$ halo groups, and each $R^{21}$ group is the same or different halo.

In another embodiment of this invention $R^1$ is an aryl group, and said aryl group is substituted with one $R^{21}$ halo group.

In another embodiment of this invention $R^1$ is an aryl group, and said aryl group is substituted with one $R^{21}$ halo groups, and each $R^{21}$ group is the same or different halo.

In another embodiment of this invention $R^1$ is an aryl group, and said aryl group is substituted with one F (i.e., said aryl is substituted with one $R^{21}$ group, and said $R^{21}$ group is halo, and said halo is F).

In another embodiment of this invention $R^1$ is an aryl group, and said aryl group is substituted with two F atoms (i.e., said aryl is substituted with two $R^{21}$ groups, and said $R^{21}$ groups are halo, and said halo is F).

In another embodiment of this invention $R^1$ is an aryl group, and said aryl group is substituted with three F atoms (i.e., said aryl is substituted with three $R^{21}$ groups, and said $R^{21}$ groups are halo, and said halo is F).

In another embodiment of this invention $R^1$ is phenyl.

In another embodiment of this invention $R^1$ is phenyl, and said phenyl is substituted with one or more independently selected $R^{21}$ groups.

In another embodiment of this invention $R^1$ is phenyl, and said phenyl is substituted with 1 to 3 independently selected $R^{21}$ groups.

In another embodiment of this invention $R^1$ is a phenyl, and said phenyl is substituted with one or more $R^{21}$ groups, and each $R^{21}$ group is the same or different halo.

In another embodiment of this invention $R^1$ is phenyl, and said phenyl is substituted with 1 to 3 $R^{21}$ groups, and each $R^{21}$ group is the same or different halo.

In another embodiment of this invention $R^1$ is phenyl, and said phenyl is substituted with three $R^{21}$ halo groups, and each $R^{21}$ group is the same or different halo.

In another embodiment of this invention $R^1$ is phenyl, and said phenyl is substituted with two $R^{21}$ halo groups, and each $R^{21}$ group is the same or different halo.

In another embodiment of this invention $R^1$ is phenyl, and said phenyl is substituted with one $R^{21}$ halo group.

In another embodiment of this invention $R^1$ is phenyl, and said phenyl is substituted with one $R^{21}$ halo group.

In another embodiment of this invention $R^1$ is phenyl, and said phenyl is substituted with one F (i.e., said aryl is substituted with one $R^{21}$ group, and said $R^{21}$ group is halo, and said halo is F).

In another embodiment of this invention $R^1$ is phenyl, and said phenyl is substituted with two F atoms (i.e., said aryl is substituted with two $R^{21}$ groups, and said $R^{21}$ groups are halo, and said halo is F).

In another embodiment of this invention R¹ is phenyl, and said phenyl is substituted with three F atoms (i.e., said aryl is substituted with three R²¹ groups, and said R²¹ groups are halo, and said halo is F).

In another embodiment of this invention R¹ is selected from the group consisting of:

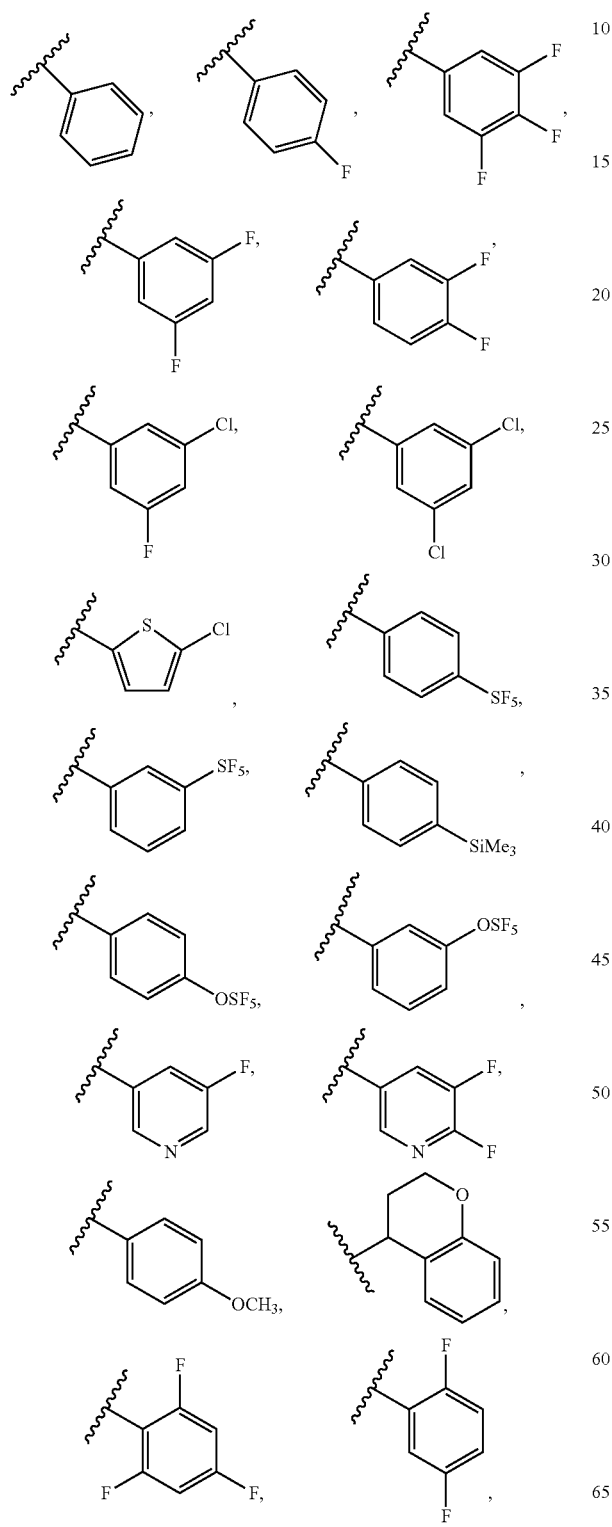

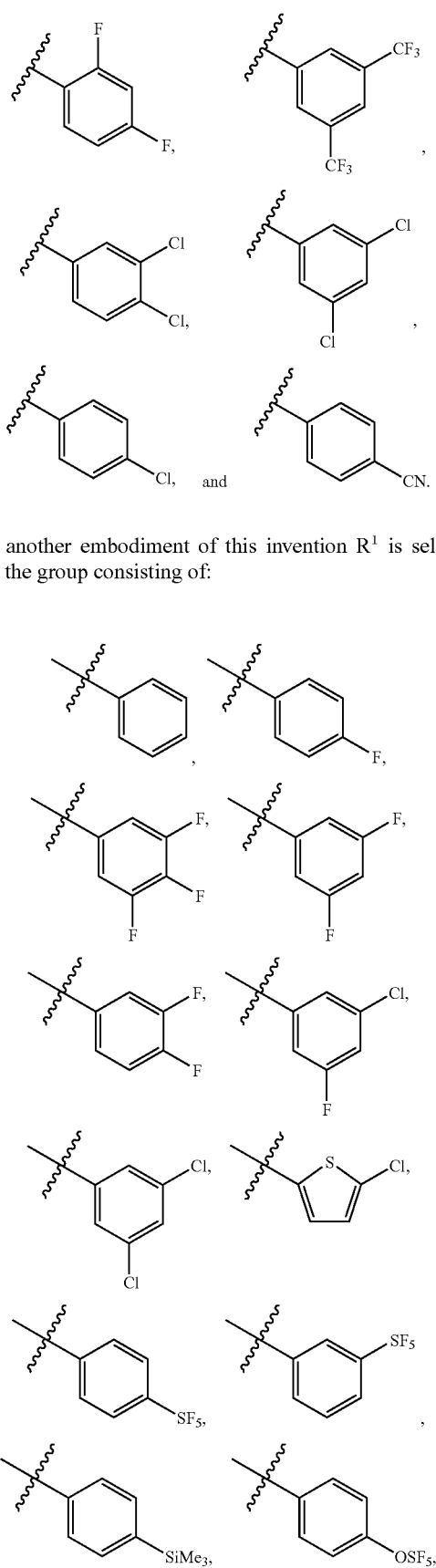

In another embodiment of this invention R¹ is selected from the group consisting of:

-continued

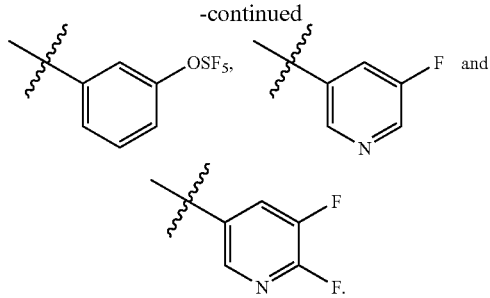

In another embodiment of this invention $R^{1A}$ is:

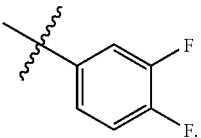

In another embodiment of this invention $R^1$ is selected from the group consisting of:

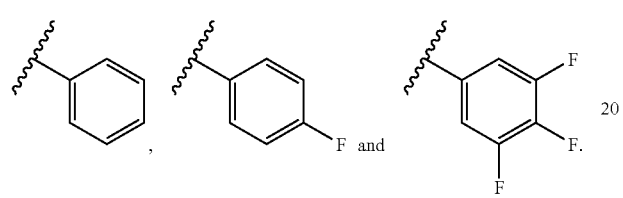

In another embodiment of this invention $R^{1A}$ is:

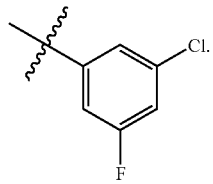

In another embodiment of this invention $R^1$ is selected from the group consisting of:

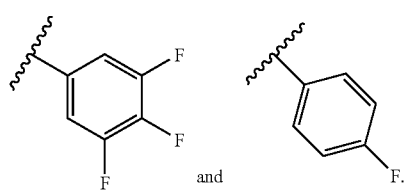 [SMILES: *c1cc(F)c(F)c(F)c1 ; "and" ; *c1ccc(F)cc1]

In another embodiment of this invention $R^{1A}$ is:

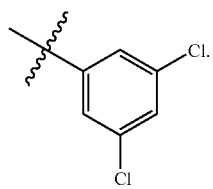

In another embodiment of this invention $R_1$ is:

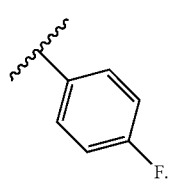 [SMILES: *c1ccc(F)cc1]

In another embodiment of this invention $R^1$ is:

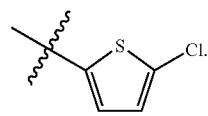

In another embodiment of this invention $R^{1A}$ is:

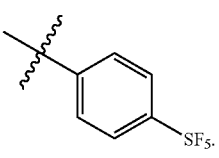

In another embodiment of this invention $R^1$ is:

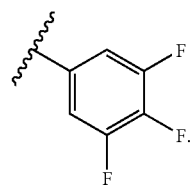 [SMILES: *c1cc(F)c(F)c(F)c1]

In another embodiment of this invention $R^1$ is:

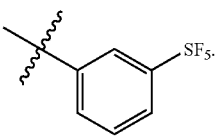

In another embodiment of this invention $R^1$ is:

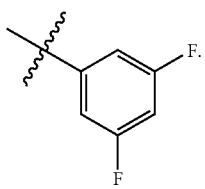 [SMILES: *c1cc(F)cc(F)c1]

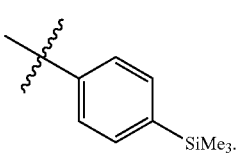

In another embodiment of this invention R¹ is:

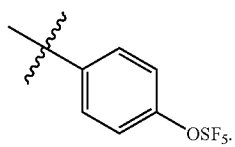

In another embodiment of this invention R¹⁴ is:

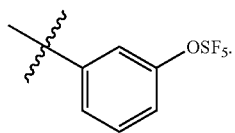

In another embodiment of this invention R¹ is:

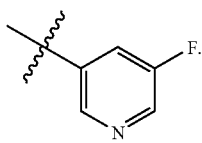

In another embodiment of this invention R¹ is:

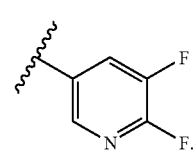 [SMILES: *c1cnc(F)c(F)c1]

In another embodiment of this invention R¹ is:

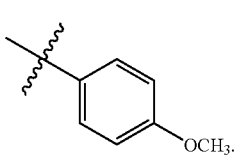 [SMILES: *c1ccc(OC)cc1]

In another embodiment of this invention R¹ is:

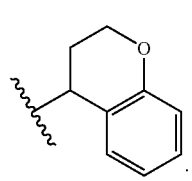 [SMILES: *C1CCOc2ccccc21]

In another embodiment of is invention R¹ is:

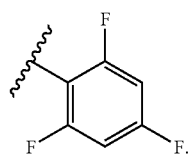 [SMILES: *c1c(F)cc(F)cc1F]

In another embodiment of this invention. R¹ is

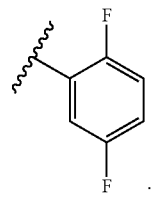 [SMILES: *c1cc(F)ccc1F]

In another embodiment of this invention R¹ is:

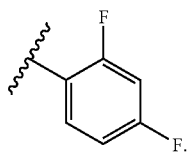 [SMILES: *c1ccc(F)cc1F]

In another embodiment of this invention R¹⁴ is:

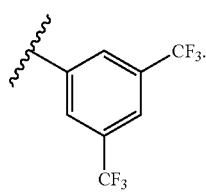 [SMILES: *c1cc(C(F)(F)F)cc(C(F)(F)F)c1]

In another embodiment of this invention R¹ is:

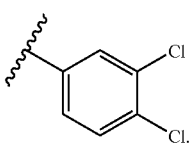

In another embodiment of this invention R¹ is:

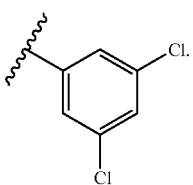 [SMILES: *c1cc(Cl)cc(Cl)c1]

In another embodiment of this invention R¹ is:

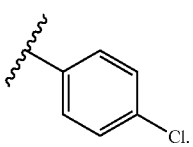 [SMILES: *c1ccc(Cl)cc1]

In another embodiment of this invention R¹ is:

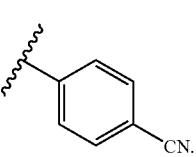 [SMILES: *c1ccc(C#N)cc1]

In another embodiment, $R^1$ is phenyl substituted with 1-3 halos independently selected from the group consisting of F and Cl. In one example said phenyl is substituted with one F and one Cl.

In another embodiment $R^1$ is aryl (e.g., phenyl) substituted with 1 to 3 independently selected $R^{21}$ moieties wherein at least one $R^{21}$ moiety is selected from the group consisting of $-SF_5$, $-OSF_5$ and $-Si(R^{15A})_3$ (and in one example each $R^{15A}$ is the same or different alkyl, and in another example the $-Si(R^{24})_3$ group is $-Si(CH_3)_3$ or $-Si(CH_2CH_3)_2CH_3$, and in another example the $-Si(R^{24})_3$ group is $-Si(CH_3)_3$).

In another embodiment $R^1$ is aryl (e.g., phenyl) substituted with 1 to 3 independently selected $R^{21}$ moieties wherein at least one $R^{21}$ moiety is selected from the group consisting of $-SF_5$ and $-OSF_5$.

In another embodiment $R^1$ is aryl (e.g., phenyl) substituted with 1 to 3 $R^{21}$ moieties independently selected from the group consisting of: halo (e.g., F), $-SF_5$, $-OSF_5$ and $-Si(R^{15A})_3$ (and in one example each $R^{15A}$ is the same or different alkyl, and in another example the $-Si(R^{15A})_3$ group is $-Si(CH_3)_3$ or $-Si(CH_2CH_3)_2CH_3$, and in another example the $-Si(R^{15A})_3$ group is $-Si(CH_3)_3$), and wherein at least one $R^{21}$ moiety is selected from the group consisting of $-SF_5$, $-OSF_5$ and $-Si(R^{15A})_3$ (and in one example each $R^{15A}$ is the same or different alkyl, and in another example the $-Si(R^{15A})_3$ group is $-Si(CH_3)_3$ or $-Si(CH_2CH_3)_2CH_3$, and in another example the $-Si(R^{24})_3$ group is $-Si(CH_3)_3$).

In another embodiment $R^1$ is aryl (e.g., phenyl) substituted with 1 to 3 $R^{21}$ moieties independently selected from the group consisting of: halo (e.g., F), $-SF_5$ and $-OSF_5$, and wherein at least one $R^{21}$ moiety is selected from the group consisting of $-SF_5$ and $-OSF_5$.

In another embodiment $R^1$ is aryl (e.g., phenyl) substituted with 1 to 3 independently selected $R^{21}$ moieties wherein at least one $R^{21}$ moiety is selected from the group consisting of $-SF_5$, $-OSF_5$ and $-Si(R^{15A})_3$ (and in one example each $R^{15A}$ is the same or different alkyl, and in another example the $-Si(R^{15A})_3$ group is $-Si(CH_3)_3$ or $-Si(CH_2CH_3)_2CH_3$, and in another example the $-Si(R^{15A})_3$ group is $-Si(CH_3)_3$)

In another embodiment, $R^1$ is phenyl substituted with 1-3 $R^{21}$ groups independently selected from the group consisting of halos, $-SF_5$ and $-OSF_5$, wherein at least one $R^{21}$ group is $-SF_5$ or $-OSF_5$.

In another embodiment, $R^1$ is phenyl substituted with 1-3 $R^{21}$ groups independently selected from the group consisting of halos, $-SF_5$ and $-OSF_5$, wherein at least one $R^{21}$ group is $-SF_5$ or $-OSF_5$.

In another embodiment, $R^1$ is phenyl substituted with 1-3 $R^{21}$ groups independently selected from the group consisting of F, Cl, $-SF_5$ and $-OSF_5$.

In another embodiment, $R^1$ is phenyl substituted with 1-3 $R^{21}$ groups independently selected from the group consisting of $-SF_5$ and $-OSF_5$.

In another embodiment, $R^1$ is phenyl substituted with 1-3 $R^{21}$ groups independently selected from the group consisting of F, $-SF_5$ and $-OSF_5$, wherein at least one $R^{21}$ group is $-SF_5$ or $-OSF_5$.

In another embodiment, $R^1$ is phenyl substituted with one $-SF_5$ group.

In another embodiment, $R^1$ is phenyl substituted with two $-SF_5$ groups.

In another embodiment, $R^1$ is phenyl substituted with three $-SF_5$ groups.

In another embodiment, $R^1$ is phenyl substituted with one $-OSF_5$ group.

In another embodiment, $R^1$ is phenyl substituted with two $-OSF_5$ groups.

In another embodiment, $R^1$ is phenyl substituted with three $-OSF_5$ groups.

In another embodiment, $R^1$ is phenyl substituted with 1 F.

In another embodiment, $R^1$ is phenyl substituted with 1 F, and also substituted with 1 to 2 groups independently selected from the group consisting of $-SF_5$ and $-OSF_5$.

In another embodiment $R^1$ is phenyl substituted with 2 F.

In another embodiment $R^1$ is phenyl substituted with 3F.

In another embodiment of this invention $R^{10}$ is selected from the group consisting of aryl and aryl substituted with one or more $R^{21}$ groups, and said $R^9$ group is selected from the group consisting of heteroaryl and heteroaryl substituted with one or more $R^{21}$ groups, and wherein each $R^{21}$ is independently selected.

In another embodiment of this invention: (a) $R^1$ is an alkyl group substituted with one $R^{21}$ group, or (b) $R^1$ is an alkyl group substituted with one $R^{21}$ group, and said $R^{21}$ group is substituted with one or more independently selected $R^{22}$ groups, and (c) $R^{10}$ is selected from the group consisting of aryl and aryl substituted with one or more independently selected $R^{21}$ groups, and (d) $R^9$ is selected from the group consisting of heteroaryl and heteroaryl substituted with one or more independently selected $R^{21}$ groups.

In another embodiment of this invention: (a) $R^1$ is an alkyl group substituted with one phenyl group, or (b) $R^1$ is an alkyl group substituted with one phenyl group, and said phenyl group is substituted with one or more independently selected $R^{22}$ groups, and (c) $R^{10}$ is selected from the group consisting of phenyl and phenyl substituted with one or more independently selected $R^{21}$ groups, and (d) $R^9$ is selected from the group consisting of imidazolyl and imidazolyl substituted with one or more independently selected $R^{21}$ groups.

In another embodiment of this invention: (a) $R^1$ is a methyl or ethyl group substituted with one phenyl, or (b) $R^1$ is an methyl or alkyl group substituted with one phenyl, and said phenyl is substituted with one or more independently selected halos, and (c) $R^{10}$ is selected from the group consisting of phenyl and phenyl substituted with one or more independently selected $-OR^{15}$ groups, and (d) $R^9$ is selected from the group consisting of imidazolyl and imidazolyl substituted with one or more independently selected alkyl groups groups.

In another embodiment of this invention: (a) $R^1$ is a methyl or ethyl group substituted with one phenyl, or (b) $R^1$ is an methyl or alkyl group substituted with one phenyl, and said phenyl is substituted with one or two independently selected halos, and (c) $R^{10}$ is selected from the group consisting of phenyl and phenyl substituted with one or two independently selected $-OR^{15}$ groups, wherein $R^{15}$ is alkyl, and (d) $R^9$ is selected from the group consisting of imidazolyl and imidazolyl substituted with one or two independently selected alkyl groups groups.

In another embodiment of this invention: (a) $R^1$ is a methyl or ethyl group substituted with one phenyl, or (b) $R^1$ is an methyl or alkyl group substituted with one phenyl, and said phenyl is substituted with one or two F, and (c) $R^{10}$ is selected from the group consisting of phenyl and phenyl substituted with one or two independently selected $-OR^{15}$ groups, wherein $R^{15}$ is methyl and (d) $R^9$ is selected from the group consisting of imidazolyl and imidazolyl substituted with one or two independently selected methyl groups groups.

In another embodiment of this invention: (a) $R^1$ is a methyl or ethyl group substituted with one phenyl, or (b) $R^1$ is an methyl or alkyl group substituted with one phenyl; and said phenyl is substituted with one or more F, and (c) $R^{10}$ is phenyl substituted with one $-OR^{15}$ group, wherein $R^{15}$ is methyl, and (d) $R^9$ is selected from the group consisting of imidazolyl and imidazolyl substituted with one methyl group.

In another embodiment of this invention R¹ is selected from the group consisting of:

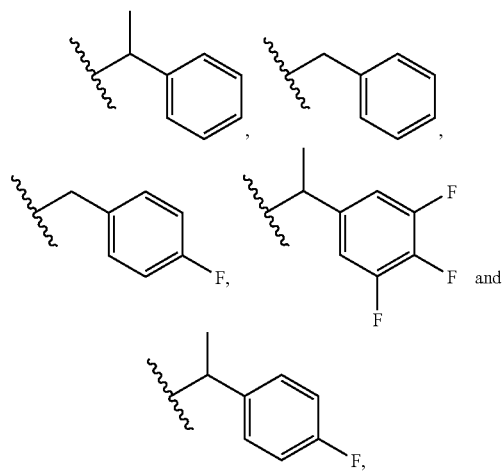

and
wherein the $R^9$-$R^{10}$-moiety is:

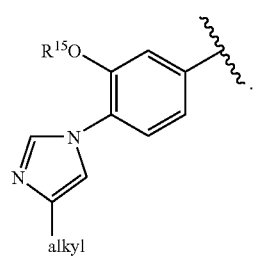

alkyl

In another embodiment of this invention R is selected from the group consisting of:

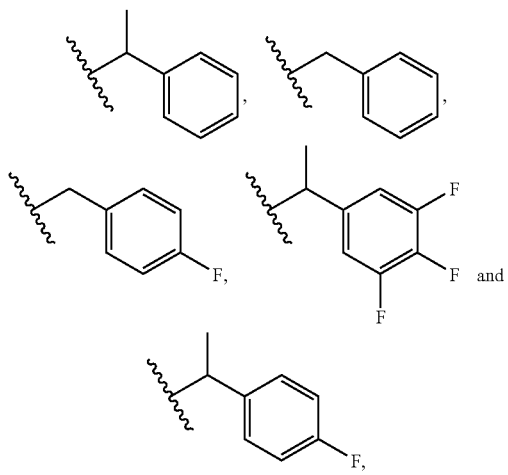

and
wherein the $R^9$-$R^{10}$-moiety is:

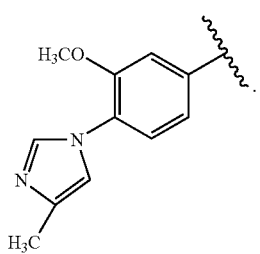

In another embodiment of this invention R¹ is selected from the group consisting of:

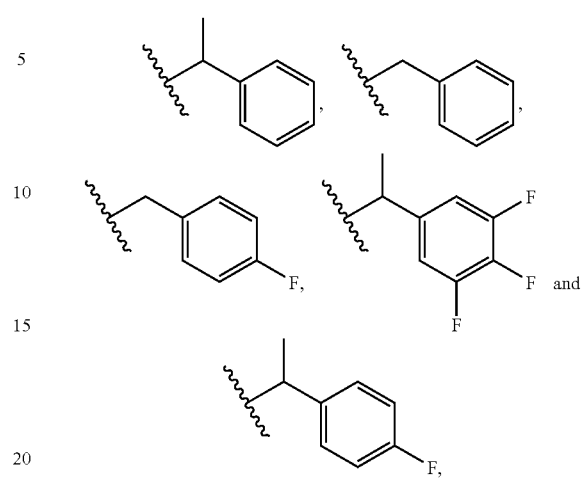

wherein the $R^9$-$R^{10}$-moiety is:

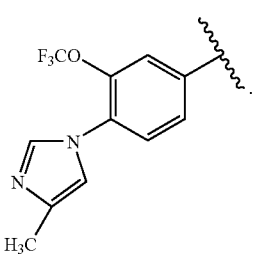

In another embodiment of this invention R¹ is selected from the group consisting of:

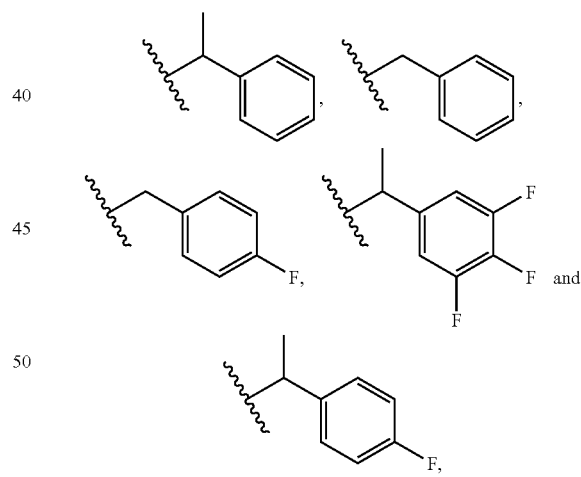

wherein the $R^9$-$R^{10}$-moiety is:

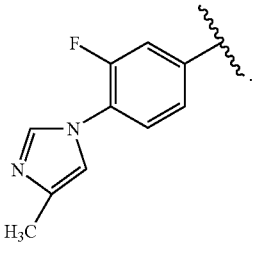 [SMILES: *c1ccc(-n2cnc(C)c2)c(F)c1]

In another embodiment of this invention R¹ is selected from the group consisting of:

[chemical structures: 1-phenylethyl, benzyl, 4-fluorobenzyl, 1-(3,4,5-trifluorophenyl)ethyl, and 1-(4-fluorophenyl)ethyl groups]

wherein the R⁹-R¹⁰-moiety is:

[chemical structure: pyridine substituted with 4-methylimidazol-1-yl]

In another embodiment of this invention: (a) R¹ is a methyl or ethyl group substituted with one phenyl, or (b) R¹ is an methyl or alkyl group substituted with one phenyl, and said phenyl is substituted with 1 to 3 independently selected halos, and (c) R¹⁰ is selected from the group consisting of phenyl and phenyl substituted with one or two independently selected —OR¹⁵ groups, wherein R¹⁵ is alkyl, and (d) R⁹ is selected from the group consisting of imidazolyl and imidazolyl substituted with one or two independently selected alkyl groups groups.

In another embodiment of this invention: (a) R¹ is a methyl or ethyl group substituted with one phenyl, or (b) R¹ is an methyl or alkyl group substituted with one phenyl, and said phenyl is substituted with 1 to 3 independently selected halos, and (c) R¹⁰ is selected from the group consisting of phenyl and phenyl substituted with one or two independently selected —OR¹⁵ groups, wherein R¹⁵ is alkyl, and (d) R⁹ is selected from the group consisting of imidazolyl and imidazolyl substituted with one or two independently selected alkyl groups groups, and (e) G⁵ is selected from the group consisting of —N═, —NH—, —O— and —S—.

In another embodiment of this invention: (a) R¹ is a methyl or ethyl group substituted with one phenyl, or (b) R¹ is an methyl or alkyl group substituted with one phenyl, and said phenyl is substituted with 1 to 3 independently selected halos, and (c) R¹⁰ is selected from the group consisting of phenyl and phenyl substituted with one or two independently selected —OR¹⁵ groups, wherein R¹⁵ is alkyl, and (d) R⁹ is selected from the group consisting of imidazolyl and imidazolyl substituted with one or two independently selected alkyl groups groups, and (e) G⁵ is selected from the group consisting of —N═, —NH—, —O— and —S—, and (f) G⁶ is C or CH.

In another embodiment of this invention: (a) R¹ is a methyl or ethyl group substituted with one phenyl, or (b) R¹ is an methyl or alkyl group substituted with one phenyl, and said phenyl is substituted with 1 to 3 F, and (c) R¹⁰ is selected from the group consisting of phenyl and phenyl substituted with one or two independently selected —OR¹⁵ groups, wherein R¹⁵ is alkyl, and (d) R⁹ is selected from the group consisting of imidazolyl and imidazolyl substituted with one or two independently selected alkyl groups groups.

In another embodiment of this invention: (a) R¹ is a methyl or ethyl group substituted with one phenyl, or (b) R¹ is an methyl or alkyl group substituted with one phenyl, and said phenyl is substituted with 1 to 3 F, and (c) R¹⁰ is selected from the group consisting of phenyl and phenyl substituted with one or two independently selected —OR¹⁵ groups, wherein R¹⁵ is alkyl, and (d) R⁹ is selected from the group consisting of imidazolyl and imidazolyl substituted with one or two independently selected alkyl groups groups, and (e) G⁵ is selected from the group consisting of —N═, —NH—, —O— and —S—.

In another embodiment of this invention: (a) R¹ is a methyl or ethyl group substituted with one phenyl, or (b) R¹ is an methyl or alkyl group substituted with one phenyl, and said phenyl is substituted with 1 to 3 F, and (c) R¹⁰ is selected from the group consisting of phenyl and phenyl substituted with one or two independently selected —OR¹⁵ groups, wherein R¹⁵ is alkyl, and (d) R⁹ is selected from the group consisting of imidazolyl and imidazolyl substituted with one or two independently selected alkyl groups groups, and (e) G⁵ is selected from the group consisting of —N═, —NH—, —O— and —S—, and (f) G⁶ is C or CH.

In another embodiment of this invention: (a) R¹ is a methyl or ethyl group substituted with one phenyl, or (b) R¹ is an methyl or alkyl group substituted with one phenyl, and said phenyl is substituted with 1 to 3 F, and (c) R¹⁰ is phenyl substituted with one —OR¹⁵ group, wherein R¹⁵ is methyl, and (d) R⁹ is selected from the group consisting of imidazolyl and imidazolyl substituted with one methyl group.

In another embodiment of this invention: (a) R¹ is a methyl or ethyl group substituted with one phenyl, or (b) R¹ is an methyl or alkyl group substituted with one phenyl, and said phenyl is substituted with 1 to 3 F, and (c) R¹⁰ is phenyl substituted with one —OR¹⁵ group, wherein R¹⁵ is methyl, and (d) R⁹ is selected from the group consisting of imidazolyl and imidazolyl substituted with one methyl group, and (e) G⁵ is selected from the group consisting of —N═, —NH—, —O— and —S—.

In another embodiment of this invention: (a) R¹ is a methyl or ethyl group substituted with one phenyl, or (b) R¹ is an methyl or alkyl group substituted with one phenyl, and said phenyl is substituted with 1 to 3 F, and (c) R¹⁰ is phenyl substituted with one —OR¹⁵ group, wherein R¹⁵ is methyl, and (d) R⁹ is selected from the group consisting of imidazolyl and imidazolyl substituted with one methyl group, and (e) G⁵ is selected from the group consisting of —N═, —NH—, —O— and —S—, and (f) G⁶ is C or CH.

In another embodiment of this invention R¹ is selected from the group consisting of:

[chemical structures: 1-phenylethyl and benzyl groups]

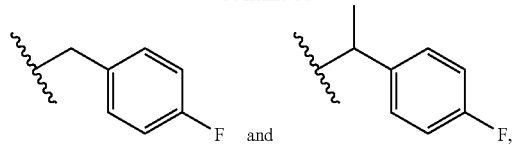 and and
wherein the $R^9$-$R^{10}$-moiety is:

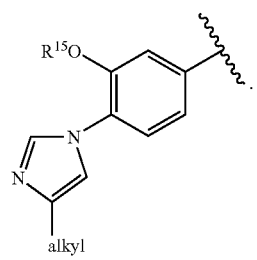

In another embodiment of this invention $R^1$ is selected from the group consisting of:

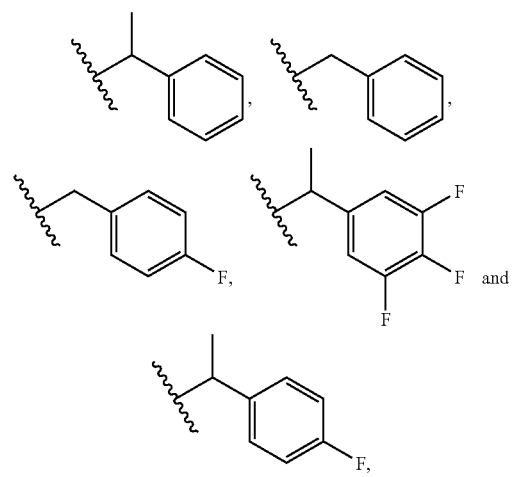

and
wherein the $R^9$-$R^{10}$-moiety is:

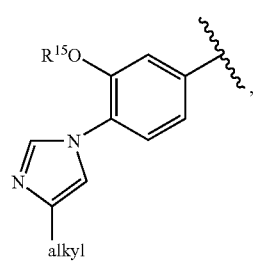

and
$G^5$ is selected from the group consisting of —NH—, —O— and —S—, and $G^6$ is C or CH.

In another embodiment of this invention $R^1$ is selected from the group consisting of:

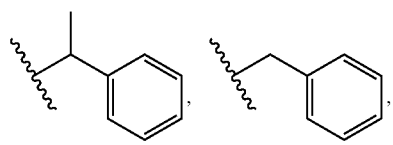

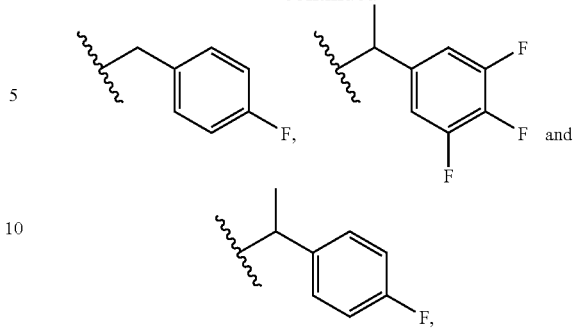

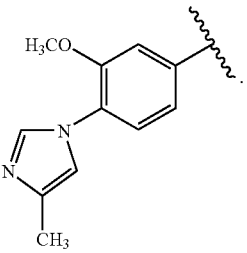 [SMILES: *c1ccc(-n2cnc(C)c2)c(OC)c1]

and
wherein the $R^9$-$R^{10}$-moiety is:

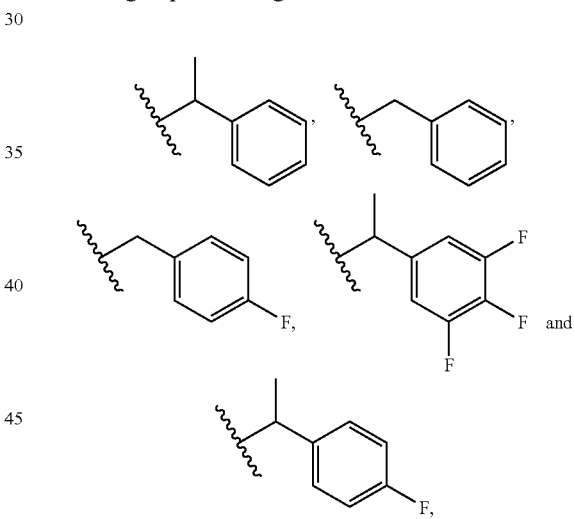

In another embodiment of this invention $R^1$ is selected from the group consisting of:

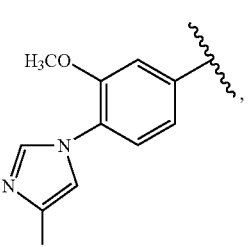

and
wherein the $R^9$-$R^{10}$-moiety is:

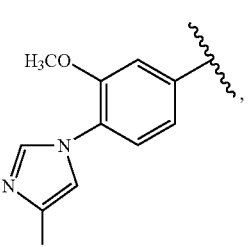

and
$G^5$ is selected from the group consisting of —N═, —NH—, —O— and —S—, and $G^6$ is C or CH.

In another embodiment of this invention R¹ is selected from the group consisting of:

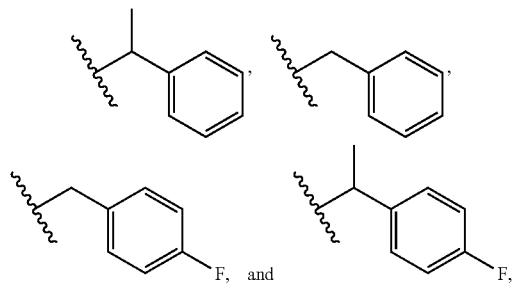

and
wherein the R⁹-R¹⁰-moiety is:

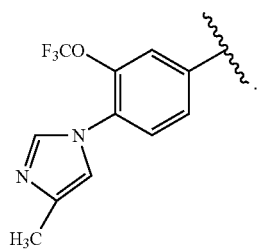

In another embodiment of this invention R¹ is selected from the group consisting of:

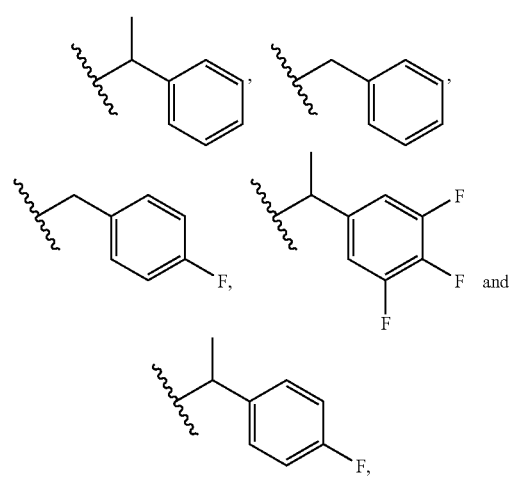

and
wherein the R⁹-R¹⁰-moiety is:

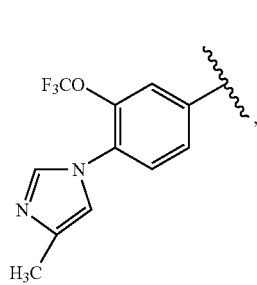

and
G⁵ is selected from the group consisting of —N═, —NH—, —O— and —S—, and G⁶ is C or CH.

In another embodiment of this invention R¹ is selected from the group consisting of:

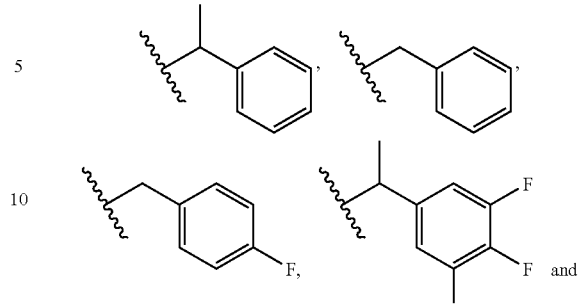

and
wherein the R⁹-R¹⁰-moiety is:

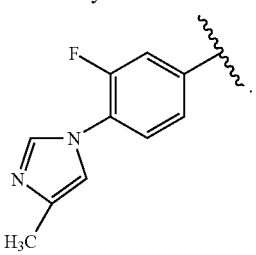

In another embodiment of this invention R¹ is selected from the group consisting of:

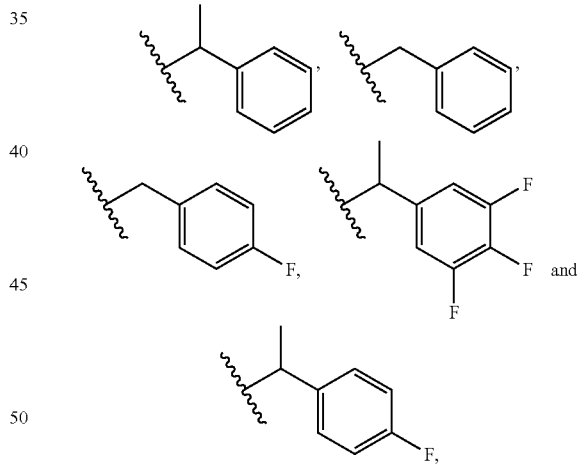

and
wherein the R⁹-R¹⁰-moiety is:

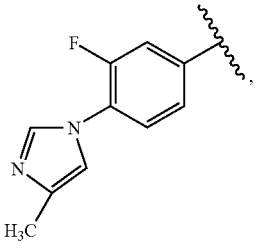

and
G⁵ is selected from the group consisting of —NH═, —O— and —S—, and G⁶ is C or CH.

In another embodiment of this invention R$^1$ is selected from the group consisting of:

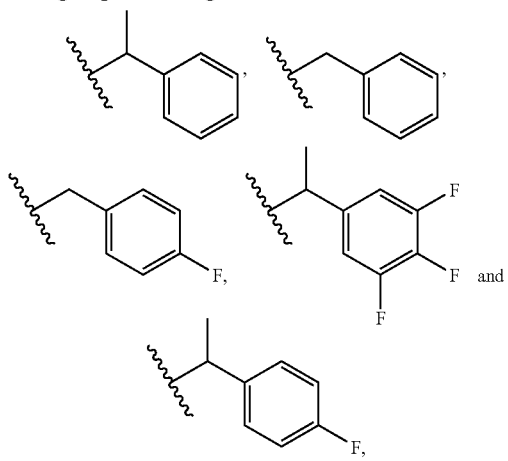

and
wherein the R$^9$-R$^{10}$-moiety is:

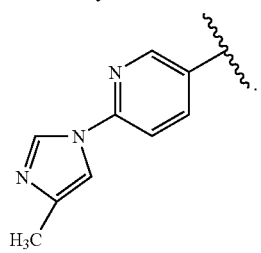

In another embodiment of this invention R$^1$ is selected from the group consisting of:

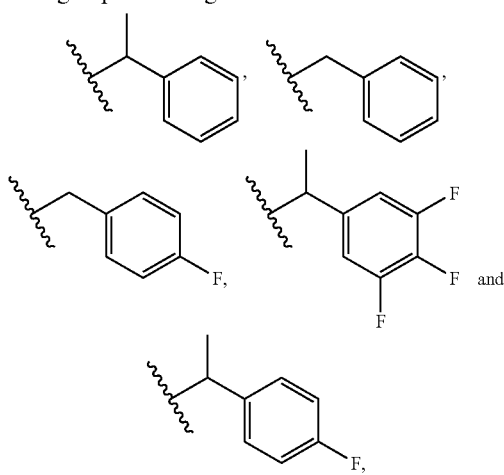

and
wherein the R$^9$-R$^{10}$-moiety is:

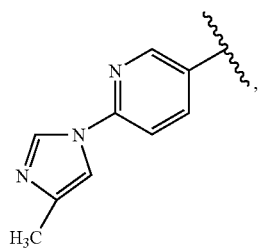

and
G$^5$ is selected from the group consisting of —N═, —NH—, —O— and —S—, and G$^6$ is C or CH.

Other embodiments of this invention are directed to compounds of formula (I) wherein R$^1$ is selected from the group consisting of: benzofusedcycloalkyl (i.e., fused benzocycloalkyl), fused benzoheterocycloalkyl, fused heteroarylcycloalkyl, fused heteroarylheterocycloalkyl, and wherein said R$^1$ groups are optionally substituted with 1-5 independently selected R$^{21}$ groups. In one example, the R$^{21}$ groups are halo (e.g., F).

Examples of the fused ring R$^1$ groups include, but are not limited to:

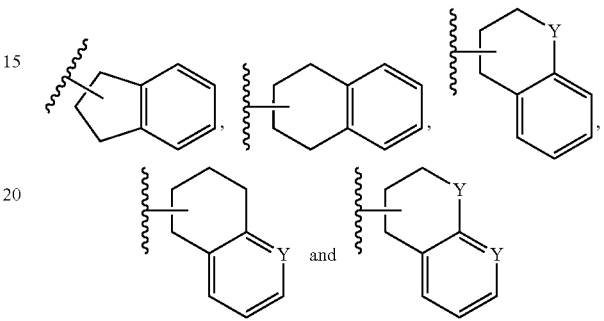

wherein each Y is independently selected from the group consisting of: —O—, —NR$^{14}$— and —C(R$^{21}$)$_q$—, wherein q is as defined above (i.e., 0, 1 or 2 and each R$^{21}$ is independently selected), and wherein R$^{14}$ and R$^{21}$ are as defined for formula (I).

Examples of these R$^1$ groups include, for example:

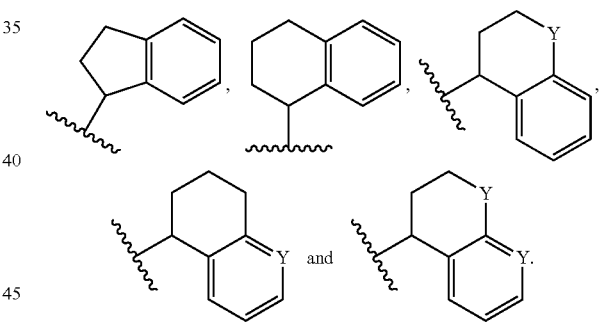

Compounds of formula (I) also include compounds wherein R$^1$ is an alkyl group (e.g., ethyl) substituted with one R$^{21}$ group. Examples of said R$^1$ groups include alkyl (e.g., methyl or ethyl) substituted with the R$^{21}$ moiety aryl (e.g., phenyl or naphthyl). Examples of said R$^1$ groups also include alkyl (e.g., methyl or ethyl) substituted with the R$^{21}$ moiety aryl (e.g., phenyl or naphthyl), which in turn is substituted with one or more (e.g., one or two) independently selected R$^{22}$ groups (e.g., R$^{22}$ is halo, such as, for example, F).

Examples of the substituted R$^1$ alkyl groups include, but are not limited to:

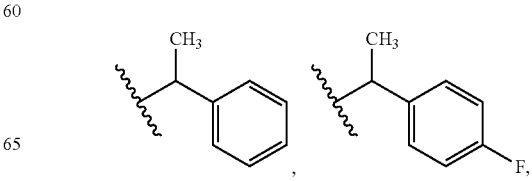

-continued

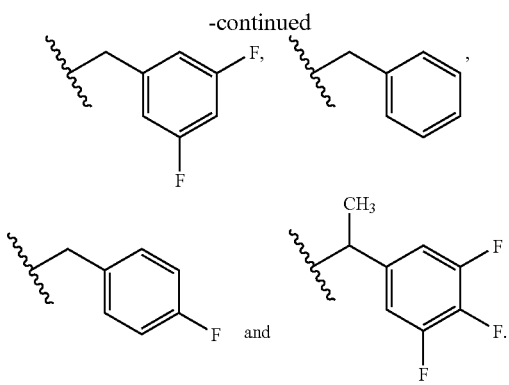

Other embodiments of this invention are directed to compounds of formula (I) wherein $R^1$ is a cycloalkyl group (e.g., cyclopropyl or cyclobutyl) substituted with one $R^{21}$ group (e.g., aryl, such as, for example, phenyl), or a cycloalkyl group (e.g., cyclopentyl or cyclohexyl) substituted with one $R^{21}$ group (e.g., aryl, such as, for example, phenyl) which in turn is substituted with one or more (e.g., one or two) independently selected $R^{22}$ groups (e.g., halo, such as, for example, F). In one example the $R^{21}$ group is bound to the same carbon of the $R^1$ group that binds the $R^1$ group to the rest of the molecule.

Examples of the cycloalkyl $R^1$ groups include, but are not limited to:

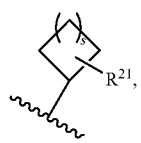

such as, for example,

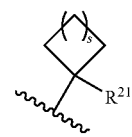

wherein s is 0 (i.e., the ring is cyclopropyl), or 1 (i.e., the ring is cyclobutyl). Examples of these $R^1$ groups include, but are not limited to:

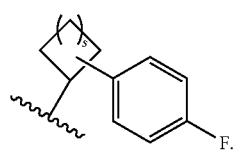

such as, for example,

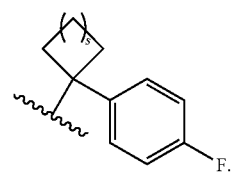

wherein s is 0 (i.e., the ring is cyclopropyl), or 1 (i.e., the ring is cyclobutyl).

Other embodiments of this invention are directed to compounds of formula (I) wherein $R^1$ is

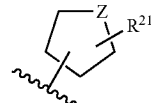

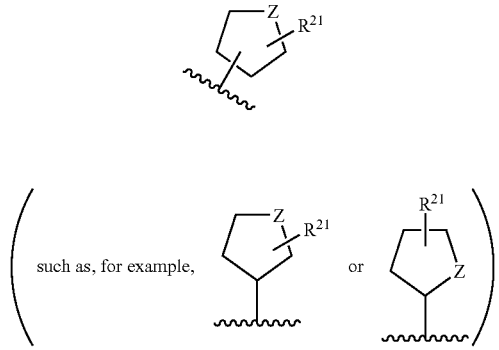

wherein Z is selected from the group consisting of: (1) —O—, (2) —NR$^{14}$—, (3) —C(R$^{21}$)$_q$— wherein q is 0, 1 or 2, and each $R^{21}$ is independently selected, (4) —C(R$^{21}$)$_q$—C(R$^{21}$)$_q$— wherein each q is independently 0, 1 or 2 and each $R^{21}$ is independently selected, (5) —(C(R$^{21}$)$_q$)$_q$—O—(C(R$^{21}$)$_q$)$_q$— wherein each q is independently 0, 1 or 2, and each $R^{21}$ is independently selected, and (6) —(C(R$^{21}$)$_q$)$_q$—N(R$^{14}$)—(C(R$^{21}$)$_q$)$_q$— wherein each q is independently 0, 1 or 2, and each $R^{21}$ is independently selected. Examples of $R^{21}$ include, but are not limited to, aryl (e.g., phenyl) and aryl (e.g., phenyl) substituted with one or more (e.g., one or two, or one) independently selected $R^{22}$ groups (e.g., halo, such as, for example, F). Examples of this $R^1$ include, but are not limited to:

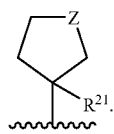

Thus, examples of this $R^1$ group include, but are not limited to:

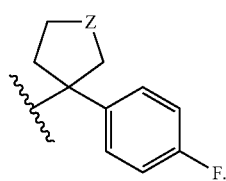

Examples of $R^1$ also include, but are not limited to:

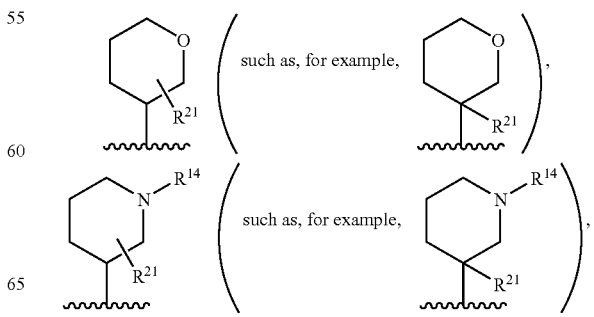

-continued

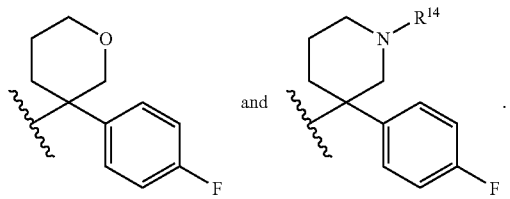

Examples of the R¹ group

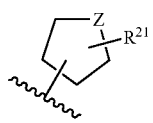

also include, but are not limited to:

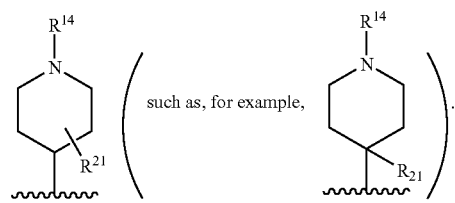

Examples of the R¹ group

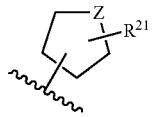

also include, but are not limited to:

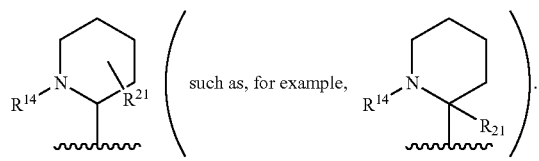

Examples of the R¹ group

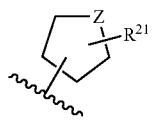

also include, but are not limited to:

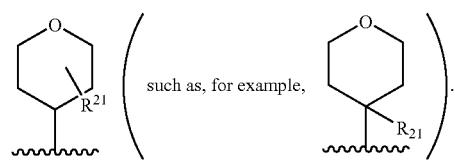

Examples of the R¹ group

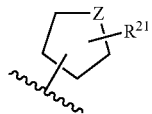

also include, but are not limited to:

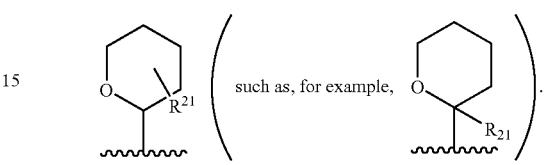

Other embodiments of this invention are directed to compounds of formula (I) wherein $R^{10}$ is aryl (e.g., phenyl) or aryl (e.g., phenyl) substituted with one or more (e.g., one or two, or one) $R^{21}$ groups (e.g., —$OR^{15}$, wherein, for example, $R^{15}$ is alkyl, such as, for example, methyl), and $R^9$ is heteroaryl (e.g., imidazolyl) or heteroaryl (e.g., imidazolyl) substituted with one or more (e.g., one or two, or one) $R^{21}$ groups (e.g., alkyl, such as, for example, methyl).

Other embodiments of this invention are directed to the compounds of formula (I) wherein $R^{10}$ is heteroaryl or heteroaryl substituted with one or more $R^{21}$ groups, and $R^9$ is heteroaryl (e.g., imidazolyl) or heteroaryl (e.g., imidazolyl) substituted with one or more (e.g., one or two, or one) $R^{21}$ groups (e.g., alkyl, such as, for example, methyl).

In another embodiment of the compounds of formula (I) $R^{10}$ is aryl substituted with one $R^{21}$ group, wherein said $R^{21}$ group is —$OR^{15}$. In one example, $R^{15}$ is alkyl. In another example $R^{15}$ is methyl.

In another embodiment of the compounds of formula (I) $R^{10}$ is phenyl substituted with one $R^{21}$ group, wherein said $R^{21}$ group is —$OR^{15}$. In one example, $R^{15}$ is alkyl. In another example $R^{15}$ is methyl.

In another embodiment of the compounds of formula (I) $R^{10}$ is heteroaryl.

In another embodiment of the compounds of formula (I) $R^9$ is heteroaryl,

In another embodiment of the compounds of formula (I) $R^9$ is heteroaryl substituted with one or more (e.g., one) independently selected $R^{21}$ groups.

In another embodiment of the compounds of formula (I) $R^9$ is heteroaryl substituted with one or more (e.g., one) independently selected $R^{21}$ groups, wherein each $R^{21}$ group is the same or different alkyl group (e.g., methyl).

In another embodiment of the compounds of formula (I) $R^9$ is heteroaryl substituted with one $R^{21}$ group.

In another embodiment of the compounds of formula (I) $R^9$ is heteroaryl substituted with one $R^{21}$ group, wherein $R^{21}$ is an alkyl group (e.g., methyl).

In another embodiment of the compounds of formula (I) $R^9$ is imidazolyl.

In another embodiment of the compounds of formula (I) $R^9$ is imidazolyl substituted with one or more (e.g., one) independently selected $R^{21}$ groups.

In another embodiment of the compounds of formula (I) $R^9$ is imidazolyl substituted with one or more (e.g., one) independently selected $R^{21}$ groups, wherein each $R^{21}$ group is the same or different alkyl group (e.g., methyl).

In another embodiment of the compounds of formula (I) $R^9$ is imidazolyl substituted with one $R^{21}$ group.

In another embodiment of the compounds of formula (I) $R^9$ is imidazolyl substituted with one $R^{21}$ group, wherein $R^{21}$ is an alkyl group (e.g., methyl).

In another embodiment of the compounds of formula (I) $R^9$ is heteroaryl, optionally substituted with one or more $R^{21}$ groups, and $R^{10}$ is aryl optionally substituted with one or more (e.g., one) $R^{21}$ groups.

In another embodiment of the compounds of formula (I) $R^9$ is heteroaryl, optionally substituted with one $R^{21}$ group, and $R^{10}$ is aryl optionally substituted with one $R^{21}$ group.

In another embodiment of the compounds of formula (I) $R^9$ is heteroaryl, optionally substituted with one or more $R^{21}$ groups, and $R^{10}$ is phenyl optionally substituted with one or more (e.g., one) $R^{21}$ groups.

In another embodiment of the compounds of formula (I) $R^9$ is heteroaryl, optionally substituted with one $R^{21}$ group, and $R^{10}$ is phenyl optionally substituted with one $R^{21}$ group.

In another embodiment of the compounds of formula (I) $R^9$ is imidazolyl, optionally substituted with one or more $R^{21}$ groups, and $R^{10}$ is aryl optionally substituted with one or more (e.g., one) $R^{21}$ groups.

In another embodiment of the compounds of formula (I) $R^9$ is imidazolyl, optionally substituted with one $R^{21}$ group, and $R^{10}$ is aryl optionally substituted with one $R^{21}$ group.

In another embodiment of the compounds of formula (I) $R^9$ is imidazolyl, optionally substituted with one or more $R^{21}$ groups, and $R^{10}$ is phenyl optionally substituted with one or more (e.g., one) $R^{21}$ groups.

In another embodiment of the compounds of formula (I) $R^9$ is imidazolyl, optionally substituted with one $R^{21}$ group, and $R^{10}$ is phenyl optionally substituted with one $R^{21}$ group.

Other embodiments of the compounds of formula (I) are directed to any one of the above embodiments wherein $R^9$ is:

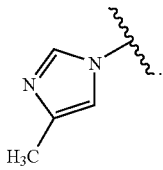

Other embodiments of the compounds of formula (I) are directed to any one of the above embodiments wherein $R^{10}$ is:

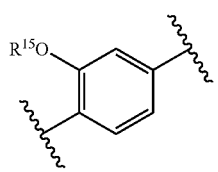

(wherein the —$OR^{15}$ is ortho to the carbon to which $R^9$ is bound to, i.e., the $R^9$-$R^{10}$— moiety is:

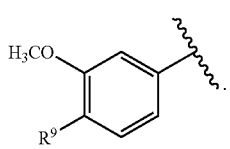

Other embodiments for the compounds of formula (I) are directed to any one of the above embodiments wherein $R^{10}$ is:

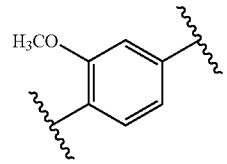 [SMILES: *c1ccc(*)c(OC)c1]

(wherein the —$OCH_3$ is ortho to the carbon to which $R^9$ is bound to, i.e., the $R^9$-$R^{10}$— moiety is:

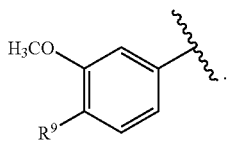

In another embodiment of the compounds of formula ($R^1$ is benzofusedcycloalkyl.

In another embodiment of the compounds of formula (I) $R^1$ is:

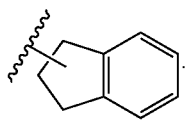

In another embodiment of the compounds of formula (I) $R^1$ is:

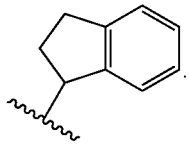 [SMILES: *C1CCc2ccccc21]

In another embodiment of the compounds of formula (I) $R^1$ is:

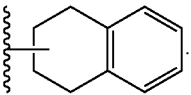

In another embodiment of the compounds of formula (I) $R^1$ is:

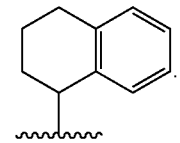

In another embodiment of the compounds of formula (I) $R^1$ is alkyl substituted with one $R^{21}$ group.

In another embodiment of the compounds of formula (I) $R^1$ is alkyl substituted with one $R^{21}$ group, and said alkyl is

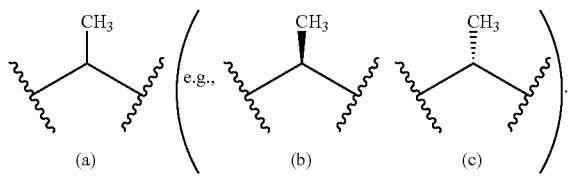

In another embodiment of the compounds of formula (I) $R^1$ is alkyl (e.g., (a), (b) or (c) described above) substituted with one $R^{21}$ group wherein said $R^{21}$ group is aryl.

In another embodiment of the compounds of formula (I) $R^1$ is alkyl (e.g., (a), (b) or (c) described above) substituted with one $R^{21}$ group wherein said $R^{21}$ group is phenyl.

In another embodiment of the compounds of formula (I) $R^1$ is alkyl (e.g., (a), (b) or (c) described above) substituted with one $R^{21}$ group wherein said $R^{21}$ group is naphthyl.

In another embodiment of the compounds of formula (I) $R^1$ is alkyl substituted with one $R^{21}$ group, and said $R^{21}$ group is substituted with two independently selected $R^{22}$ groups.

In another embodiment of the compounds of formula (I) $R^1$ is alkyl substituted with one $R^{21}$ group, and said $R^{21}$ group is substituted with one $R^{22}$ group.

In another embodiment of the compounds of formula (I) $R^1$ is alkyl substituted with one $R^{21}$ group, wherein said alkyl group is (a) (e.g., (b) or (c)), as described above, and said $R^{21}$ group is substituted with two independently selected $R^{22}$ groups.

In another embodiment of the compounds of formula (I) $R^1$ is alkyl substituted with one $R^{21}$ group, wherein said alkyl group is (a) (e.g., (b) or (c)), as described above, and said $R^{21}$ group is substituted with one $R^{22}$ group.

In another embodiment of the compounds of formula (I) $R^1$ is alkyl substituted with one $R^{21}$ group, wherein said $R^{21}$ group is aryl, and said $R^{21}$ group is substituted with two independently selected $R^{22}$ groups.

In another embodiment of the compounds of formula (I) $R^1$ is alkyl substituted with one $R^{21}$ group, wherein said $R^{21}$ group is aryl, and said $R^{21}$ group is substituted with one $R^{22}$ group.

In another embodiment of the compounds of formula (I) $R^1$ is alkyl substituted with one $R^{21}$ group, wherein said $R^{21}$ group is aryl, said alkyl group is (a) (e.g., (b) or (c)), as described above, and said $R^{21}$ group is substituted with two independently selected $R^{22}$ groups.

In another embodiment of the compounds of formula (I) $R^1$ is alkyl substituted with one $R^{21}$ group, wherein said $R^{21}$ group is aryl, wherein said alkyl group is (a) (e.g., (b) or (c)), as described above, and said $R^{21}$ group is substituted with one $R^{22}$ group.

In another embodiment of the compounds of formula (I) $R^1$ is alkyl substituted with one $R^{21}$ group, wherein said $R^{21}$ group is aryl, said $R^{21}$ group is substituted with two independently selected $R^{22}$ groups, and each $R^{22}$ is halo.

In another embodiment of the compounds of formula (I) $R^1$ is alkyl substituted with one $R^{21}$ group, wherein said $R^{21}$ group is aryl, and said $R^{21}$ group is substituted with one $R^{22}$ group, and said $R^{22}$ is halo.

In another embodiment of the compounds of formula (I) $R^1$ is alkyl substituted with one $R^{21}$ group, wherein said $R^{21}$ group is aryl, said alkyl group is (a) (e.g., (b) or (c)), as described above, and said $R^{21}$ group is substituted with two independently selected $R^{22}$ groups, and each $R^{22}$ is halo.

In another embodiment of the compounds of formula (I) $R^1$ is alkyl substituted with one $R^{21}$ group, wherein said $R^{21}$ group is aryl, wherein said alkyl group is (a) (e.g., (b) or (c)), as described above, and said $R^{21}$ group is substituted with one $R^{22}$ group. and said $R^{22}$ is halo.

In another embodiment of the compounds of formula (I) $R^1$ is alkyl substituted with: one $R^{21}$ group, wherein said $R^{21}$ group is aryl, said $R^{21}$ group is substituted with two independently selected $R^{22}$ groups, and each $R^{22}$ is F.

In another embodiment of the compounds of formula (I) $R^1$ is alkyl substituted with one $R^{21}$ group, wherein said $R^{21}$ group is aryl, and said $R^{21}$ group is substituted with one $R^{22}$ group, and said $R^{22}$ is F.

In another embodiment of the compounds of formula (I) $R^1$ is alkyl substituted with one $R^{21}$ group, wherein said $R^{21}$ group is aryl, said alkyl group is (a) (e.g., (b) or (c)), as described above, and said $R^{21}$ group is substituted with two independently selected $R^{22}$ groups, and each $R^{22}$ is F.

In another embodiment of the compounds of formula (I) $R^1$ is alkyl substituted with one $R^{21}$ group, wherein said. $R^{21}$ group is aryl, wherein said alkyl group is (a) (e.g., (b) or (c)), as described above, and said $R^{21}$ group is substituted with one $R^{22}$ group. and said $R^{22}$ is F.

In another embodiment of the compounds of formula (I) $R^1$ is:

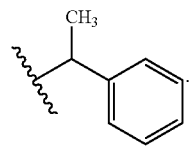 [SMILES: *C(C)c1ccccc1]

In another embodiment of the compounds of formula (I) $R^1$ is:

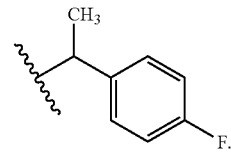 [SMILES: *C(C)c1ccc(F)cc1]

In another embodiment of the compounds of formula (I) $R^1$ is:

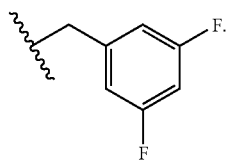 [SMILES: *Cc1cc(F)cc(F)c1]

In another embodiment of the compounds of formula (I) $R^1$ is:

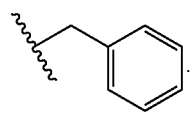 [SMILES: *Cc1ccccc1]

In another embodiment of the compounds of formula (I) $R^1$ is:

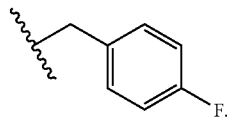 [SMILES: *Cc1ccc(F)cc1]

In another embodiment of this invention $R^1$ is:

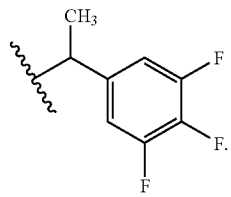 [SMILES: *C(C)c1cc(F)c(F)c(F)c1]

Other embodiments of this invention are directed to any one of the embodiments directed to $R^1$ wherein the compound of formula (I) is a compound of formula (IA).

Other embodiments of this invention are directed to any one of the embodiments directed to $R^1$ wherein the compound of formula (I) is a compound of formula (IB).

Other embodiments of this invention are directed to any one of the embodiments directed to $R^9$ wherein the compound of formula (I) is a compound of formula (IA).

Other embodiments of this invention are directed to any one of the embodiments directed to $R^9$ wherein the compound of formula (I) is a compound of formula (IB).

Other embodiments of this invention are directed to any one of the embodiments directed to $R^{10}$ wherein the compound of formula (I) is a compound of formula (IA).

Other embodiments of this invention are directed to any one of the embodiments directed to $R^{10}$ wherein the compound of formula (I) is a compound of formula (IB).

Other embodiments of this invention are directed to any one of the embodiments directed to $R^9$ and $R^{10}$ wherein the compound of formula (I) is a compound of formula (IA).

Other embodiments of this invention are directed to any one of the embodiments directed to $R^9$ and $R^{10}$ wherein the compound of formula (I) is a compound of formula (IB).

Examples of $R^{21}$ groups include —$OR^{15}$ wherein, for example, $R^{15}$ is alkyl (such as methyl or ethyl), or $R^{15}$ is cycloalkylalkyl (such as, for example, —$CH_2$-cyclopropyl), or $R^{15}$ is -alkyl-$(R^{18})_n$ (wherein, for example, said $R^{18}$ is —$OR^{20}$, and said $R^{20}$ is alkyl, and wherein examples of said -alkyl-$(R^{18})_n$ moiety is —$(CH_2)_2OCH_3$).

Examples of $R^{21}$ also include —$C(O)OR^{15}$ wherein, for example, $R^{15}$ is alkyl, such as, for example, methyl).

Examples of $R^{21}$ also include —$C(O)NR^{15}R^{16}$, wherein, for example, one of $R^{15}$ or $R^{16}$ is H, and the other is selected from the group consisting of: $(R^{18})_n$-arylalkyl-, $(R^{18})_n$-alkyl-, and cycloalkyl. In one example of this —$C(O)NR^{15}R^{16}$ moiety the $R^{18}$ is —$OR^{20}$, n is 1, $R^{20}$ is alkyl, said cycloalkyl is cyclobutyl, and said arylalkyl- is benzyl.

Examples of $R^{21}$ also include halo (e.g., Br, Cl or F).

Examples of $R^{21}$ also include arylalkyl, such as, for example, benzyl.

Other embodiments of this invention are directed to any one of the embodiments for formula (I) wherein the formula is formula (IA).

Other embodiments of this invention are directed to any one of the embodiments for formula (I) wherein the formula is formula (IB).

In another embodiment of this invention the optional bond between $G^1$ and $G^2$ in formula (IA) is absent (i.e., there is a single bond between $G^1$ and $G^2$).

In another embodiment of this invention the optional bond between $G^1$ and $G^2$ in formula (IA) is present (i.e., there is a double bond between $G^1$ and $G^2$).

In another embodiment of this invention the optional bond between $G^1$ and $G^2$ in formula (IB) is absent (i.e., there is a single bond between $G^1$ and $G^2$).

In another embodiment of this invention the optional bond between $G^1$ and $G^2$ in formula (IB) is present (i.e., there is a double bond between $G^1$ and $G^2$).

Another embodiment of this invention is directed to compounds of formula (I) having the formula:

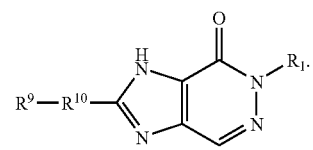

43A

In one embodiment of this invention $R^1$ in compound 43A is aryl or substituted aryl. In another embodiment $R^1$ in compound 43A is phenyl or substituted phenyl. In another embodiment $R^1$ in compound 43A is phenyl substituted with 1 to 3 independently selected $R^{21}$ groups. In another embodiment of this invention $R^1$ in compound 43A is phenyl substituted with 1 to 3 (e.g., 1 to 3, or 1 to 2, or 1) independently selected halos. In another embodiment of this invention $R^1$ in compound 43A is phenyl substituted with 1 to 3 (e.g., 1 to 3, or 1 to 2, or 1) F atoms. In another embodiment of this invention $R^1$ in compound 43A is phenyl substituted with 1 F atom.

Another embodiment of this invention is directed to compounds of formula (I) having the formula:

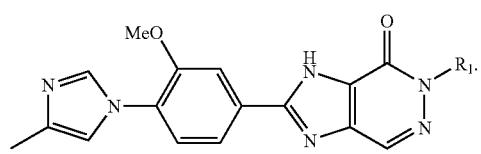

43

In one embodiment of this invention $R^1$ in compound 43 is aryl or substituted aryl. In another embodiment $R^1$ in compound 43 is phenyl or substituted phenyl. In another embodiment $R^1$ in compound 43 is phenyl substituted with 1 to 3 independently selected $R^{21}$ groups. In another embodiment of this invention $R^1$ in compound 43 is phenyl substituted with 1 to 3 (e.g., 1 to 3, or 1 to 2, or 1) independently selected halos. In another embodiment of this invention $R^1$ in compound 43 is phenyl substituted with 1 to 3 (e.g., 1 to 3, or 1 to 2, or 1) F atoms. In another embodiment of this invention $R^1$ in compound 43 is phenyl substituted with 1 F atom.

Another embodiment of this invention is directed to compounds of formula (I) having the formula:

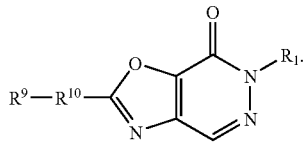
44A

In one embodiment of this invention R in compound 44A is aryl or substituted aryl. In another embodiment $R^1$ in compound 44A is phenyl or substituted phenyl. In another embodiment $R^1$ in compound 44A is phenyl substituted with 1 to 3 independently selected $R^{21}$ groups. In another embodiment of this invention $R^1$ in compound 44A is phenyl substituted with 1 to 3 (e.g., 1 to 3, or 1 to 2, or 1) independently selected halos. In another embodiment of this invention $R^1$ in compound 44A is phenyl substituted with 1 to 3 (e.g., 1 to 3, or 1 to 2, or 1) F atoms. In another embodiment of this invention $R^1$ in compound 44A is phenyl substituted with 1 F atom.

Another embodiment of this invention is directed to compounds of formula formula (I) having the formula:

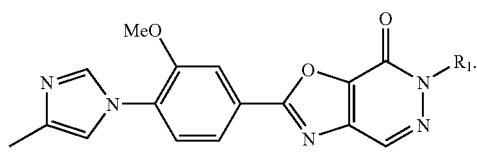
44

In one embodiment of this invention $R^1$ in compound 44 is aryl or substituted aryl. In another embodiment $R^1$ in compound 44 is phenyl or substituted phenyl. In another embodiment $R^1$ in compound 44 is phenyl substituted with 1 to 3 independently selected $R^{21}$ groups. In another embodiment of this invention $R^1$ in compound 44 is phenyl substituted with 1 to 3 (e.g., 1 to 3, or 1 to 2, or 1) independently selected halos. In another embodiment of this invention $R^1$ in compound 44 is phenyl substituted with 1 to 3 (e.g., 1 to 3, or 1 to 2, or 1) F atoms. In another embodiment of this invention $R^1$ in compound 44 is phenyl substituted with 1 F atom.

Another embodiment of this invention is directed to compounds of formula formula (I) having the formula:

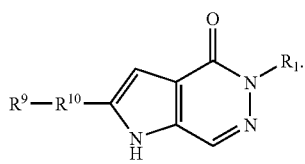
45A

In one embodiment of this invention R in compound 45A is aryl or substituted aryl. In another embodiment $R^1$ in compound 45A is phenyl or substituted phenyl. In another embodiment $R^1$ in compound 45A is phenyl substituted with 1 to 3 independently selected $R^{21}$ groups. In another embodiment of this invention $R^1$ in compound 45A is phenyl substituted with 1 to 3 (e.g., 1 to 3, or 1 to 2, or 1) independently selected halos. In another embodiment of this invention $R^1$ in compound 45A is phenyl substituted with 1 to 3 (e.g., 1 to 3, or 1 to 2, or 1) F atoms. In another embodiment of this invention $R^1$ in compound 45A is phenyl substituted with 1 F atom.

Another embodiment of this invention is directed to compounds of formula formula (I) having the formula:

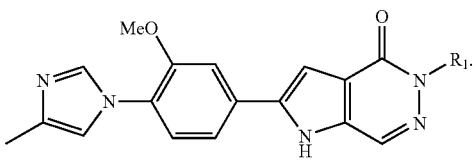
45

In one embodiment of this invention $R^1$ in compound 45 is aryl or substituted aryl. In another embodiment $R^1$ in compound 45 is phenyl or substituted phenyl. In another embodiment $R^1$ in compound 45 is phenyl substituted with 1 to 3 independently selected $R^{21}$ groups. In another embodiment of this invention $R^1$ in compound 45 is phenyl substituted with 1 to 3 (e.g., 1 to 3, or 1 to 2, or 1) independently selected halos. In another embodiment of this invention $R^1$ in compound 45 is phenyl substituted with 1 to 3 (e.g., 1 to 3, or 1 to 2, or 1) F atoms. In another embodiment of this invention $R^1$ in compound 45 is phenyl substituted with 1 F atom.

Another embodiment of this invention is directed to compounds of formula formula (I) having the formula:

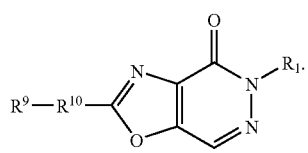
46A

In one embodiment of this invention $R^1$ in compound 46A is aryl or substituted aryl. In another embodiment $R^1$ in compound 46A is phenyl or substituted phenyl. In another embodiment $R^1$ in compound 46A is phenyl substituted with 1 to 3 independently selected $R^{21}$ groups. In another embodiment of this invention $R^1$ in compound 46A is phenyl substituted with 1 to 3 (e.g., 1 to 3, or 1 to 2, or 1) independently selected halos. In another embodiment of this invention $R^1$ in compound 46A is phenyl substituted with 1 to 3 (e.g., 1 to 3, or 1 to 2, or 1) F atoms. In another embodiment of this invention $R^1$ in compound 46A is phenyl substituted with 1 F atom.

Another embodiment of this invention is directed to compounds of formula formula (I) having the formula:

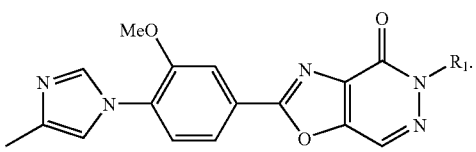
46

In one embodiment of this invention $R^1$ in compound 46 is aryl or substituted aryl. In another embodiment $R^1$ in compound 46 is phenyl or substituted phenyl. In another embodiment $R^1$ in compound 46 is phenyl substituted with 1 to 3 independently selected $R^{21}$ groups. In another embodiment of this invention $R^1$ in compound 46 is phenyl substituted with 1 to 3 (e.g., 1 to 3, or 1 to 2, or 1) independently selected halos. In another embodiment of this invention R¹ in compound 46 is phenyl substituted with 1 to 3 (e.g., 1 to 3, or 1 to 2, or 1) F atoms. In another embodiment of this invention R¹ in compound 46 is phenyl substituted with 1 F atom.

Another embodiment of this invention is directed to compounds of formula formula (I) having the formula:

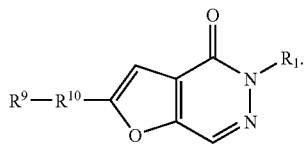
47A

In one embodiment of this invention R¹ in compound 47A is aryl or substituted aryl. In another embodiment R¹ in compound 47A is phenyl or substituted phenyl. In another embodiment R¹ in compound 47A is phenyl substituted with 1 to 3 independently selected R²¹ groups. In another embodiment of this invention R¹ in compound 47A is phenyl substituted with 1 to 3 (e.g., 1 to 3, or 1 to 2, or 1) independently selected halos. In another embodiment of this invention R¹ in compound 47A is phenyl substituted with 1 to 3 (e.g., 1 to 3, or 1 to 2, or 1) F atoms. In another embodiment of this invention R¹ in compound 47A is phenyl substituted with 1 F atom.

Another embodiment of this invention is directed to compounds of formula formula (I) having the formula:

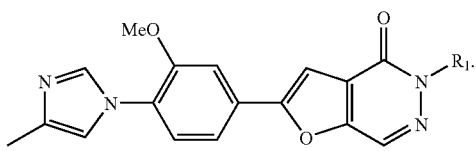
47

In one embodiment of this invention R¹ in compound 47 is aryl or substituted aryl. In another embodiment R¹ in compound 47 is phenyl or substituted phenyl. In another embodiment R¹ in compound 47 is phenyl substituted with 1 to 3 independently selected R²¹ groups. In another embodiment of this invention R¹ in compound 47 is phenyl substituted with 1 to 3 (e.g., 1 to 3, or 1 to 2, or 1) independently selected halos. In another embodiment of this invention R¹ in compound 47 is phenyl substituted with 1 to 3 (e.g., 1 to 3, or 1 to 2, or 1) F atoms. In another embodiment of this invention R¹ in compound 47 is phenyl substituted with 1 F atom.

Another embodiment of this invention is directed to compounds of formula formula (I) having the formula:

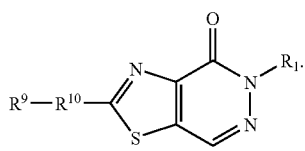
48A

In one embodiment of this invention R¹ in compound 48A is aryl or substituted aryl. In another embodiment R¹ in compound 48A is phenyl or substituted phenyl. In another embodiment R¹ in compound 48A is phenyl substituted with 1 to 3 independently selected R²¹ groups. In another embodiment of this invention R¹ in compound 48A is phenyl substituted with 1 to 3 (e.g., 1 to 3, or 1 to 2, or 1) independently selected halos. In another embodiment of this invention R¹ in compound 48A is phenyl substituted with 1 to 3 (e.g., 1 to 3, or 1 to 2, or 1) F atoms. In another embodiment of this invention R¹ in compound 48A is phenyl substituted with 1 F atom.

Another embodiment of this invention is directed to compounds of formula formula (I) having the formula:

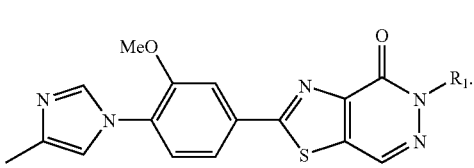
48

In one embodiment of this invention R¹ in compound 48 is aryl or substituted aryl. In another embodiment R¹ in compound 48 is phenyl or substituted phenyl. In another embodiment R¹ in compound 48 is phenyl substituted with 1 to 3 independently selected R²¹ groups. In another embodiment of this invention R¹ in compound 48 is phenyl substituted with 1 to 3 (e.g., 1 to 3, or 1 to 2, or 1) independently selected halos. In another embodiment of this invention R¹ in compound 48 is phenyl substituted with 1 to 3 (e.g., 1 to 3, or 1 to 2, or 1) F atoms. In another embodiment of this invention R¹ in compound 48 is phenyl substituted with 1 F atom.

Another embodiment of this invention is directed to compounds of formula (formula (I) having the formula:

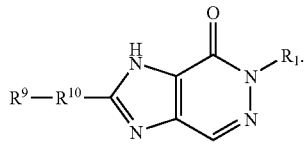
49A

In one embodiment of this invention R¹ in compound 49A is aryl or substituted aryl. In another embodiment R¹ in compound 49A is phenyl or substituted phenyl. In another embodiment R¹ in compound 49A is phenyl substituted with 1 to 3 independently selected R²¹ groups. In another embodiment R¹ in compound 49A is phenyl substituted with 1 to 3 (e.g., 1 to 3, or 1 to 2, or 1) independently selected halos. In another embodiment of this invention R¹ in compound 49A is phenyl substituted with 1 to 3 (e.g., 1 to 3, or 1 to 2, or 1) F atoms. In another embodiment of this invention R¹ in compound 49A is phenyl substituted with 1 F atom.

Another embodiment of this invention is directed to compounds of formula formula (I) having the formula:

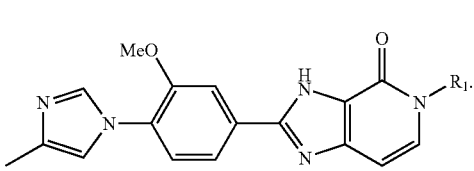
49

In one embodiment of this invention R¹ in compound 49 is aryl or substituted aryl. In another embodiment R¹ in compound 49 is phenyl or substituted phenyl. In another embodiment R¹ in compound 49 is phenyl substituted with 1 to 3 independently selected R²¹ groups. In another embodiment of this invention $R^1$ in compound 49 is phenyl substituted with 1 to 3 (e.g., 1 to 3, or 1 to 2, or 1) independently selected halos. In another embodiment of this invention $R^1$ in compound 49 is phenyl substituted with 1 to 3 (e.g., 1 to 3, or 1 to 2, or 1) F atoms. In another embodiment of this invention $R^1$ in compound 49 is phenyl substituted with 1 F atom.

Another embodiment of this invention is directed to compounds of formula formula (I) having the formula:

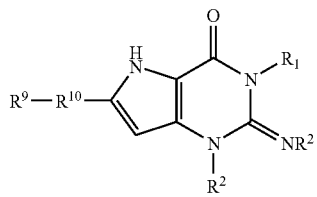

50A wherein each $R^2$ is independently selected. In one embodiment of this invention $R^1$ in compound 50A is aryl or substituted aryl. In another embodiment $R^1$ in compound 50A is phenyl or substituted phenyl. In another embodiment $R^1$ in compound 50A is phenyl substituted with 1 to 3 independently selected $R^{21}$ groups. In another embodiment of this invention $R^1$ in compound 50A is phenyl substituted with 1 to 3 (e.g., 1 to 3, or 1 to 2, or 1) independently selected halos. In another embodiment of this invention $R^1$ in compound 50A is phenyl substituted with 1 to 3 (e.g., 1 to 3, or 1 to 2, or 1) F atoms. In another embodiment of this invention $R^1$ in compound 50A is phenyl substituted with 1 F atom.

Another embodiment of this invention is directed to compounds of formula formula (I) having the formula:

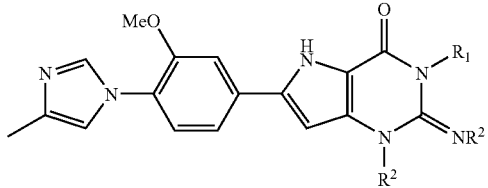

50 wherein each $R^2$ is independently selected. In one embodiment of this invention $R^1$ in compound 50 is aryl or substituted aryl. In another embodiment $R^1$ in compound 50 is phenyl or substituted phenyl. In another embodiment $R^1$ in compound 50 is phenyl substituted with 1 to 3 independently selected $R^{21}$ groups. In another embodiment of this invention $R^1$ in compound 50 is phenyl substituted with 1 to 3 (e.g., 1 to 3, or 1 to 2, or 1) independently selected halos. In another embodiment of this invention $R^1$ in compound 50 is phenyl substituted with 1 to 3 (e.g., 1 to 3, or 1 to 2, or 1) F atoms. In another embodiment of this invention $R^1$ in compound 50 is phenyl substituted with 1 F atom.

Another embodiment of this invention is directed to compounds of formula formula (I) having the formula:

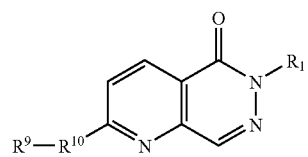

51A

In one embodiment of this invention $R^1$ in compound 51A is aryl or substituted aryl. In another embodiment $R^1$ in compound 51A is phenyl or substituted phenyl. In another embodiment $R^1$ in compound 51A is phenyl substituted with 1 to 3 independently selected $R^{21}$ groups. In another embodiment of this invention $R^1$ in compound 51A is phenyl substituted with 1 to 3 (e.g., 1 to 3, or 1 to 2, or 1) independently selected halos. In another embodiment of this invention $R^1$ in compound 51A is phenyl substituted with 1 to 3 (e.g., 1 to 3, or 1 to 2, or 1) F atoms. In another embodiment of this invention $R^1$ in compound 51A is phenyl substituted with 1 F atom.

Another embodiment of this invention is directed to compounds of formula formula (I) having the formula:

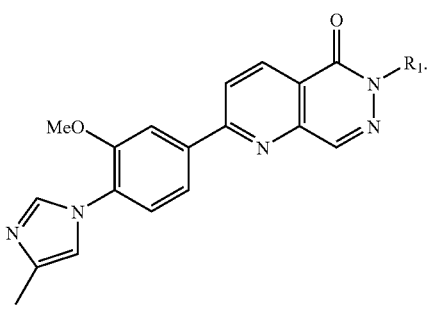

51

In one embodiment of this invention $R^1$ in compound 51 is aryl or substituted aryl. In another embodiment $R^1$ in compound 51 is phenyl or substituted phenyl. In another embodiment $R^1$ in compound 51 is phenyl substituted with 1 to 3 independently selected $R^{21}$ groups. In another embodiment of this invention $R^1$ in compound 51 is phenyl substituted with 1 to 3 (e.g., 1 to 3, or 1 to 2, or 1) independently selected halos. In another embodiment of this invention $R^1$ in compound 51 is phenyl substituted with 1 to 3 (e.g., 1 to 3, or 1 to 2, or 1) F atoms. In another embodiment of this invention $R^1$ in compound 51 is phenyl substituted with 1 F atom.

Another embodiment of this invention is directed to compounds of formula formula (I) having the formula:

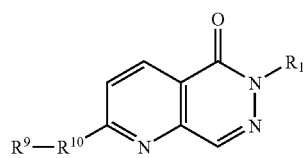

52A

In one embodiment of this invention $R^1$ in compound 52A is aryl or substituted aryl. In another embodiment $R^1$ in compound 52A is phenyl or substituted phenyl. In another embodiment $R^1$ in compound 52A is phenyl substituted with 1 to 3 independently selected $R^{21}$ groups. In another embodiment of this invention $R^1$ in compound 52A is phenyl substituted with 1 to 3 (e.g., 1 to 3, or 1 to 2, or 1) independently selected halos. In another embodiment of this invention $R^1$ in compound 52A is phenyl substituted with 1 to 3 (e.g., 1 to 3, or 1 to 2, or 1) F atoms. In another embodiment of this invention $R^1$ in compound 52A is phenyl substituted with 1 F atom.

Another embodiment of this invention is directed to compounds of formula formula (I) having the formula:

52

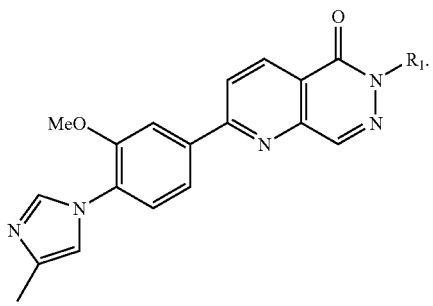

In one embodiment of this invention $R^1$ in compound 52 is aryl or substituted aryl. In another embodiment $R^1$ in compound 52 is phenyl or substituted phenyl. In another embodiment $R^1$ in compound 52 is phenyl substituted with 1 to 3 independently selected $R^{21}$ groups. In another embodiment of this invention $R^1$ in compound 52 is phenyl substituted with 1 to 3 (e.g., 1 to 3, or 1 to 2, or 1) independently selected halos. In another embodiment of this invention $R^1$ in compound 52 is phenyl substituted with 1 to 3 (e.g., 1 to 3, or 1 to 2, or 1) F atoms. In another embodiment of this invention $R^1$ in compound 52 is phenyl substituted with 1 F atom.

Another embodiment of this invention is directed to compounds of formula formula (I) having the formula:

53A

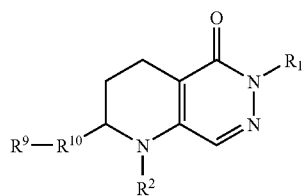

In one embodiment of this invention $R^1$ in compound 53A is aryl or substituted aryl. In another embodiment $R^1$ in compound 53A is phenyl or substituted phenyl. In another embodiment Win compound 53A is phenyl substituted with 1 to 3 independently selected $R^{21}$ groups. In another embodiment of this invention $R^1$ in compound 53A is phenyl substituted with Ito 3 (e.g., 1 to 3, or 1 to 2, or 1) independently selected halos. In another embodiment of this invention $R^1$ in compound 53A is phenyl substituted with 1 to 3 (e.g., 1 to 3, or 1 to 2, or 1) F atoms. In another embodiment of this invention $R^1$ in compound 53A is phenyl substituted with 1 F atom.

Another embodiment of this invention is directed to compounds of formula formula (I) having the formula:

53

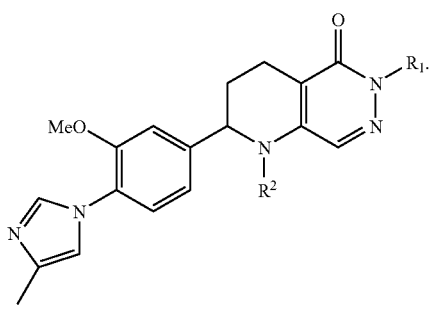

In one embodiment of this invention $R^1$ in compound 53 is aryl or substituted aryl. In another embodiment $R^1$ in compound 53 is phenyl or substituted phenyl. In another embodiment $R^1$ in compound 53 is phenyl substituted with 1 to 3 independently selected $R^{21}$ groups. In another embodiment of this invention $R^1$ in compound 53 is phenyl substituted with 1 to 3 (e.g., 1 to 3, or 1 to 2, or 1) independently selected halos. In another embodiment of this invention $R^1$ in compound 53 is phenyl substituted with 1 to 3 (e.g., 1 to 3, or 1 to 2, or 1) F atoms. In another embodiment of this invention $R^1$ in compound 53 is phenyl substituted with 1 F atom.

Another embodiment of this invention is directed to compounds of formula formula (I) having the formula:

54A

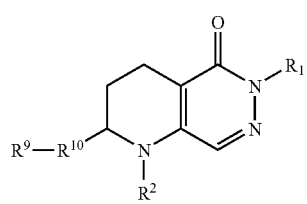

In one embodiment of this invention $R^1$ in compound 54A is aryl or substituted aryl. In another embodiment $R^1$ in compound 54A is phenyl or substituted phenyl. In another embodiment $R^1$ in compound 54A is phenyl substituted with 1 to 3 independently selected $R^{21}$ groups. In another embodiment of this invention $R^1$ in compound 54A is phenyl substituted with 1 to 3 (e.g., 1 to 3, or 1 to 2, or 1) independently selected halos. In another embodiment of this invention $R^1$ in compound 54A is phenyl substituted with 1 to 3 (e.g., 1 to 3, or 1 to 2, or 1) F atoms. In another embodiment of this invention $R^1$ in compound 54A is phenyl substituted with 1 F atom.

Another embodiment of this invention is directed to compounds of formula formula (I) having the formula:

54

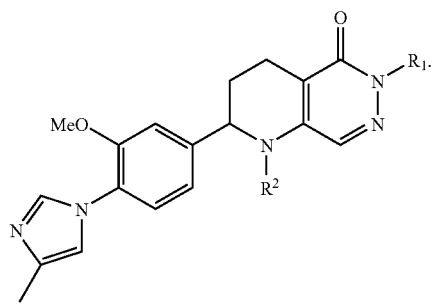

In one embodiment of this invention $R^1$ in compound 54 is aryl or substituted aryl. In another embodiment $R^1$ in compound 54 is phenyl or substituted phenyl. In another embodiment $R^1$ in compound 54 is phenyl substituted with 1 to 3 independently selected $R^{21}$ groups. In another embodiment of this invention $R^1$ in compound 54 is phenyl substituted with 1 to 3 (e.g., 1 to 3, or 1 to 2, or 1) independently selected halos. In another embodiment of this invention $R^1$ in compound 54 is phenyl substituted with 1 to 3 (e.g., 1 to 3, or 1 to 2, or 1) F atoms. In another embodiment of this invention $R^1$ in compound 54 is phenyl substituted with 1 F atom.

Examples of the $R^{21}$ moiety in the embodiments of this invention include, but are not limited to: (a) —$OR^{15}$, (b) —$OR^{15}$ wherein $R^{15}$ is alkyl, (c) —$OR^{15}$ wherein $R^{15}$ is alkyl and said alkyl is methyl or ethyl. (d) —$OR^{15}$ wherein $R^{15}$ is cycloalkylalkyl, (e) —$OR^{15}$ wherein $R^{15}$ is -alkyl-$(R^{18})_n$, (f) —$OR^{15}$ wherein $R^{15}$ is -alkyl-$(R^{18})_n$ and wherein said $R^{18}$ is —$OR^{20}$, (g) —$OR^{15}$ wherein $R^{15}$ is -alkyl-$(R^{18})_n$ and wherein said $R^{18}$ is —$OR^{20}$ and said $R^{20}$ is alkyl. Examples of the $R^{21}$ moiety include but are not limited to: —OCH₃, —OCH₂CH₃, —O(CH₂)₂OCH₃, and —CH₂-cyclopropyl.

Examples of R²¹ also include —C(O)OR¹⁵ wherein, for example, R¹⁵ is alkyl, such as, for example, methyl).

Examples of R²¹ also include —C(O)NR¹⁵R¹⁶, wherein, for example, one of R¹⁵ or R¹⁶ is H, and the other is selected from the group consisting of: (R¹⁸)ₙ-arylalkyl-, (R¹⁸)ₙ-alkyl-, and cycloalkyl. In one example of this —C(O)NR¹⁵R¹⁶ moiety the R¹⁸ is —OR²⁰, n is 1, R²⁰ is alkyl, said cycloalkyl is cyclobutyl, and said arylalkyl- is benzyl.

Examples of R²¹ also include halo (e.g., Br, Cl or F).

Examples of R²¹ also include arylalkyl, such as, for example, benzyl.

formula (I) In another embodiment of this invention the compound of formula (I) is a compound selected from the group consisting of: 43A to 54A, and 43 to 54 wherein (a) R¹ is a methyl or ethyl group substituted with one phenyl, or (b) R¹ is an methyl or ethyl group substituted with one phenyl, and said phenyl is substituted with one, two, or three F.

In another embodiment of this invention the compound of formula (I) is a compound selected from the group consisting of: 43A to 54A, and 43 to 54 wherein (a) R¹ is a methyl or ethyl group substituted with one phenyl, or (b) R¹ is an methyl or ethyl group substituted with one phenyl, and said phenyl is substituted with one, two, or three F, and (c) R¹⁰ is phenyl substituted with one —OR¹⁵ group, wherein R¹⁵ is methyl, and (e) R⁹ is selected from the group consisting of imidazolyl and imidazolyl substituted with one methyl group.

In another embodiment of this invention the compound of formula (I) is a compound selected from the group consisting of: 43A to 54A, and 43 to 54 wherein R¹ is selected from the group consisting of:

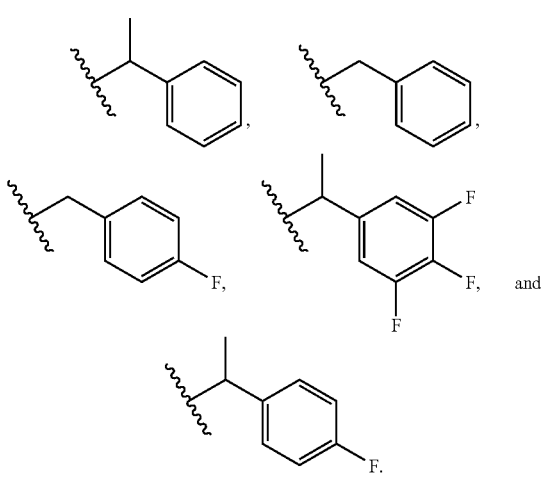

In another embodiment of this invention the compound of formula (I) is a compound selected from the group consisting of: 43A to 54A, and 43 to 54 wherein R¹ is selected from the group consisting of:

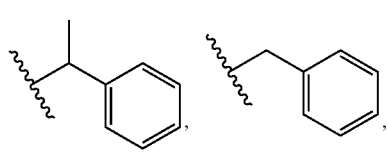

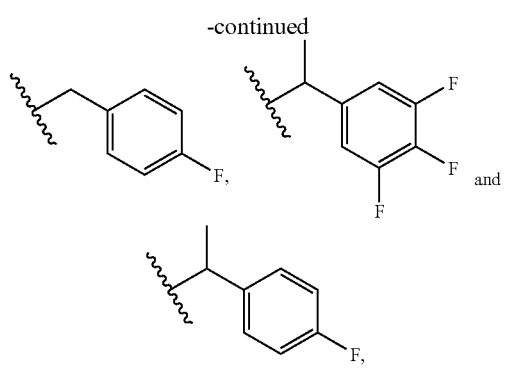

and wherein the R⁹—R¹⁰-moiety is:

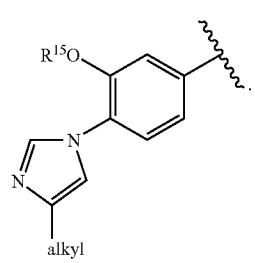

In another embodiment of this invention the compound of formula (I) is a compound selected from the group consisting of: 43A to 54A, and 43 to 54 wherein R¹ is selected from the group consisting of:

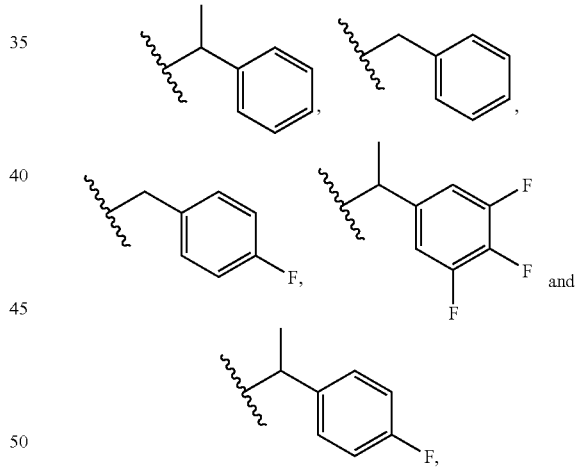

and wherein the R⁹—R¹⁰-moiety is:

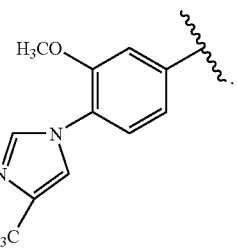

In another embodiment of this invention the compound of formula (I) is a compound selected from the group consisting of: 43A to 54A, and 43 to 54 wherein R¹ is selected from the group consisting of:

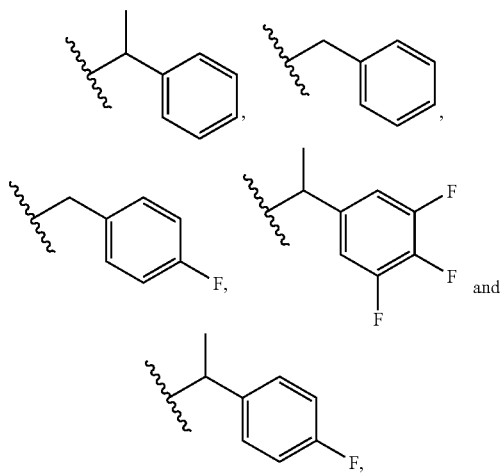

and
wherein the R⁹—R¹⁰-moiety is:

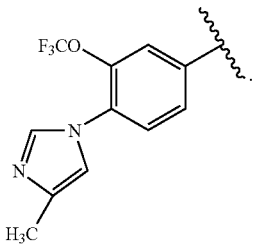 [SMILES: *c1ccc(-n2cnc(C)c2)c(OC(F)(F)F)c1]

In another embodiment of this invention the compound of formula (I) is a compound selected from the group consisting of: 43A to 54A, and 43 to 54 wherein R¹ is selected from the group consisting of:

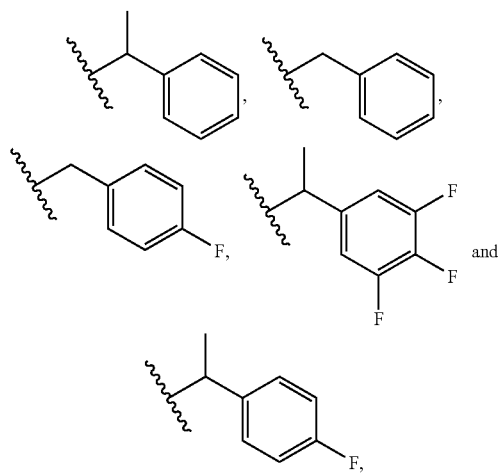

and
wherein the R⁹—R¹⁰-moiety is:

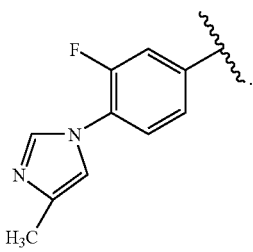 [SMILES: *c1ccc(-n2cnc(C)c2)c(F)c1]

In another embodiment of this invention the compound of formula (I) is a compound selected from the group consisting of: 43A to 54A, and 43 to 54 wherein R¹ is selected from the group consisting of:

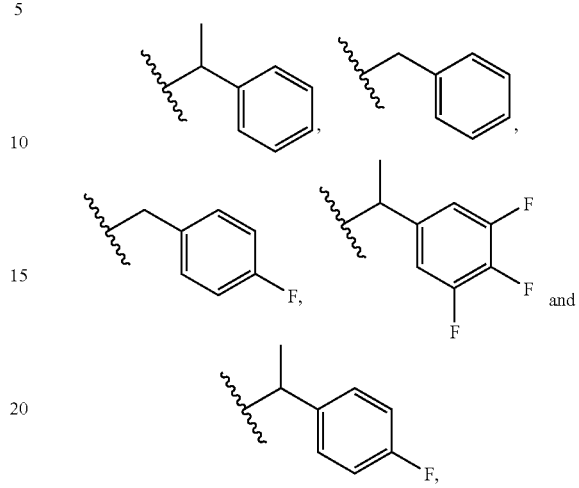

and
wherein the R⁹—R¹⁰-moiety is:

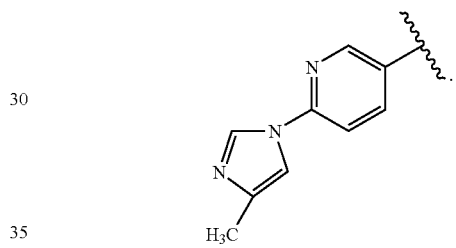

Another embodiment of this invention is directed to a compound of formula (I) selected from the group consisting of: IA, IB, IA.1, IB.1, 43A to 54A, 43 to 54, 85.1, 88.1, 91.1, and 100 to 124.

Another embodiment of this invention is directed to a compound of formula (I) selected from the group consisting of: 43A to 54A, 43 to 54, 85.1, 88.1, 91.1, and 100 to 124.

Another embodiment of this invention is directed to a compound of formula (I) selected from the group consisting of: IA, IB, IA.1, and IB.1.

Another embodiment of this invention is directed to a compound of formula (I) selected from the group consisting of: 43A to 54A.

Another embodiment of this invention is directed to a compound of formula (I) selected from the group consisting of: 43 to 54.

Another embodiment of this invention is directed to a compound of formula (I) selected from the group consisting of: 85.1, 88.1, 91.1, and 100 to 124.

Another embodiment of this invention is directed to a compound of formula (I) wherein said compound is 85.1.

Another embodiment of this invention is directed to a compound of formula (I) wherein said compound is 88.1.

Another embodiment of this invention is directed to a compound of formula (I) wherein said compound is 91.1.

Another embodiment of this invention is directed to a compound of formula (I) wherein said compound is 100.

Another embodiment of this invention is directed to a compound of formula (I) wherein said compound is 101.

Another embodiment of this invention is directed to a compound of formula (I) wherein said compound is 102.

Another embodiment of this invention is directed to a compound of formula (I) wherein said compound is 103.
Another embodiment of this invention is directed to a compound of formula (I) wherein said compound is 104.
Another embodiment of this invention is directed to a compound of formula (I) wherein said compound is 105.
Another embodiment of this invention is directed to a compound of formula (I) wherein said compound is 106.
Another embodiment of this invention is directed to a compound of formula (I) wherein said compound is 107.
Another embodiment of this invention is directed to a compound of formula (I) wherein said compound is 108.
Another embodiment of this invention is directed to a compound of formula (I) wherein said compound is 109.
Another embodiment of this invention is directed to a compound of formula (I) wherein said compound is 110.
Another embodiment of this invention is directed to a compound of formula (I) wherein said compound is 111.
Another embodiment of this invention is directed to a compound of formula (I) wherein said compound is 112.
Another embodiment of this invention is directed to a compound of formula (I) wherein said compound is 113.
Another embodiment of this invention is directed to a compound of formula (I) wherein said compound is 114.
Another embodiment of this invention is directed to a compound of formula (I) wherein said compound is 115.
Another embodiment of this invention is directed to a compound of formula (I) wherein said compound is 116.
Another embodiment of this invention is directed to a compound of formula (I) wherein said compound is 117.
Another embodiment of this invention is directed to a compound of formula (I) wherein said compound is 118.
Another embodiment of this invention is directed to a compound of formula (I) wherein said compound is 119.
Another embodiment of this invention is directed to a compound of formula (I) wherein said compound is 120.
Another embodiment of this invention is directed to a compound of formula (I) wherein said compound is 121.
Another embodiment of this invention is directed to a compound of formula (I) wherein said compound is 122.
Another embodiment of this invention is directed to a compound of formula (I) wherein said compound is 123.
Another embodiment of this invention is directed to a compound of formula (I) wherein said compound is 124.
Another embodiment of this invention is directed to a compound of formula (I) wherein said compound is IA.
Another embodiment of this invention is directed to a compound of formula (I) wherein said compound is IA.1.
Another embodiment of this invention is directed to a compound of formula (I) wherein said compound is IB.
Another embodiment of this invention is directed to a compound of formula (I) wherein said compound is IB.1.
In the embodiments below Groups A, B, C, D, E, F, G and H are as defined as follows:
(1) Group A: compounds IA, IB, IA.1, IB.1, 43A to 54A, 43 to 54, 85.1, 88.1, 91.1, and 100 to 124;
(2) Group B: compounds 43A to 54A, 43 to 54, 85.1, 88.1, 91.1, and 100 to 124;
(3) Group C: compounds IA, IB, IA.1, and IB.1;
(4) Group D: compounds 43A to 54A;
(5) Group E: compounds 43 to 54; and
(6) Group F: compounds 85.1, 88.1, 91.1, and 100 to 124.
Another embodiment of this invention is directed to a compound of formula (I).
Another embodiment of this invention is directed to a pharmaceutically acceptable salt of a compound of formula (I). And in one example the salt is a salt of a compound selected from the group consisting of Group A. And in another example the salt is a salt of a compound selected from the group consisting of Group B. And in another example the salt is a salt of a compound selected from the group consisting of Group C. And in another example the salt is a salt of a compound selected from the group consisting of Group D. And in another example the salt is a salt of a compound selected from the group consisting of Group E. And in another example the salt is a salt of a compound selected from the group consisting of Group F.

Another embodiment of this invention is directed to a pharmaceutically acceptable ester of a compound of formula (I). And in one example the ester is an ester of a compound selected from the group consisting of Group A. And in another example the ester is an ester of a compound selected from the group consisting of Group B. And in another example the ester is an ester of a compound selected from the group consisting of Group C. And in another example the ester is an ester of a compound selected from the group consisting of Group D. And in another example the ester is an ester of a compound selected from the group consisting of Group E. And in another example the ester is an ester of a compound selected from the group consisting of Group F.

Another embodiment of this invention is directed to a solvate of a compound of formula (I). And in one example the solvate is a solvate of a compound selected from the group consisting of Group A. And in another example the solvate is a solvate of a compound selected from the group consisting of Group B. And in another example the solvate is a solvate of a compound selected from the group consisting of Group C. And in another example the solvate is a solvate of a compound selected from the group consisting of Group D. And in another example the solvate is a solvate of a compound selected from the group consisting of Group E. And in another example the solvate is a solvate of a compound selected from the group consisting of Group F.

Another embodiment of this invention is directed to a compound of formula (I) in isolated form. And in one example the compound of formula (I) is selected from the group consisting of Group A. And in one example the compound of formula (I) is selected from the group consisting of Group D. And in one example the compound of formula (I) is selected from the group consisting of Group E. And in one example the compound of formula (I) is selected from the group consisting of Group F.

Another embodiment of this invention is directed to a compound of formula (I) in pure form. And in one example the compound of formula (I) is selected from the group consisting of Group A. And in one example the compound of formula (I) is selected from the group consisting of Group D. And in one example the compound of formula (I) is selected from the group consisting of Group E. And in one example the compound of formula (I) is selected from the group consisting of Group F.

Another embodiment of this invention is directed to a compound of formula (I) in pure and isolated form. And in one example the compound of formula (I) is selected from the group consisting of Group A. And in one example the compound of formula (I) is selected from the group consisting of Group D. And in one example the compound of formula (I) is selected from the group consisting of Group E. And in one example the compound of formula (I) is selected from the group consisting of Group F.

Another embodiment of this invention is directed to a pharmaceutical composition comprising an effective amount of one or more (e.g., one) compounds of Formula (I), or a pharmaceutically acceptable salt, solvate, or ester thereof, and one or more (e.g., one) pharmaceutically acceptable carriers.

Another embodiment is directed to a pharmaceutical composition comprising an effective amount of one or more (e.g., one) compounds of formula (I) and a pharmaceutically acceptable carrier.

Another embodiment is directed to a pharmaceutical composition comprising an effective amount of a pharmaceutically acceptable salt of one or more (e.g., one) compounds of formula (I) and a pharmaceutically acceptable carrier.

Another embodiment is directed to a pharmaceutical composition comprising an effective amount of a pharmaceutically acceptable ester of one or more (e.g., one) compounds of formula (I) and a pharmaceutically acceptable carrier.

Another embodiment is directed to a pharmaceutical composition comprising an effective amount of a solvate of one or more (e.g., one) compounds of formula (I) and a pharmaceutically acceptable carrier.

Another embodiment of this invention is directed to a pharmaceutical composition comprising an effective amount of one or more (e.g., one) compounds of formula (I), and an effective amount of one or more (e.g., one) other pharmaceutically active ingredients (e.g., drugs), and a pharmaceutically acceptable carrier. Examples of the other pharmaceutically active ingredients include, but are not limited to drugs selected form the group consisting of: (a) drugs useful for the treatment of Alzheimer's disease, (b) drugs useful for inhibiting the deposition of amyloid protein (e.g., amyloid beta protein) in, on or around neurological tissue (e.g., the brain), (c) drugs useful for treating neurodegenerative diseases, and (d) drugs useful for inhibiting gamma-secretase.

Another embodiment of this invention is directed to a pharmaceutical composition comprising a therapeutically effective amount of one or more (e.g. one) compounds of Formula (I), or a pharmaceutically acceptable salt, solvate, or ester thereof, and one or more (e.g., one) pharmaceutically acceptable carriers, and an effective amount of one or more compounds selected from the group consisting of cholinesterase inhibitors, Aβ antibody inhibitors, gamma secretase inhibitors and beta secretase inhibitors.

Another embodiment of this invention is directed to a pharmaceutical composition comprising an effective amount of one or more (e.g., one) compounds of formula (I), and effective amount of one or more BACE inhibitors, and a pharmaceutically acceptable carrier.

Another embodiment of this invention is directed to a pharmaceutical composition comprising an effective amount of one or more (e.g., one) compounds of formula (I), and effective amount of one or more cholinesterase inhibitors (e.g., acetyl- and/or butyrylchlolinesterase inhibitors), and a pharmaceutically acceptable carrier.

Another embodiment of this invention is directed to a pharmaceutical composition comprising an effective amount of one or more (e.g., one) compounds of formula (I).

Another embodiment of this invention is directed to a pharmaceutical composition comprising an effective amount of one or more (e.g., one) compounds of formula (I), and effective amount of one or more muscarinic antagonists (e.g., $m_1$ agonist or $m_2$ antagonists), and a pharmaceutically acceptable carrier.

Another embodiment of this invention is directed to a pharmaceutical composition comprising an effective amount of one or more (e.g., one) compounds of formula (I), and effective amount of Exelon (rivastigmine), and a pharmaceutically acceptable carrier.

Another embodiment of this invention is directed to a pharmaceutical composition comprising an effective amount of one or more (e.g., one) compounds of formula (I), and effective amount of Cognex (tacrine), and a pharmaceutically acceptable carrier.

Another embodiment of this invention is directed to a pharmaceutical composition comprising an effective amount of one or more (e.g., one) compounds of formula (I), and effective amount of a Tau kinase inhibitor, and a pharmaceutically acceptable carrier.

Another embodiment of this invention is directed to a pharmaceutical composition comprising an effective amount of one or more (e.g., one) compounds of formula (I), and effective amount of one or more Tau kinase inhibitor (e.g., GSK3beta inhibitor, cdk5 inhibitor, ERK inhibitor), and a pharmaceutically acceptable carrier.

Another embodiment of this invention is directed to a pharmaceutical composition comprising an effective amount of one or more (e.g., one) compounds of formula (I), and effective amount of one anti-Abeta vaccine (active immunization), and a pharmaceutically acceptable carrier.

Another embodiment of this invention is directed to a pharmaceutical composition comprising an effective amount of one or more (e.g., one) compounds of formula (I), and effective amount of one or more APP ligands, and a pharmaceutically acceptable carrier.

Another embodiment of this invention is directed to a pharmaceutical composition comprising an effective amount of one or more (e.g., one) compounds of formula (I), and effective amount of one or more agents that upregulate insulin degrading enzyme and/or neprilysin, and a pharmaceutically acceptable carrier.

Another embodiment of this invention is directed to a pharmaceutical composition comprising an effective amount of one or more (e.g., one) compounds of formula (I), and effective amount of one or more cholesterol lowering agents (for example, statins such as Atorvastatin, Fluvastatin, Lovastatin, Mevastatin, Pitavastatin, Pravastatin, Rosuvastatin, Simvastatin, and cholesterol absorption inhibitor such as Ezetimibe), and a pharmaceutically acceptable carrier.

Another embodiment of this invention is directed to a pharmaceutical composition comprising an effective amount of one or more (e.g., one) compounds of formula (I), and effective amount of one or more fibrates (for example, clofibrate, Clofibride, Etofibrate, Aluminium Clofibrate), and a pharmaceutically acceptable carrier Another embodiment of this invention is directed to a pharmaceutical composition comprising an effective amount of one or more (e.g., one) compounds of formula (I), and effective amount of one or more LXR agonists, and a pharmaceutically acceptable carrier.

Another embodiment of this invention is directed to a pharmaceutical composition comprising an effective amount of one or more (e.g., one) compounds of formula (I), and effective amount of one or more LRP mimics, and a pharmaceutically acceptable carrier.

Another embodiment of this invention is directed to a pharmaceutical composition comprising an effective amount of one or more (e.g., one) compounds of formula (I), and effective amount of one or more 5-HT6 receptor antagonists, and a pharmaceutically acceptable carrier.

Another embodiment of this invention is directed to a pharmaceutical composition comprising an effective amount of one or more (e.g., one) compounds of formula (I), and effective amount of one or more nicotinic receptor agonists, and a pharmaceutically acceptable carrier.

Another embodiment of this invention is directed to a pharmaceutical composition comprising an effective amount of one or more (e.g., one) compounds of formula (I), and effective amount of one or more H3 receptor antagonists, and a pharmaceutically acceptable carrier.

Another embodiment of this invention is directed to a pharmaceutical composition comprising an effective amount of one or more (e.g., one) compounds of formula (I), and effective amount of one or more histone deacetylase inhibitors, and a pharmaceutically acceptable carrier.

Another embodiment of this invention is directed to a pharmaceutical composition comprising an effective amount of one or more (e.g., one) compounds of formula (I), and effective amount of one or more hsp90 inhibitors, and a pharmaceutically acceptable carrier.

Another embodiment of this invention is directed to a pharmaceutical composition comprising an effective amount of one or more (e.g., one) compounds of formula (I), and effective amount of one or more ml muscarinic receptor agonists, and a pharmaceutically acceptable carrier.

Another embodiment of this invention is directed to combinations, i.e., a pharmaceutical composition, comprising a pharmaceutically acceptable carrier, an effective (i.e., therapeutically effective) amount of one or more compounds of formula (I), in combination with an effective (i.e., therapeutically effective) amount of one or more compounds selected from the group consisting of cholinesterase inhibitors (such as, for example, (±)-2,3-dihydro-5,6-dimethoxy-2-[[1-(phenylmethyl)-4-piperidinyl]methyl]-1H-inden-1-one hydrochloride, i.e., donepezil hydrochloride, available as the Aricept' brand of donepezil hydrochloride), Aβ antibody inhibitors, gamma secretase inhibitors and beta secretase inhibitors.

Another embodiment of this invention is directed to a pharmaceutical composition comprising an effective amount of one or more (e.g., one) compounds of formula (I), and effective amount of one or more 5-HT6 receptor antagonists mGluR1 or mGluR5 positive allosteric modulators or agonists, and a pharmaceutically acceptable carrier.

Another embodiment of this invention is directed to a pharmaceutical composition comprising an effective amount of one or more (e.g., one) compounds of formula (I), and effective amount of one or more one mGluR2/3 antagonists, and a pharmaceutically acceptable carrier.

Another embodiment of this invention is directed to a pharmaceutical composition comprising an effective amount of one or more (e.g., one) compounds of formula (I), and effective amount of one or more anti-inflammatory agents that can reduce neuroinflammation, and a pharmaceutically acceptable carrier.

Another embodiment of this invention is directed to a pharmaceutical composition comprising an effective amount of one or more (e.g., one) compounds of formula (I), and effective amount of one or more Prostaglandin EP2 receptor antagonists, and a pharmaceutically acceptable carrier.

Another embodiment of this invention is directed to a pharmaceutical composition comprising an effective amount of one or more (e.g., one) compounds of formula (I), and effective amount of one or more PAM inhibitors, and a pharmaceutically acceptable carrier.

Another embodiment of this invention is directed to a pharmaceutical composition comprising an effective amount of one or more (e.g., one) compounds of formula (I), and effective amount of one or more agents that can induce Abeta efflux such as gelsolin, and a pharmaceutically acceptable carrier.

Other embodiments of this invention are directed to any one of the above embodiments directed to pharmaceutical compositions wherein the compound of formula (I) is selected from the group consisting of Group A.

Other embodiments of this invention are directed to any one of the above embodiments directed to pharmaceutical compositions wherein the compound of formula (I) is selected from the group consisting of Group B.

Other embodiments of this invention are directed to any one of the above embodiments directed to pharmaceutical compositions wherein the compound of formula (I) is selected from the group consisting of Group C.

Other embodiments of this invention are directed to any one of the above embodiments directed to pharmaceutical compositions wherein the compound of formula (I) is selected from the group consisting of Group D.

Other embodiments of this invention are directed to any one of the above embodiments directed to pharmaceutical compositions wherein the compound of formula (I) is selected from the group consisting of Group E.

Other embodiments of this invention are directed to any one of the above embodiments directed to pharmaceutical compositions wherein the compound of formula (I) is selected from the group consisting of Group F.

The compounds of formula (I) can be useful as gamma secretase modulators and can be useful in the treatment and prevention of diseases such as, for example, central nervous system disorders (such as Alzheimers disease and Downs Syndrome), mild cognitive impairment, glaucoma, cerebral amyloid angiopathy, stroke, dementia, microgliosis, brain inflammation, and olfactory function loss.

Another embodiment of this invention is directed to a method of treating a central nervous system disorder comprising administering a therapeutically effective amount of at least one compound of formula (I) to a patient in need of such treatment.

Another embodiment of this invention is directed to a method of treating a central nervous system disorder comprising administering a therapeutically effective amount of a pharmaceutical composition comprising a therapeutically effective amount of at least one compound of formula (I), or a pharmaceutically acceptable salt, solvate, or ester thereof, and at least one pharmaceutically acceptable carrier.

Another embodiment of this invention is directed to a method of treating a central nervous system disorder comprising administering a therapeutically effective amount of a pharmaceutical composition comprising a therapeutically effective amount of at least one compound of formula (I), or a pharmaceutically acceptable salt, solvate, or ester thereof, and at least one pharmaceutically acceptable carrier, and a therapeutically effective amount of one or more compounds selected from the group consisting of cholinesterase inhibitors, Aβ antibody inhibitors, gamma secretase inhibitors and beta secretase inhibitors.

Thus, another embodiment of this invention is directed to a method for modulating (including inhibiting, antagonizing and the like) gamma-secretase comprising administering an effective (i.e., therapeutically effective) amount of one or more (e.g., one) compounds of formula (I) to a patient in need of such treatment.

Another embodiment of this invention is directed to a method for modulating (including inhibiting, antagonizing and the like) gamma-secretase, comprising administering an effective (i.e., therapeutically effective) amount of a compound of formula (I) to a patient in need of treatment.

Another embodiment of this invention is directed to a method of treating one or more neurodegenerative diseases, comprising administering an effective (i.e., therapeutically effective) amount of one or more (e.g., one) compounds of formula (I) to a patient in need of treatment.

Another embodiment of this invention is directed to a method of treating one or more neurodegenerative diseases, comprising administering an effective (i.e., therapeutically effective) amount of a compound of formula (I) to a patient in need of treatment.

Another embodiment of this invention is directed to a method of inhibiting the deposition of amyloid protein (e.g., amyloid beta protein) in, on or around neurological tissue (e.g., the brain), comprising administering an effective (i.e., therapeutically effective) amount of one or more (e.g., one) compounds of formula (I) to a patient in need of treatment.

Another embodiment of this invention is directed to a method of inhibiting the deposition of amyloid protein (e.g., amyloid beta protein) in, on or around neurological tissue (e.g., the brain), comprising administering an effective (i.e., therapeutically effective) amount of a compound of formula (I) to a patient in need of treatment.

Another embodiment of this invention is directed to a method of treating Alzheimer's disease, comprising administering an effective (i.e., therapeutically effective) amount of one or more (e.g., one) compounds of formula (I) to a patient in need of treatment.

Another embodiment of this invention is directed to a method of treating Alzheimer's disease, comprising administering an effective (i.e., therapeutically effective) amount of a compound of formula (I) to a patient in need of treatment.

Another embodiment of this invention is directed to a method of treating Alzheimer's disease, comprising administering an effective (i.e., therapeutically effective) amount of a compound of formula (I) to a patient in need of treatment.

Another embodiment of this invention is directed to a method of treating mild cognitive impairment, glaucoma, cerebral amyloid angiopathy, stroke, dementia, microgliosis, brain inflammation, or olfactory function loss, comprising administering an effective (i.e., therapeutically effective) amount of one or more (e.g., one) compounds of formula (I) to a patient in need of treatment.

Another embodiment of this invention is directed to a method of treating mild cognitive impairment, glaucoma, cerebral amyloid angiopathy, stroke, dementia, microgliosis, brain inflammation, or olfactory function loss, comprising administering an effective (i.e., therapeutically effective) amount of a compound of formula (I) to a patient in need of treatment.

Another embodiment of this invention is directed to a method of treating mild cognitive impairment, comprising administering an effective amount of one or more (e.g., one) compounds of formula (I) to a patient in need of treatment.

Another embodiment of this invention is directed to a method of treating glaucoma, comprising administering an effective amount of one or more (e.g., one) compounds of formula (I) to a patient in need of treatment.

Another embodiment of this invention is directed to a method of treating cerebral amyloid angiopathy, comprising administering an effective amount of one or more (e.g., one) compounds of formula (I) to a patient in need of treatment.

Another embodiment of this invention is directed to a method of treating stroke, comprising administering an effective amount of one or more (e.g., one) compounds of formula (I) to a patient in need of treatment.

Another embodiment of this invention is directed to a method of treating dementia, comprising administering an effective amount of one or more (e.g., one) compounds of formula (I) to a patient in need of treatment.

Another embodiment of this invention is directed to a method of treating microgliosis, comprising administering an effective amount of one or more (e.g., one) compounds of formula (I) to a patient in need of treatment.

Another embodiment of this invention is directed to a method of treating brain inflammation, comprising administering an effective amount of one or more (e.g., one) compounds of formula (I) to a patient in need of treatment.

Another embodiment of this invention is directed to a method of treating olfactory function loss, comprising administering an effective amount of one or more (e.g., one) compounds of formula (I) to a patient in need of treatment.

Another embodiment of this invention is directed to a method of treating Downs syndrome, comprising administering an effective amount of one or more (e.g., one) compounds of formula (I) to a patient in need of treatment.

Another embodiment of this invention is directed to a method of treating Downs syndrome, comprising administering an effective amount of a compound of formula (I) to a patient in need of treatment.

Other embodiments of this invention are directed to any one of the above embodiments directed to methods of treating wherein the compound of formula (I) is selected from the group consisting of Group A.

Other embodiments of this invention are directed to any one of the above embodiments directed to methods of treating wherein the compound of formula (I) is selected from the group consisting of Group B.

Other embodiments of this invention are directed to any one of the above embodiments directed to methods of treating wherein the compound of formula (I) is selected from the group consisting of Group C.

Other embodiments of this invention are directed to any one of the above embodiments directed to methods of treating wherein the compound of formula (I) is selected from the group consisting of Group D.

Other embodiments of this invention are directed to any one of the above embodiments directed to methods of treating wherein the compound of formula (I) is selected from the group consisting of Group E.

Other embodiments of this invention are directed to any one of the above embodiments directed to methods of treating wherein the compound of formula (I) is selected from the group consisting of Group F.

This invention also provides combination therapies for (1) modulating gamma-secretase, or (2) treating one or more neurodegenerative diseases, or (3) inhibiting the deposition of amyloid protein (e.g., amyloid beta protein) in, on or around neurological tissue (e.g., the brain), or (4) treating Alzheimer's disease. The combination therapies are directed to methods comprising the administration of one or more (e.g. one) compounds of formula (I) and the administration of one or more (e.g., one) other pharmaceutical active ingredients (e.g., drugs). The compounds of formula (I) and the other drugs can be administered separately (i.e., each is in its own separate dosage form), or the compounds of formula (I) can be combined with the other drugs in the same dosage form.

Thus, other embodiments of this invention are directed to any one of the methods of treatment, or methods of inhibiting, described herein, wherein an effective amount of the compound of formula (I) is used in combination with an effective amount of one or more other pharmaceutically active ingredients (e.g., drugs). The other pharmaceutically active ingredients (i.e., drugs) are selected from the group consisting of: BACE inhibitors (beta secretase inhibitors), muscarinic antagonists (e.g., $m_1$ agonists or $m_2$ antagonists), cholinesterase inhibitors (e.g., acetyl- and/or butyrylchlolinesterase inhibitors); gamma secretase inhibitors; gamma secretase modulators; HMG-CoA reductase inhibitors; non-steroidal anti-inflammatory agents; N-methyl-D-aspartate receptor antagonists; anti-amyloid antibodies; vitamin E; nicotinic acetylcholine receptor agonists; CB1 receptor inverse agonists or CB1 receptor antagonists; an antibiotic; growth hormone secretagogues; histamine H3 antagonists; AMPA agonists; PDE4 inhibitors; $GABA_A$ inverse agonists; inhibitors of amyloid aggregation; glycogen synthase kinase beta inhibitors; promoters of alpha secretase activity; PDE-10 inhibitors; Exelon (rivastigmine); Cognex (tacrine); Tau kinase inhibitors (e.g., GSK3beta inhibitors, cdk5 inhibitors, or ERK inhibitors); anti-Abeta vaccine; APP ligands; agents that upregulate insulin cholesterol lowering agents (for example, statins such as Atorvastatin, Fluvastatin, Lovastatin, Mevastatin, Pitavastatin, Pravastatin, Rosuvastatin, Simvastatin); cholesterol absorption inhibitors (such as Ezetimibe); fibrates (such as, for example, for example, clofibrate, Clofibride, Etofibrate, and Aluminium Clofibrate); LXR agonists; LRP mimics; nicotinic receptor agonists; H3 receptor antagonists; histone deacetylase inhibitors; hsp90 inhibitors; m1 muscarinic receptor agonists; 5-HT6 receptor antagonists; mGluR1; mGluR5; positive allosteric modulators or agonists; mGluR2/3 antagonists; anti-inflammatory agents that can reduce neuroinflammation; Prostaglandin EP2 receptor antagonists; PAI-1 inhibitors; and agents that can induce Abeta efflux such as gelsolin.

Other embodiments of this invention are directed to any one of the methods of treatment, or methods of inhibiting, described herein, wherein the compound of formula (I) is used in combination with an effective amount of one or more other pharmaceutically active ingredients selected from the group consisting of: BACE inhibitors (beta secretase inhibitors), muscarinic antagonists (e.g., $m_1$ agonist or $m_2$ antagonists), cholinesterase inhibitors (e.g., acetyl- and/or butyrylchlolinesterase inhibitors); gamma secretase inhibitors; gamma secretase modulators; HMG-CoA reductase inhibitors; non-steroidal anti-inflammatory agents; N-methyl-D-aspartate receptor antagonists; anti-amyloid antibodies; vitamin E; nicotinic acetylcholine receptor agonists; CB1 receptor inverse agonists or CB1 receptor antagonists; an antibiotic; growth hormone secretagogues; histamine H3 antagonists; AMPA agonists; PDE4 inhibitors; $GABA_A$ inverse agonists; inhibitors of amyloid aggregation; glycogen synthase kinase beta inhibitors; promoters of alpha secretase activity; PDE-10 inhibitors and cholesterol absorption inhibitors (e.g., ezetimibe).

Another embodiment of this invention is directed to a method of treating Alzheimer's disease, comprising administering an effective (i.e., therapeutically effective) amount of one or more (e.g., one) compounds of formula (I), in combination with an effective (i.e., therapeutically effective) amount of one or more cholinesterase inhibitors (such as, for example, (±)-2,3-dihydro-5,6-dimethoxy-2-[[1-(phenylmethyl)-4-piperidinyl]methyl]-1H-inden-1-one hydrochloride, i.e., donepezil hydrochloride, available as the Aricept® brand of donepezil hydrochloride), to a patient in need of treatment.

Another embodiment of this invention is directed to a method of treating Alzheimer's disease, comprising administering an effective (i.e., therapeutically effective) amount of a compound of formula (I), in combination with an effective (i.e., therapeutically effective) amount of one or more (e.g., one) cholinesterase inhibitors (such as, for example, (±)-2,3-dihydro-5,6-dimethoxy-2-[[1-(phenylmethyl)-4-piperidinyl]methyl]-1H-inden-1-one hydrochloride, i.e., donepezil hydrochloride, available as the Aricept® brand of donepezil hydrochloride), to a patient in need of treatment.

Another embodiment of this invention is directed to a method of treating Alzheimer's disease, comprising administering an effective (i.e., therapeutically effective) amount of one or more (e.g., one) compounds of formula (I), in combination with an effective (i.e., therapeutically effective) amount of one or more compounds selected from the group consisting of Aβ antibody inhibitors, gamma secretase inhibitors and beta secretase inhibitors.

Another embodiment of this invention is directed to a method of treating Alzheimer's disease, comprising administering an effective (i.e., therapeutically effective) amount of one or more (e.g., one) compounds of formula (I), in combination with an effective (i.e., therapeutically effective) amount of one or more BACE inhibitors.

Another embodiment of this invention is directed to a method of treating Alzheimer's disease, comprising administering an effective amount of one or more compounds of formula (I), in combination with an effective amount of Exelon (rivastigmine).

Another embodiment of this invention is directed to a method of treating Alzheimer's disease, comprising administering an effective amount of one or more compounds of formula (I), in combination with an effective amount of Cognex (tacrine).

Another embodiment of this invention is directed to a method of treating Alzheimer's disease, comprising administering an effective amount of one or more compounds of formula (I), in combination with an effective amount of a Tau kinase inhibitor.

Another embodiment of this invention is directed to a method of treating Alzheimer's disease, comprising administering an effective amount of one or more compounds of formula (I), in combination with an effective amount of one or more Tau kinase inhibitor (e.g., GSK3beta inhibitor, cdk5 inhibitor, ERK inhibitor).

This invention also provides a method of treating Alzheimer's disease, comprising administering an effective amount of one or more compounds of formula (I), in combination with an effective amount of one anti-Abeta vaccination (active immunization).

Another embodiment of this invention is directed to a method of treating Alzheimer's disease, comprising administering an effective amount of one or more compounds of formula (I), in combination with an effective amount of one or more APP ligands.

Another embodiment of this invention is directed to a method of treating Alzheimer's disease, comprising administering an effective amount of one or more compounds of formula (I), in combination with an effective amount of one or more agents that upregulate insulin degrading enzyme and/or neprilysin.

Another embodiment of this invention is directed to a method of treating Alzheimer's disease, comprising administering an effective amount of one or more compounds of formula (I), in combination with an effective amount of one or more cholesterol lowering agents (for example, statins such as Atorvastatin, Fluvastatin, Lovastatin, Mevastatin, Pitavastatin, Pravastatin, Rosuvastatin, Simvastatin, and cholesterol absorption inhibitor such as Ezetimibe).

This invention also provides a method of treating Alzheimer's disease, comprising administering an effective amount of one or more compounds of formula (I), in combination with an effective amount of one or more fibrates (for example, clofibrate, Clofibride, Etofibrate, Aluminium Clofibrate).

Another embodiment of this invention is directed to a method of treating Alzheimer's disease, comprising administering an effective amount of one or more compounds of formula (I), in combination with an effective amount of one or more LXR agonists.

Another embodiment of this invention is directed to a method of treating Alzheimer's disease, comprising administering an effective amount of one or more compounds of formula (I), in combination with an effective amount of one or more LRP mimics.

Another embodiment of this invention is directed to a method of treating Alzheimer's disease, comprising administering an effective amount of one or more compounds of formula (I), in combination with an effective amount of one or more 5-HT6 receptor antagonists.

Another embodiment of this invention is directed to a method of treating Alzheimer's disease, comprising administering an effective amount of one or more compounds of formula (I), in combination with an effective amount of one or more nicotinic receptor agonists.

Another embodiment of this invention is directed to a method of treating Alzheimer's disease, comprising administering an effective amount of one or more compounds of formula (I), in combination with an effective amount of one or more H3 receptor antagonists.

This invention also provides a method of treating Alzheimer's disease, comprising administering an effective amount of one or more compounds of formula (I), in combination with an effective amount of one or more histone deacetylase inhibitors.

Another embodiment of this invention is directed to a method of treating Alzheimer's disease, comprising administering an effective amount of one or more compounds of formula (I), in combination with an effective amount of one or more hsp90 inhibitors.

Another embodiment of this invention is directed to a method of treating Alzheimer's disease, comprising administering an effective amount of one or more compounds of formula (I), in combination with an effective amount of one or more m1 muscarinic receptor agonists.

Another embodiment of this invention is directed to a method of treating Alzheimer's disease, comprising administering an effective amount of one or more compounds of formula (I), in combination with an effective amount of one or more 5-HT6 receptor antagonists mGluR1 or mGluR5 positive allosteric modulators or agonists.

Another embodiment of this invention is directed to a method of treating Alzheimer's disease, comprising administering an effective amount of one or more compounds of formula (I), in combination with an effective amount of one or more mGluR2/3 antagonists.

Another embodiment of this invention is directed to a method of treating Alzheimer's disease, comprising administering an effective amount of one or more compounds of formula (I), in combination with an effective amount of one or more anti-inflammatory agents that can reduce neuroinflammation.

Another embodiment of this invention is directed to a method of treating Alzheimer's disease, comprising administering an effective amount of one or more compounds of formula (I), in combination with an effective amount of one or more Prostaglandin EP2 receptor antagonists.

Another embodiment of this invention is directed to a method of treating Alzheimer's disease, comprising administering an effective amount of one or more compounds of formula (I), in combination with an effective amount of one or more PAI-1 inhibitors.

Another embodiment of this invention is directed to a method of treating Alzheimer's disease, comprising administering an effective amount of one or more compounds of formula (I), in combination with an effective amount of one or more agents that can induce Abeta efflux such as gelsolin.

Another embodiment of this invention is directed to a method of treating Downs syndrome, comprising administering an effective (i.e., therapeutically effective) amount of one or more (e.g., one) compounds of formula (I) to a patient in need of treatment.

Another embodiment of this invention is directed to a method of treating Downs syndrome, comprising administering an effective (i.e., therapeutically effective) amount of a compound of formula (I) to a patient in need of treatment.

Another embodiment of this invention is directed to a method of treating Downs syndrome, comprising administering an effective (i.e., therapeutically effective) amount of one or more (e.g., one) compounds of formula (I), in combination with an effective (i.e., therapeutically effective) amount of one or more cholinesterase inhibitors (such as, for example, (±)-2,3-dihydro-5,6-dimethoxy-2-[[1-(phenylmethyl)-4-piperidinyl]methyl]-1H-inden-1-one hydrochloride, i.e., donepezil hydrochloride, available as the Aricept® brand of donepezil hydrochloride), to a patient in need of treatment.

Another embodiment of this invention is directed to a method of treating Downs syndrome, comprising administering an effective (i.e., therapeutically effective) amount of a compound of formula (I), in combination with an effective (i.e., therapeutically effective) amount of one or more (e.g., one) cholinesterase inhibitors (such as, for example, (±)-2,3-dihydro-5,6-dimethoxy-2-[[1-(phenylmethyl)-4-piperidinyl]methyl]-1H-inden-1-one hydrochloride, i.e., donepezil hydrochloride, available as the Aricept® brand of donepezil hydrochloride), to a patient in need of treatment.

Another embodiment of this invention is directed to combinations (i.e., pharmaceutical compositions) comprising an effective (i.e., therapeutically effective) amount of one or more (e.g., one) compounds of formula (I), in combination with an effective (i.e., therapeutically effective) amount of one or more compounds selected from the group consisting of cholinesterase inhibitors (such as, for example, (±)-2,3-dihydro-5,6-dimethoxy-2-[[1-(phenylmethyl)-4-piperidinyl]methyl]-1H-inden-1-one hydrochloride, i.e., donepezil hydrochloride, available as the Aricept® brand of donepezil hydrochloride), Aβ antibody inhibitors, gamma secretase inhibitors and beta secretase inhibitors. The pharmaceutical compositions also comprise a pharmaceutically acceptable carrier.

Other embodiments of this invention are directed to any one of the above embodiments directed to combination therapies (i.e., the above methods of treating wherein compounds of formula (I) are used in combination with other pharmaceutically active ingredients, i.e., drugs) wherein the compound of formula (I) is selected from the group consisting of Group A.

Other embodiments of this invention are directed to any one of the above embodiments directed to combination therapies (i.e., the above methods of treating wherein compounds of formula (I) are used in combination with other pharmaceutically active ingredients, i.e., drugs) wherein the compound of formula (I) is selected from the group consisting of Group B.

Other embodiments of this invention are directed to any one of the above embodiments directed to combination therapies (i.e., the above methods of treating wherein compounds of formula (I) are used in combination with other pharmaceutically active ingredients, i.e., drugs) wherein the compound of formula (I) is selected from the group consisting of Group C.

Other embodiments of this invention are directed to any one of the above embodiments directed to combination therapies (i.e., the above methods of treating wherein compounds of formula (I) are used in combination with other pharmaceutically active ingredients, i.e., drugs) wherein the compound of formula (I) is selected from the group consisting of Group D.

Other embodiments of this invention are directed to any one of the above embodiments directed to combination therapies (i.e., the above methods of treating wherein compounds of formula (I) are used in combination with other pharmaceutically active ingredients, i.e., drugs) wherein the compound of formula (I) is selected from the group consisting of Group E.

Other embodiments of this invention are directed to any one of the above embodiments directed to combination therapies (i.e., the above methods of treating wherein compounds of formula (I) are used in combination with other pharmaceutically active ingredients, i.e., drugs) wherein the compound of formula (I) is selected from the group consisting of Group F.

Another embodiment of this invention is directed to a kit comprising, in separate containers, in a single package, pharmaceutical compositions for use in combination, wherein one container comprises an effective amount of a compound of formula (I) in a pharmaceutically acceptable carrier, and another container (i.e., a second container) comprises an effective amount of another pharmaceutically active ingredient (as described above), the combined quantities of the compound of formula (I) and the other pharmaceutically active ingredient being effective to: (a) treat Alzheimer's disease, or (b) inhibit the deposition of amyloid protein (e.g., amyloid beta protein) in, on or around neurological tissue (e.g., the brain), or (c) treat neurodegenerative diseases, or (d) modulate the activity of gamma-secretase, or (e) mild cognitive impairment, or (f) glaucoma, or (g) cerebral amyloid angiopathy, or (h) stroke, or (i) dementia, or (j) microgliosis, or (k) brain inflammation, or (l) olfactory function loss.

Another embodiment of this invention is directed to a kit comprising, in separate containers, in a single package, pharmaceutical compositions for use in combination, wherein one container comprises an effective amount of one or more (e.g., one) compounds of formula (I) in a pharmaceutically acceptable carrier, and another container (i.e., a second container) comprises an effective amount of another pharmaceutically active ingredient (as described above), the combined quantities of the compounds of formula (I) and the other pharmaceutically active ingredient being effective to: (a) treat Alzheimer's disease, or (b) inhibit the deposition of amyloid protein (e.g., amyloid beta protein) in, on or around neurological tissue (e.g., the brain), or (c) treat neurodegenerative diseases, or (d) modulate the activity of gamma-secretase.

Another embodiment of this invention is directed to a kit comprising, in separate containers, in a single package, pharmaceutical compositions for use in combination, wherein one container comprises an effective amount of a compound of formula (I) in a pharmaceutically acceptable carrier, and another container (i.e., a second container) comprises an effective amount of another pharmaceutically active ingredient (as described above), the combined quantities of the compound of formula (I) and the other pharmaceutically active ingredient being effective to: (a) treat Alzheimer's disease, or (b) inhibit the deposition of amyloid protein (e.g., amyloid beta protein) in, on or around neurological tissue (e.g., the brain), or (c) treat neurodegenerative diseases, or (d) modulate the activity of gamma-secretase.

Other embodiments of this invention are directed to any one of the above embodiments directed to kits wherein the compound of formula (I) is selected from the group consisting of Group A.

Other embodiments of this invention are directed to any one of the above embodiments directed to kits wherein the compound of formula (I) is selected from the group consisting of Group B.

Other embodiments of this invention are directed to any one of the above embodiments directed to kits wherein the compound of formula (I) is selected from the group consisting of Group C.

Other embodiments of this invention are directed to any one of the above embodiments directed to kits wherein the compound of formula (I) is selected from the group consisting of Group D.

Other embodiments of this invention are directed to any one of the above embodiments directed to kits wherein the compound of formula (I) is selected from the group consisting of Group E.

Other embodiments of this invention are directed to any one of the above embodiments directed to kits wherein the compound of formula (I) is selected from the group consisting of Group F.

Examples of cholinesterase inhibitors are tacrine, donepezil, rivastigmine, galantamine, pyridostigmine and neostigmine, with tacrine, donepezil, rivastigmine and galantamine being preferred.

Examples of $m_1$ agonists are known in the art. Examples of $m_2$ antagonists are also known in the art; in particular, $m_2$ antagonists are disclosed in U.S. Pat. Nos. 5,883,096; 6,037,352; 5,889,006; 6,043,255; 5,952,349; 5,935,958; 6,066,636; 5,977,138; 6,294,554; 6,043,255; and 6,458,812; and in WO 03/031412, all of which are incorporated herein by reference.

Examples of BACE inhibitors include those described in: US2005/0119227 published Jun. 2, 2005 (see also WO2005/016876 published Feb. 24, 2005), US2005/0043290 published Feb. 24, 2005 (see also WO2005/014540 published Feb. 17, 2005), WO2005/058311 published Jun. 30, 2005 (see also US2007/0072852 published Mar. 29, 2007), US2006/0111370 published May 25, 2006 (see also WO2006/065277 published Jun. 22, 2006), U.S. application Ser. No. 11/710,582 filed Feb. 23, 2007, US2006/0040994 published Feb. 23, 2006 (see also WO2006/014762 published Feb. 9, 2006), WO2006/014944 published Feb. 9, 2006 (see also US2006/0040948 published Feb. 23, 2006), WO2006/138266 published Dec. 28, 2006 (see also US2007/0010667 published Jan. 11, 2007), WO2006/138265 published Dec. 28, 2006, WO2006/138230 published Dec. 28, 2006, WO2006/138195 published Dec. 28, 2006 (see also US2006/0281729 published Dec. 14, 2006), WO2006/138264 published Dec. 28, 2006 (see also US2007/0060575 published Mar. 15, 2007), WO2006/138192 published Dec. 28, 2006 (see also US2006/0281730 published Dec. 14, 2006), WO2006/138217 published Dec. 28, 2006 (see also US2006/0287294 published Dec. 21, 2006), US2007/0099898 published May 3, 200 (see also WO2007/050721 published May 3, 2007), WO2007/053506 published May 10, 2007 (see also US2007/099875 published May 3, 2007), U.S. application Ser. No. 11/759,336 filed Jun. 7, 2007, U.S. Application Ser. No. 60/874,362 filed Dec. 12, 2006, and U.S. Application Ser. No. 60/874,419 filed Dec. 12, 2006, the disclosures of each being incorporated herein by reference thereto.

It is noted that the carbons of formula (I) and other formulas herein may be replaced with 1 to 3 silicon atoms so long as all valency requirements are satisfied.

As used above, and throughout this disclosure, the following terms, unless otherwise indicated, shall be understood to have the following meanings:

"Patient" includes both human and animals.

"Mammal" means humans and other mammalian animals.

"One or more" means that there is at least one and there can be more than one, and examples include 1, 2 or 3, or 1 and 2, or 1.

"At least one" means there is at least one and there can be more than one, and examples include 1, 2 or 3, or 1 and 2, or 1.

"Bn" means benzyl.

"CAN" means ceric ammonium nitrate.

"EDCI" means (3-(dimethylamino)propyl)ethyl carbodiimide hydrochloride.

"Et" means ethyl.

"HOBT" means 1-hydroxybenzotriazole.

"i-pr" means isopropyl.

"Me" means methyl.

"PMB" means p-methoxybenzyl.

"PMBO" means p-methoxybenzyloxy.

"Pr" means propyl.

"PTSA" means p-toluene sulfonic acid.

"t-Bu" means tert-butyl.

"Fused benzocycloalkyl ring" means a phenyl ring fused to a cycloalkyl ring (as cycloalkyl is defined below), such as, for example,

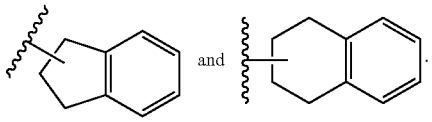

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. "Alkyl" may be unsubstituted or optionally substituted by one or more substituents which may be the same or different, each substituent being independently selected from the group consisting of halo, alkyl, aryl, cycloalkyl, cyano, hydroxy, alkoxy, alkylthio, amino, oxime (e.g., =N—ON), —NH(alkyl), —NH(cycloalkyl), —N(alkyl)$_2$, —O—C(O)-alkyl, —O—C(O)-aryl, —O—C(O)-cycloalkyl, carboxy and —C(O)O-alkyl. Non-limiting examples of suitable alkyl groups include methyl, ethyl, n-propyl, isopropyl and t-butyl.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. "Alkenyl" may be unsubstituted or optionally substituted by one or more substituents which may be the same or different, each substituent being independently selected from the group consisting of halo, alkyl. aryl, cycloalkyl, cyano, alkoxy and —S(alkyl), Non-limiting examples of suitable alkenyl groups include ethenyl, propenyl, n-butenyl, 3-methylbut-2-enyl, n-pentenyl, octenyl and decenyl.

"Alkylene" means a difunctional group obtained by removal of a hydrogen atom from an alkyl group that is defined above. Non-limiting examples of alkylene include methylene, ethylene and propylene.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl and 3-methylbutynyl. "Alkynyl" may be unsubstituted or optionally substituted by one or more substituents which may be the same or different, each substituent being independently selected from the group consisting of alkyl, aryl and cycloalkyl.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. "Heteroaryl" may also include a heteroaryl as defined above fused to an aryl as defined above. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like.

"Aralkyl" or "arylalkyl" means an aryl-alkyl-group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Alkylaryl" means an alkyl-aryl-group in which the alkyl and aryl are as previously described. Preferred alkylaryls comprise a lower alkyl group. Non-limiting example of a suitable alkylaryl group is tolyl. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like.

"Cycloalkylalkyl" means a cycloalkyl moiety as defined above linked via an alkyl moiety (defined above) to a parent core. Non-limiting examples of suitable cycloalkylalkyls include cyclohexylmethyl, adamantylmethyl and the like.

"Cycloalkenyl" means a non-aromatic mono or multicyclic ring system comprising about 3 to about 10 carbon atoms, preferably about 5 to about 10 carbon atoms which contains at least one carbon-carbon double bond. Preferred cycloalkenyl rings contain about 5 to about 7 ring atoms. The cycloalkenyl can be optionally substituted with one or more "ring system substituents" which may be the same or different, and are as defined above. Non-limiting examples of suitable monocyclic cycloalkenyls include cyclopentenyl, cyclohexenyl, cyclohepta-1,3-dienyl, and the like, Non-limiting example of a suitable multicyclic cycloalkenyl is norbornylenyl.

"Cycloalkenylalkyl" means a cycloalkenyl moiety as defined above linked via an alkyl moiety (defined above) to a parent core. Non-limiting examples of suitable cycloalkenylalkyls include cyclopentenylmethyl, cyclohexenylmethyl and the like.

"Halogen" means fluorine, chlorine, bromine, or iodine. Preferred are fluorine, chlorine and bromine. "Halo" refers to fluoro, chloro, bromo or iodo.

"Ring system substituent" means a substituent attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, =O, =N—OY$_1$, —O—C(O)-aryl, —O—C(O)-cycloalkyl, —C(=N—CN)—NH$_2$, —C(=NH)—NH$_2$, —C(=NH)—NH(alkyl), oxime (e.g., =N—OH), Y$_1$Y$_2$N—, Y$_1$Y$_2$N-alkyl-, Y$_1$Y$_2$NC(O)—, Y$_1$Y$_2$NSO$_2$— and —SO$_2$NY$_1$Y$_2$, wherein Y$_1$ and Y$_2$ can be the same or different and are independently selected from the group consisting of hydrogen, alkyl, aryl, cycloalkyl, and aralkyl. "Ring system substituent" may also mean a single moiety which simultaneously replaces two available hydrogens on two adjacent carbon atoms (one H on each carbon) on a ring system. Examples of such moiety are methylene dioxy, ethylenedioxy, —C(CH$_3$)$_2$— and the like which form moieties such as, for example:

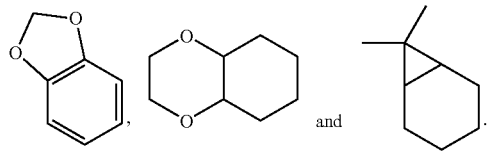

"Heteroarylalkyl" means a heteroaryl moiety as defined above linked via an alkyl moiety (defined above) to a parent core. Non-limiting examples of suitable heteroaryls include 2-pyridinylmethyl, quinolinylmethyl and the like.

"Heterocyclyl" or "heterocycloalkyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like. "Heterocyclyl" also includes rings wherein =O replaces two available hydrogens on the same carbon atom on a ring system (i.e., heterocyclyl includes rings having a carbonyl in the ring). An example of such moiety is pyrrolidone:

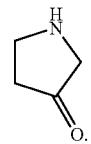

"Heterocyclylalkyl" (or "heterocycloalkylalkyl") means a heterocyclyl moiety as defined above linked via an alkyl moiety (defined above) to a parent core. Non-limiting examples of suitable heterocyclylalkyls include piperidinylmethyl, piperazinylmethyl and the like.

"Heterocyclenyl" (or "heterocycloalkenyl") means a non-aromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen or sulfur atom respectively is present as a ring atom. The heterocyclenyl can be optionally substituted by one or more ring system substituents, wherein "ring system substituent" is as defined above. The nitrogen or sulfur atom of the heterocyclenyl can be optionally oxidized to the corresponding N-oxide, S-oxide or S,S-dioxide. Non-limiting examples of suitable heterocyclenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluorodihydrofuranyl, 7-oxabicyclo[2.2.1]heptenyl, dihydrothiophenyl, dihydrothiopyranyl, and the like, "Heterocyclenyl" also includes rings wherein =O replaces two available hydrogens on the same carbon atom on a ring system (i.e., heterocyclyl includes rings having a carbonyl in the ring). An example of such moiety is pyrrolidinone:

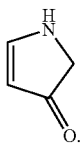

"Heterocyclenylalkyl" (or "heterocycloalkenylalkyl") means a heterocyclenyl moiety as defined above linked via an alkyl moiety (defined above) to a parent core.

It should be noted that in hetero-atom containing ring systems of this invention, there are no hydroxyl groups on carbon atoms adjacent to a N, O or S, as well as there are no N or S groups on carbon adjacent to another heteroatom. Thus, for example, in the ring:

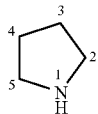

there is no —OH attached directly to carbons marked 2 and 5.

It should also be noted that tautomeric forms such as, for example, the moieties:

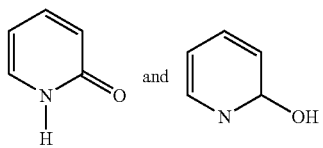 [SMILES: O=c1cccc[nH]1 ; OC1C=CC=CN1]

are considered equivalent in certain embodiments of this invention.

"Alkynylalkyl" means an alkynyl-alkyl-group in which the alkynyl and alkyl are as previously described. Preferred alkynylalkyls contain a lower alkynyl and a lower alkyl group. The bond to the parent moiety is through the alkyl. Non-limiting examples of suitable alkynylalkyl groups include propargylmethyl.

"Heteroaralkyl" means a heteroaryl-alkyl-group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Hydroxyalkyl" means a HO-alkyl-group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1-naphthoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkyloxy" means an aralkyl-O— group in which the aralkyl group is as previously described. Non-limiting examples of suitable aralkyloxy groups include benzyloxy and 1- or 2-naphthalenemethoxy. The bond to the parent moiety is through the ether oxygen.

"Alkylthio" means an alkyl-S— group in which the alkyl group is as previously described. Non-limiting examples of suitable alkylthio groups include methylthio and ethylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—CO— group, Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-S($O_2$)— group. Preferred groups are those in which the alkyl group is lower alkyl. The bond to the parent moiety is through the sulfonyl.

"Arylsulfonyl" means an aryl-S($O_2$)— group. The bond to the parent moiety is through the sulfonyl.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

The term "purified", "in purified form" or "in isolated and purified form" for a compound refers to the physical state of said compound after being isolated from a synthetic process (e.g. from a reaction mixture), or natural source or combination thereof. Thus, the term "purified", "in purified form" or "in isolated and purified form" for a compound refers to the physical state of said compound after being obtained from a purification process or processes described herein or well known to the skilled artisan (e.g., chromatography, recrystallization and the like), in sufficient purity to be characterizable by standard analytical techniques described herein or well known to the skilled artisan.

It should also be noted that any carbon as well as heteroatom with unsatisfied valences in the text, schemes, examples and Tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction, Suitable protecting groups will be recognized by those with ordinary skill in the art as well as by reference to standard textbooks such as, for example, T. W. Greene et al, *Protective Groups in organic Synthesis* (1991), Wiley, New York.

When any variable (e.g., aryl, heterocycle, $R^2$, etc.) occurs more than one time in any constituent or in Formula I, its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g., a drug precursor) that is transformed in vivo to yield a compound of Formula (I) or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of Formula (I) or a pharmaceutically acceptable salt, hydrate or solvate of the compound contains a carboxylic acid functional group, a prodrug can comprise an ester formed by the replacement of the hydrogen atom of the acid group with a group such as, for example, $(C_1-C_8)$alkyl, $(C_2-C_{12})$alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_1-C_2)$alkylamino$(C_2-C_3)$alkyl (such as β-dimethylaminoethyl), carbamoyl-$(C_1-C_2)$alkyl, N,N-di $(C_1-C_2)$alkylcarbamoyl-$(C_1-C_2)$alkyl and piperidino-, pyrrolidino- or morpholino$(C_2-C_3)$ alkyl, and the like.

Similarly, if a compound of Formula (I) contains an alcohol functional group, a prodrug can be formed by the replacement of the hydrogen atom of the alcohol group with a group such as, for example, $(C_1-C_6)$alkanoyloxymethyl, 1-$((C_1-C_6)$alkanoyloxy)ethyl, 1-methyl-1$((C_1-C_6)$alkanoyloxy)ethyl, $(C_1-C_6)$alkoxycarbonyloxymethyl, N—$(C_1-C_6)$alkoxycarbonylaminomethyl, succinoyl, $(C_1-C_6)$alkanoyl, α-amino $(C_1-C_4)$alkanyl, arylacyl and α-aminoacyl, or α-aminoacyl-α-aminoacyl, where each α-aminoacyl group is independently selected from the naturally occurring L-amino acids, $P(O)(OH)_2$, —$P(O)(O(C_1-C_6)alkyl)_2$ or glycosyl (the radical resulting from the removal of a hydroxyl group of the hemiacetal form of a carbohydrate), and the like.

If a compound of Formula (I) incorporates an amine functional group, a prodrug can be formed by the replacement of a hydrogen atom in the amine group with a group such as, for example, R-carbonyl, RO-carbonyl, NRR'-carbonyl where R and R' are each independently $(C_1-C_{10})$alkyl, $(C_3-C_7)$ cycloalkyl, benzyl, or R-carbonyl is a natural α-aminoacyl or natural α-aminoacyl, —C(OH)C(O)O$Y^1$ wherein $Y^1$ is H, $(C_1-C_6)$alkyl or benzyl, —C(O$Y^2$)$Y^3$ wherein $Y^2$ is $(C_1-C_4)$ alkyl and $Y^3$ is $(C_1-C_6)$alkyl, carboxy $(C_1-C_6)$alkyl, amino $(C_1-C_4)$alkyl or mono-N— or di-N,N—$(C_1-C_6)$alkylaminoalkyl, —C($Y^4$)$Y^5$ wherein $Y^4$ is H or methyl and $Y^5$ is mono-N— or di-N,N—$(C_1-C_6)$alkylamino morpholino, piperidin-1-yl or pyrrolidin-1-yl, and the like.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

One or more compounds of the invention may optionally be converted to a solvate. Preparation of solvates is generally known. Thus, for example, M. Caira at al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder at al, *AAPS PharmSciTech.*, 5(1), article 12 (2004); and A. L. Bingham at al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

"Effective amount" or "therapeutically effective amount" is meant to describe an amount of compound or a composition of the present invention effective in inhibiting the above-noted diseases and thus producing the desired therapeutic, ameliorative, inhibitory or preventative effect.

The compounds of Formula (I) can form salts which are also within the scope of this invention. Reference to a compound of Formula (I) herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula (I) may be formed, for example, by reacting a compound of Formula (I) with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use.* (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the present compounds include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di ($C_{6-24}$)acyl glycerol.

Compounds of formula (I), and salts, solvates, esters and prodrugs thereof, may exist in their tautomeric form (for example, as an amide, enol, keto or imino ether). All such tautomeric forms are contemplated herein as part of the present invention.

The compounds of formula (I) may contain asymmetric or chiral centers, and, therefore, exist in different stereoisomeric forms. It is intended that all stereoisomeric forms of the compounds of formula (I) as well as mixtures thereof, including racemic mixtures, form part of the present invention. In addition, the present invention embraces all geometric and positional isomers. For example, if a compound of formula (I) incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of formula (I) may be atropisomers (e.g., substituted biaryls) and are considered as part of this invention. Enantiomers can also be separated by use of chiral HPLC column.

It is also possible that the compounds of formula (I) may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl), (For example, if a compound of formula (I) incorporates a double bond or a fused ring, both the cis- and trans-forms, as well as mixtures, are embraced within the scope of the invention. Also, for example, all keto-enol and imine-enamine forms of the compounds are included in the invention.) Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

Certain isotopically-labelled compounds of formula (I) (e.g., those labeled with $^3$H and $^{14}$C) are useful in compound and/or substrate tissue distribution assays. Tritiated (i.e., $^3$H) and carbon-14 (i.e., $^{14}$C) isotopes are particularly preferred for their ease of preparation and detectability. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Isotopically labelled compounds of formula (I) can generally be prepared by following procedures analogous to those disclosed in the Schemes and/or in the Examples hereinbelow, by substituting an appropriate isotopically labelled reagent for a non-isotopically labelled reagent.

Polymorphic forms of the compounds of formula (I), and of the salts, solvates, esters and prodrugs of the compounds of formula (I), are intended to be included in the present invention.

The compounds according to the invention can have pharmacological properties; in particular, the compounds of formula (I) can be modulators of gamma secretase (including inhibitors, antagonists and the like).

More specifically, the compounds of formula (I) can be useful in the treatment of a variety of disorders of the central nervous system including, for example, including, but not limited to, Alzheimer's disease, AIDS-related dementia, Parkinson's disease, amyotrophic lateral sclerosis, retinitis pigmentosa, spinal muscular atrophy and cerebellar degeneration and the like.

Another aspect of this invention is a method of treating a mammal (e.g., human) having a disease or condition of the central nervous system by administering a therapeutically effective amount of at least one compound of formula (I), or a pharmaceutically acceptable salt, solvate, ester or prodrug of said compound to the mammal.

A preferred dosage is about 0.001 to 500 mg/kg of body weight/day of the compound of formula (I). An especially preferred dosage is about 0.01 to 25 mg/kg of body weight/day of a compound of formula (I), or a pharmaceutically acceptable salt or solvate of said compound.

The compounds of this invention may also be useful in combination (administered together or sequentially) with one or more additional agents listed above.

The compounds of this invention may also be useful in combination (administered together or sequentially) with one or more compounds selected from the group consisting of Aβ antibody inhibitors, gamma secretase inhibitors and beta secretase inhibitors.

If formulated as a fixed dose, such combination products employ the compounds of this invention within the dosage range described herein and the other pharmaceutically active agent or treatment within its dosage range.

Accordingly, in an aspect, this invention includes combinations comprising an amount of at least one compound of formula (I), or a pharmaceutically acceptable salt, solvate, ester or prodrug thereof, and an amount of one or more additional agents listed above wherein the amounts of the compounds/treatments result in desired therapeutic effect.

The pharmacological properties of the compounds of this invention may be confirmed by a number of pharmacological assays. Certain assays are exemplified later in this document.

This invention is also directed to pharmaceutical compositions which comprise at least one compound of formula (I), or a pharmaceutically acceptable salt, solvate, ester or prodrug of said compound and at least one pharmaceutically acceptable carrier.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose, Tablets, powders, cachets and capsules can be used as solid dosage forms suitable for oral administration. Examples of pharmaceutically acceptable carriers and methods of manufacture for various compositions may be found in A. Gennaro (ed.), *Remington's Pharmaceutical Sciences*, 18$^{th}$ Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

The compounds of this invention may also be delivered subcutaneously.

Preferably the compound is administered orally.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 1 mg to about 100 mg, preferably from about 1 mg to about 50 mg, more preferably from about 1 mg to about 25 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 1 mg/day to about 500 mg/day, preferably 1 mg/day to 200 mg/day, in two to four divided doses.

Another aspect of this invention is a kit comprising a therapeutically effective amount of at least one compound of formula (I), or a pharmaceutically acceptable salt, solvate, ester or prodrug of said compound and a pharmaceutically acceptable carrier, vehicle or diluent.

Yet another aspect of this invention is a kit comprising an amount of at least one compound of formula (I), or a pharmaceutically acceptable salt, solvate, ester or prodrug of said compound and an amount of at least one additional agent listed above, wherein the amounts of the two or more ingredients result in desired therapeutic effect.

The invention disclosed herein is exemplified by the following illustrative schemes and examples which should not be construed to limit the scope of the disclosure. Alternative mechanistic pathways and analogous structures will be apparent to those skilled in the art.

The compounds of the invention can be prepared by the schemes and examples below. Compounds of the invention wherein $G^5$ moiety is bound to $G^3$ (i.e., position (2)) can be prepared by the same chemistry unless indicated otherwise.

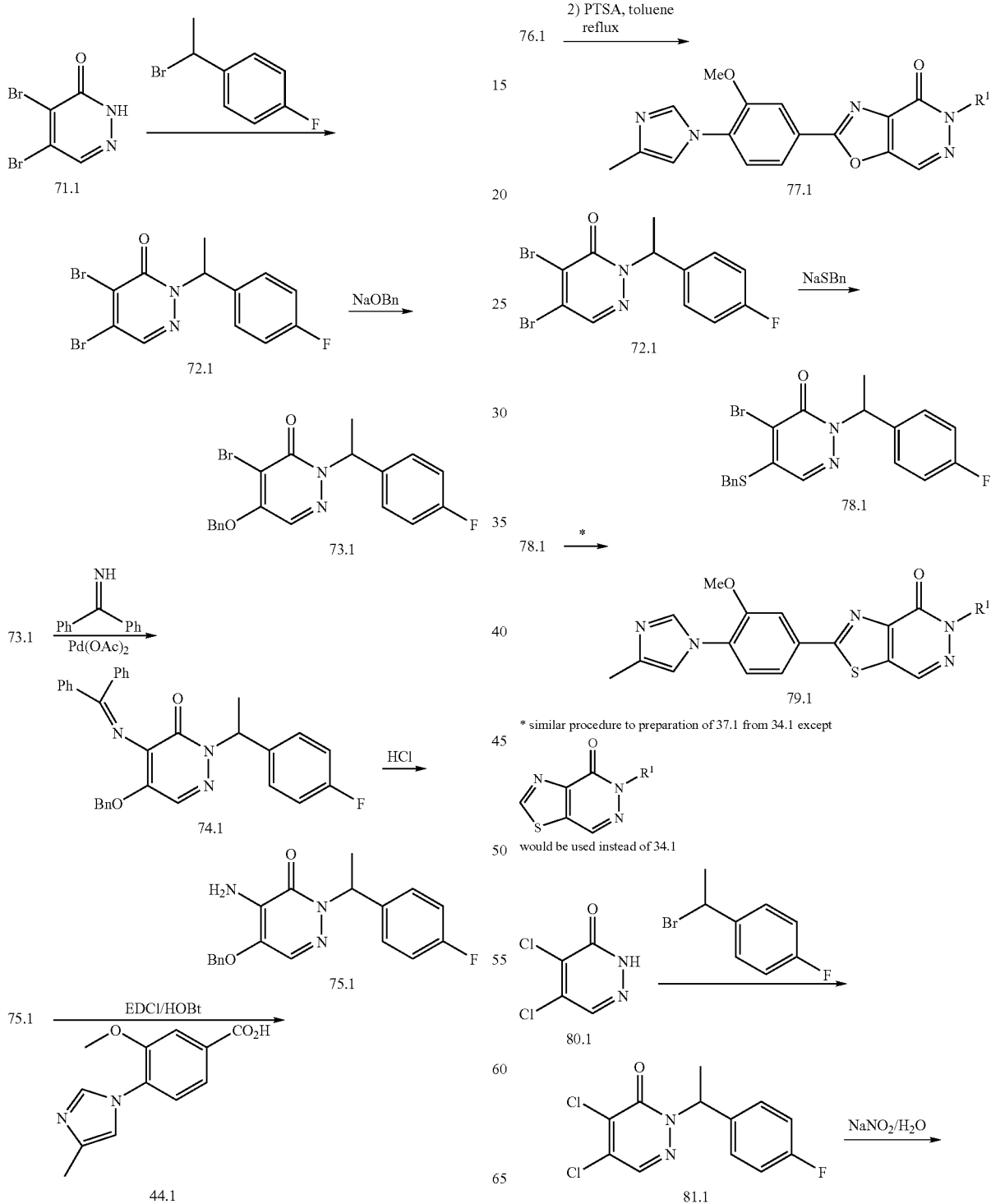

129
-continued
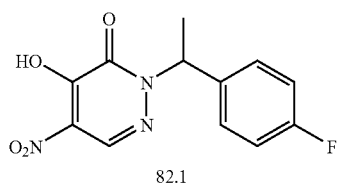
82.1
Gagnier, R. Paul; Halat, Michael J.; Otter, Brian A.; JHTCAD; J. Heterocycl. Chem.; EN; 21; 1984; 481-489.
82.1 →  1) NH₃;  2) H₂/Pd(C)
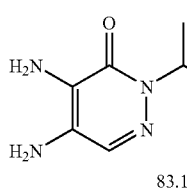
83.1
83.1 →  EDCl/HOBt
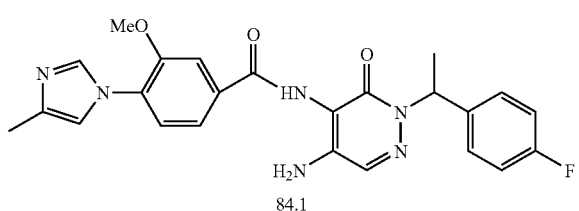
44.1
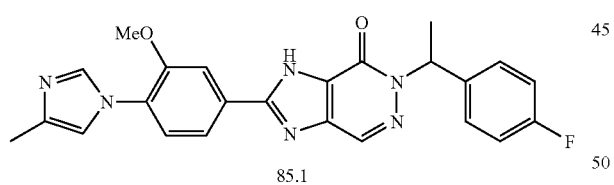
84.1
84.1 →  PTSA, toluene reflux
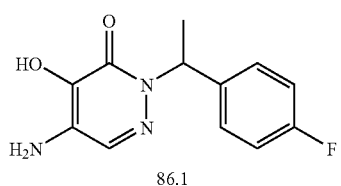
85.1
82.1 →  H₂/Pd(C)
86.1
130
-continued
86.1 →  EDCl/HOBt
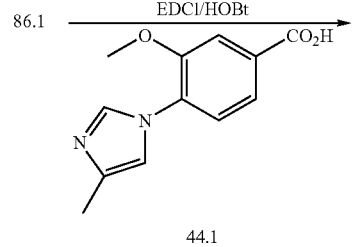
44.1
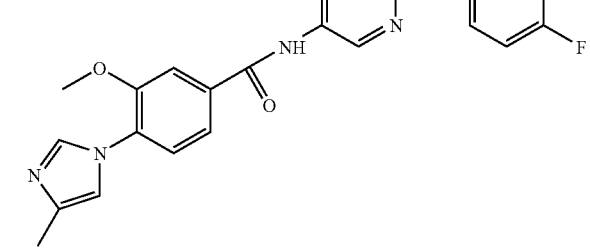
87.1
87.1 →  PTSA, toluene reflux
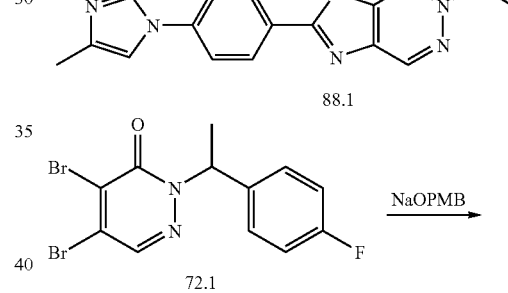
88.1
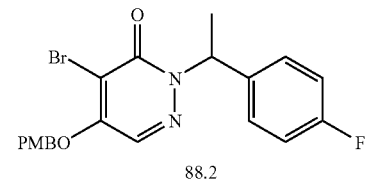
72.1  →  NaOPMB
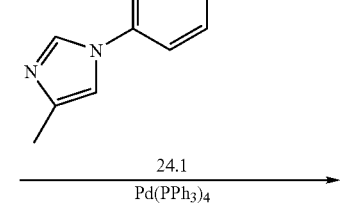
88.2
88.2 →  Bu₃SnSnBu₃/Pd(PPh₃)₄
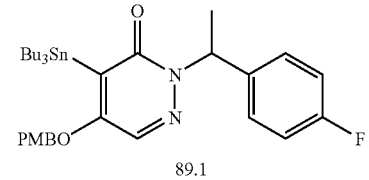
89.1
89.1 →  24.1 / Pd(PPh₃)₄

131
-continued
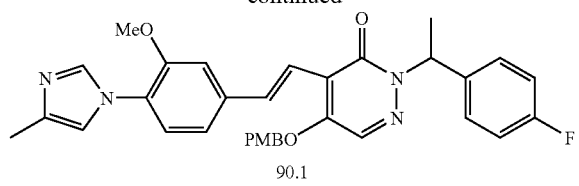
90.1
1) CAN
2) HClO₄
90.1 →
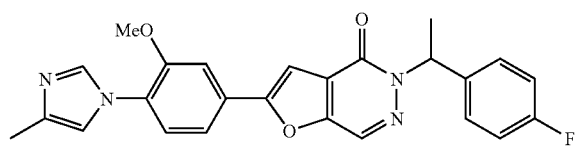
91.1
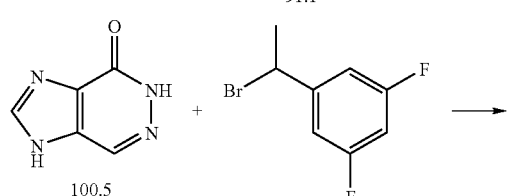
100.5
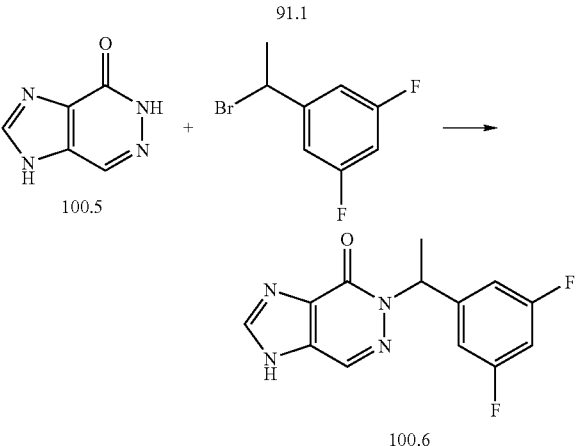
100.6
NBS
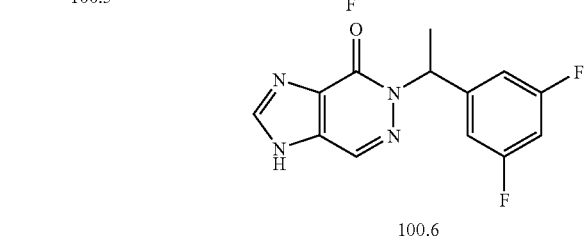
100.7
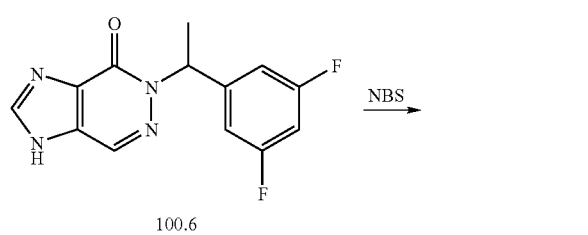
100.7
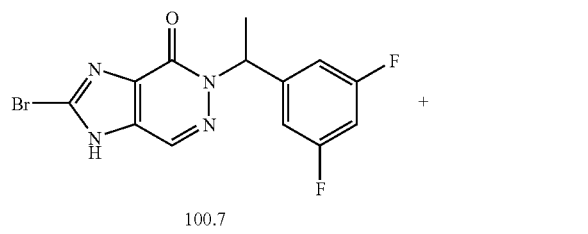
100.4
Pd(PPh₃)₄ →
132
-continued
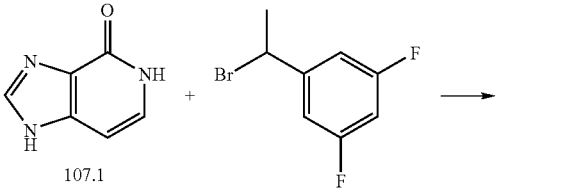
100
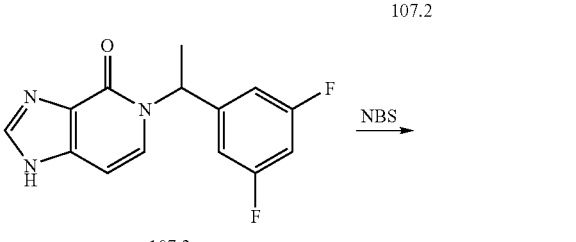
107.1
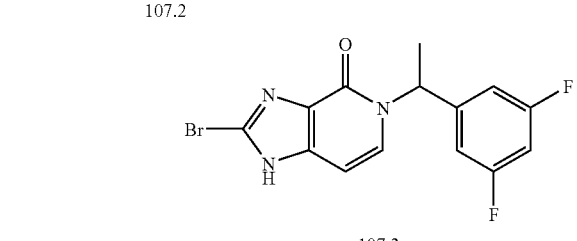
107.2
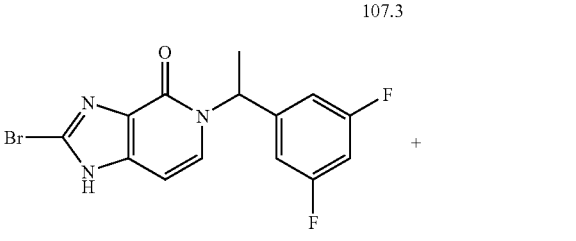
107.2
NBS
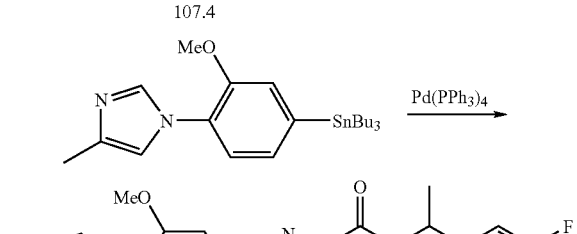
107.3
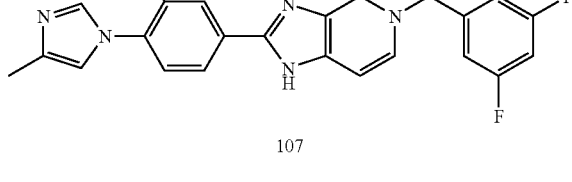
107.4
+
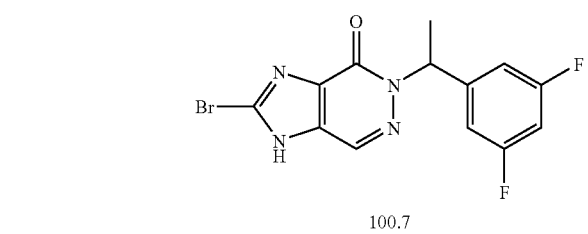
Pd(PPh₃)₄ →
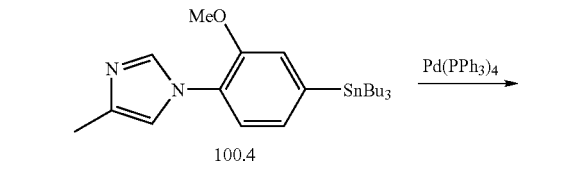
107

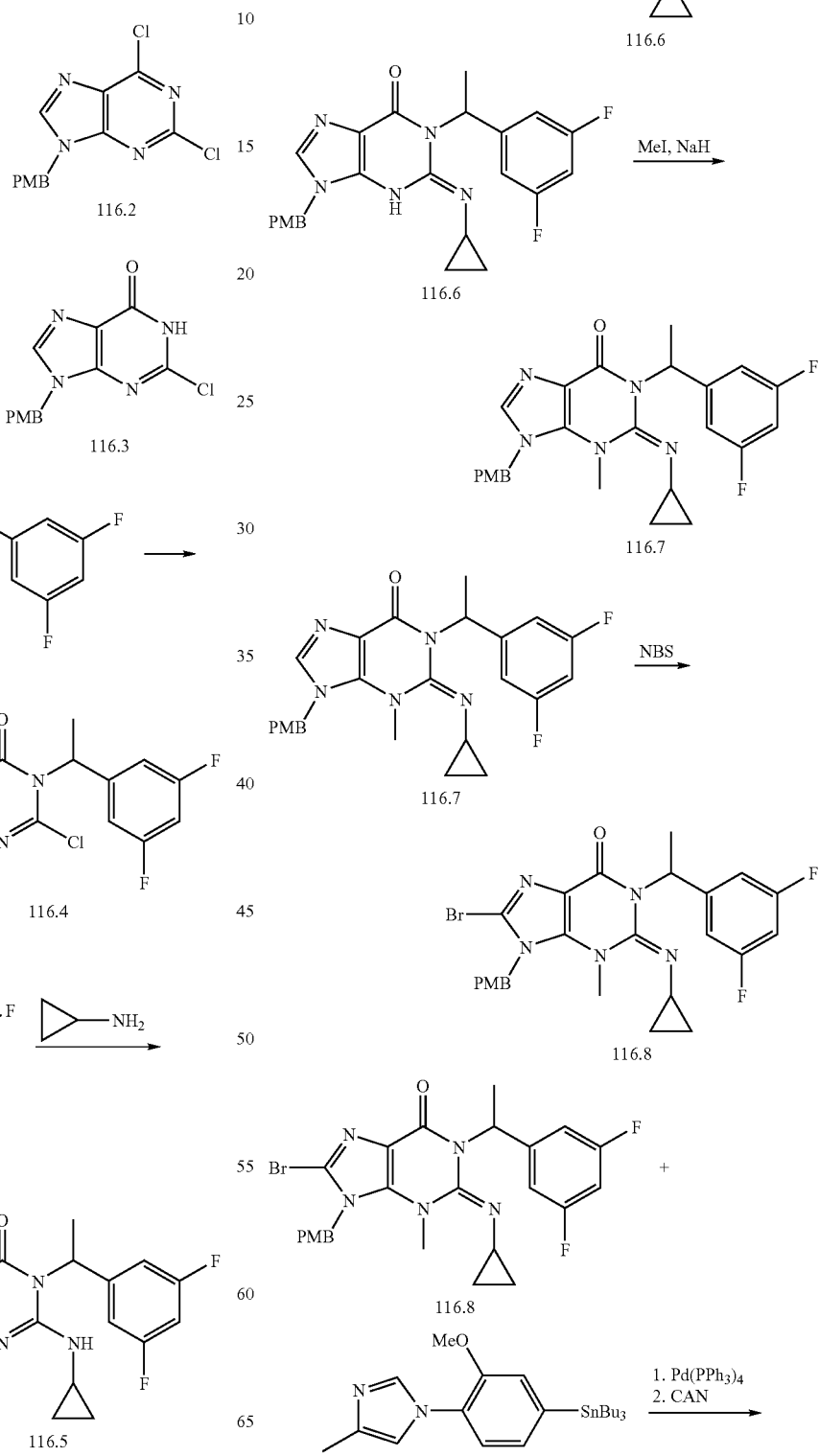

-continued

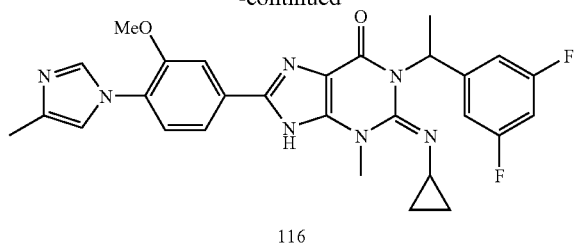

116

Example 1

100

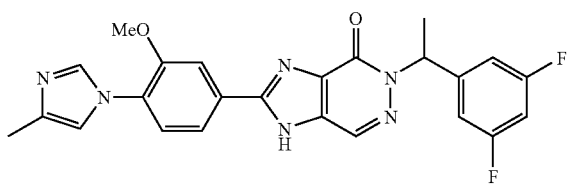

Step A:

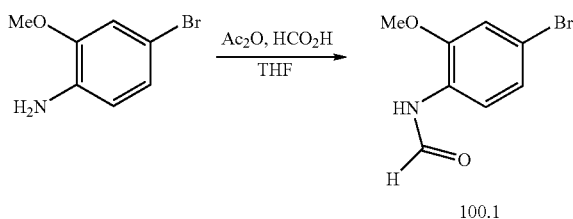

To a round bottom flask at room temperature. containing formic acid (85%, 27 mL, 624.4 mmol) was added acetic anhydride (16 mL, 169.5 mmol) dropwise. The reaction stirred for 45 min. followed by the dropwise addition of a solution of 4-bromo-2-methoxyaniline (9.01 g, 44.6 mmol) in THF (56 mL). The reaction mixture was quenched with ice-water after 23 h and the resulting precipitate was filtered to afford compound 100.1 (9.20 g, 90%) as a brown solid.

Step B:

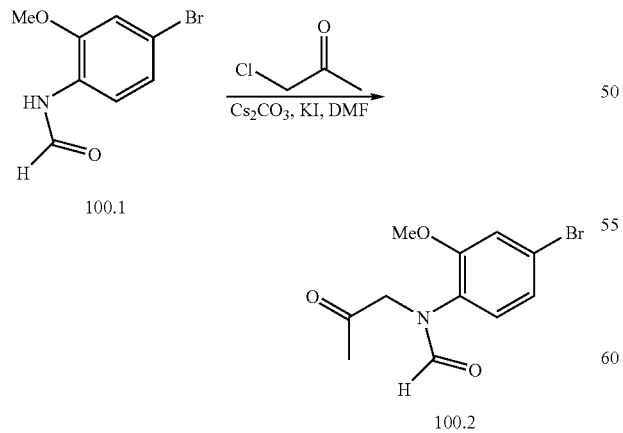

To a round bottom flask at room temperature containing a mixture of compound 100.1 (9.20 g, 39.9 mmol), cesium carbonate (26.05 g, 79.9 mmol), and potassium iodide (0.66 g, 3.9 mmol) in DMF (40 mL) was added chloroacetone (6.7 mL, 79.9 mmol) dropwise. The reaction stirred for 3 h followed by addition of cesium carbonate (13.02 g, 39.9 mmol) and chloroacetone (3.35 mL, 39.9 mmol). After 19 h the reaction was diluted with water, extracted with 75% ethyl acetate/hexanes, washed with brine, dried over $Na_2SO_4$, and concentrated in vacuo. The crude material was purified by silica gel chromatography with ethyl acetate/dichloromethane to afford compound 100.2 (10.94 g, 96%) as a beige solid.

Step C:

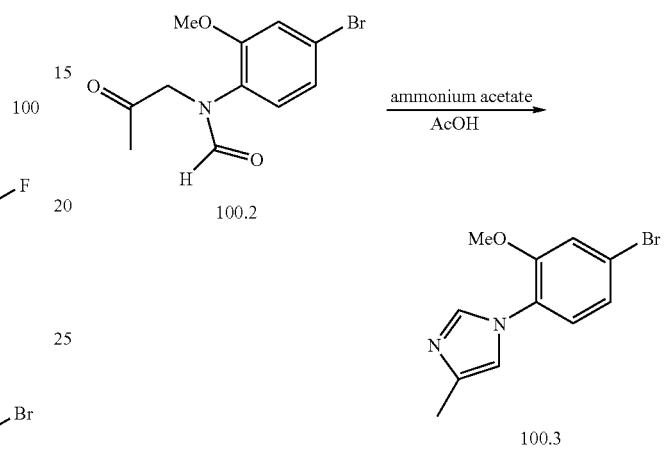

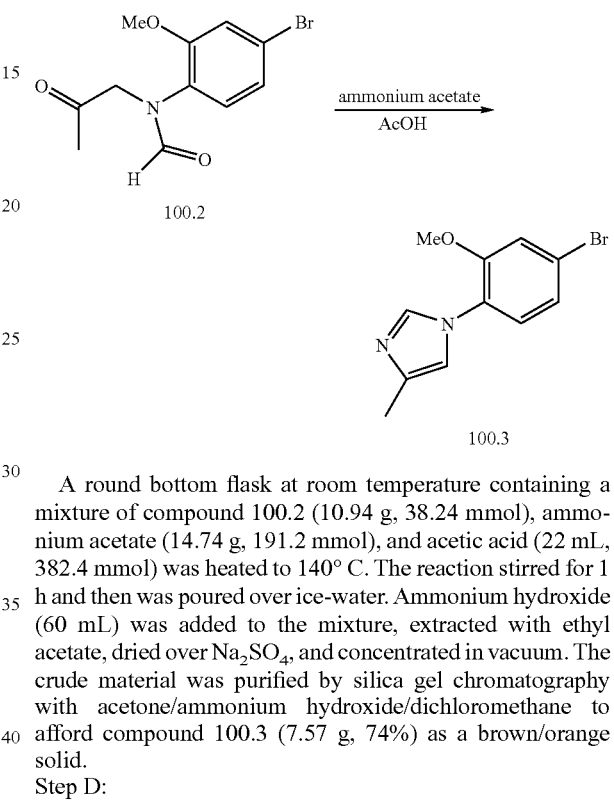

A round bottom flask at room temperature containing a mixture of compound 100.2 (10.94 g, 38.24 mmol), ammonium acetate (14.74 g, 191.2 mmol), and acetic acid (22 mL, 382.4 mmol) was heated to 140° C. The reaction stirred for 1 h and then was poured over ice-water. Ammonium hydroxide (60 mL) was added to the mixture, extracted with ethyl acetate, dried over $Na_2SO_4$, and concentrated in vacuum. The crude material was purified by silica gel chromatography with acetone/ammonium hydroxide/dichloromethane to afford compound 100.3 (7.57 g, 74%) as a brown/orange solid.

Step D:

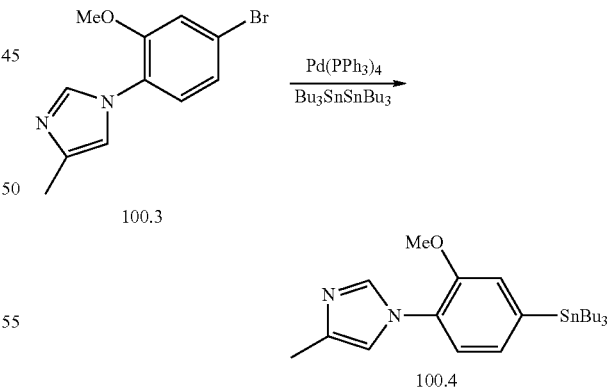

To compound 100.3 (1.4 mmol), $Bu_3SnSnBu_3$ (2.1 mmol) and Potassium carbonate (7 mmol) was added 30 ml Toluene followed by $Pd(PPh_3)_4$ (0.14 mmol) then heat to 120° C. for 2 hrs. The reaction was worked up by cooling to room temperature then adding water and dichloromethane. Extract aqueous layer 3× dichloromethane, then dry over sodium sulfate and filter and concentrate to dryess. The residue was purified by chromatography over silica gel (eluted with dichloromethane/MeOH 99:1 to 90:10) to provide product 100.4.

Step E:

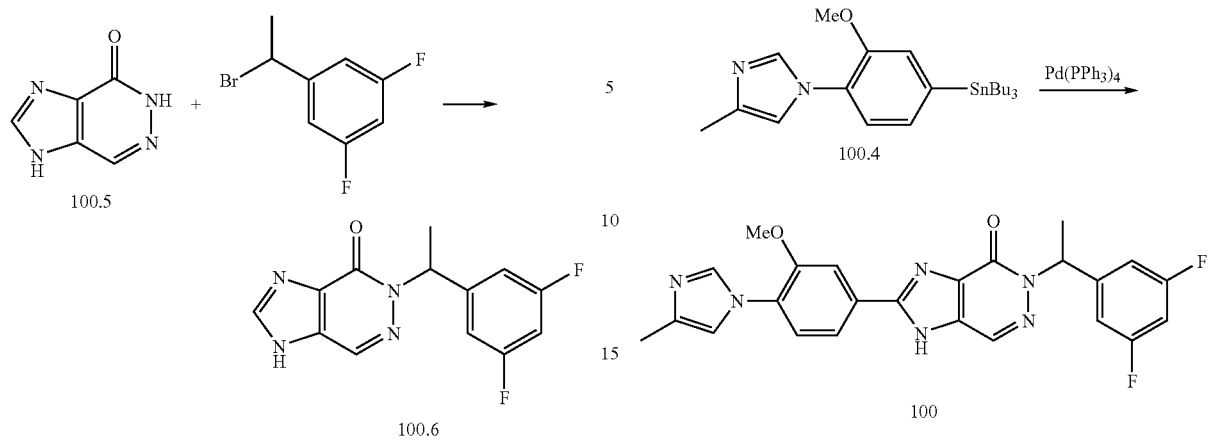

To compound 100.5 (1.0 mmol), alpha-methyl 3.5 difluorobenzyl bromide (1.5 mmol) and Potassium carbonate (5.0 mmol) will be added 30 mL. DMF. The mixture will be stirred at room temperature overnight. The reaction will be worked up by adding water and EtOAc. Extract aqueous layer 3×EtOAc, then dry over sodium sulfate and filter and concentrate to dryess. The residue will be purified by chromatography over silica gel to provide product 100.6.

Step F:

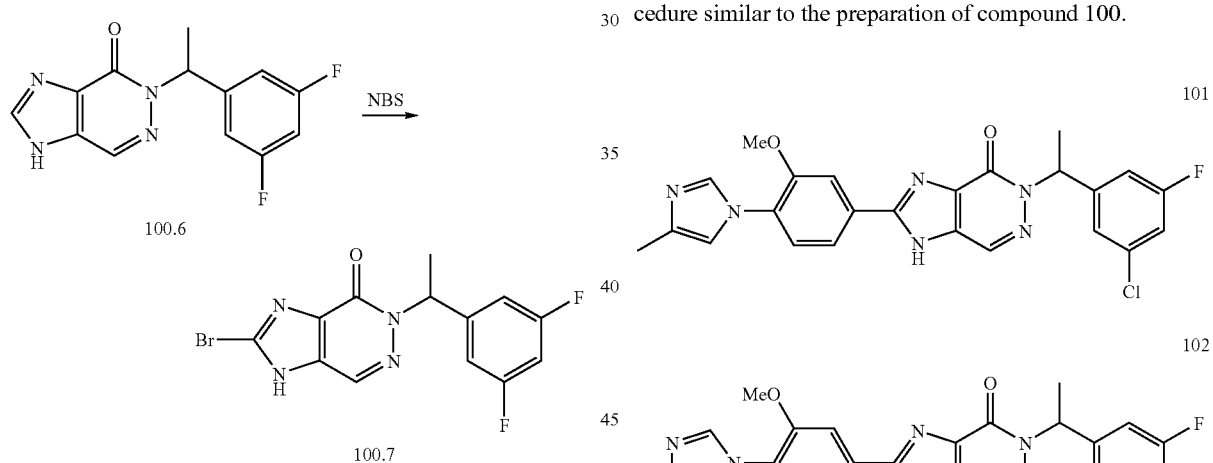

To compound 100.6 (1.0 mmol) in DMF (6.0 mL) will be added N-bromosuccinimide (1.1 mmol) at room temperature. The mixture will be stirred at room temperature overnight. The reaction will be worked up by adding aqueous $Na_2S_2O_3$ and EtOAc. Extract aqueous layer 3×EtOAc, then dry over sodium sulfate and filter and concentrate to dryess. The residue will be purified by chromatography over silica gel to provide product 100.7.

Step G:

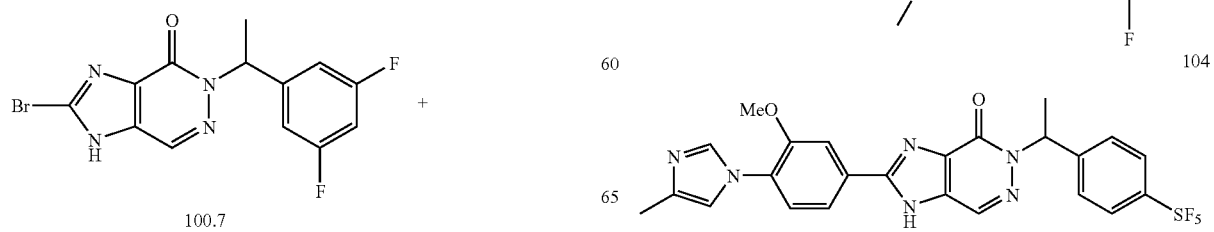

To compound 100.7 (1.4 mmol), 100.4 (2.1 mmol) and Potassium carbonate (7 mmol) will be added 30 mL Toluene followed by $Pd(PPh_3)_4$ (0.14 mmol) then heat to 120° C. for 2 hrs. The reaction will be worked up by cooling to RT then adding water and dichloromethane. Extract aqueous layer 3× dichloromethane, then dry over sodium sulfate and filter and concentrate to dryess. The residue will be purified by chromatography over silica gel to provide product 100.

Compounds 101 to 124 will be prepared following a procedure similar to the preparation of compound 100.

-continued
105
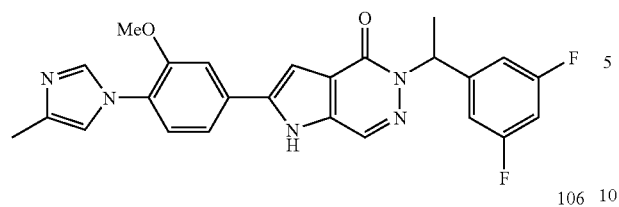
106
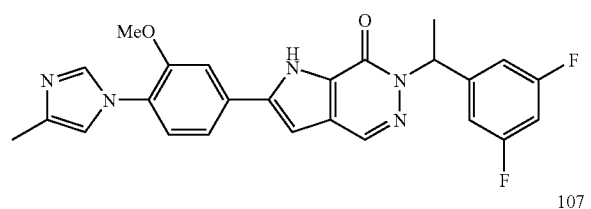
107
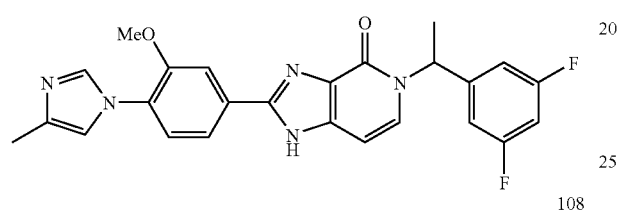
108
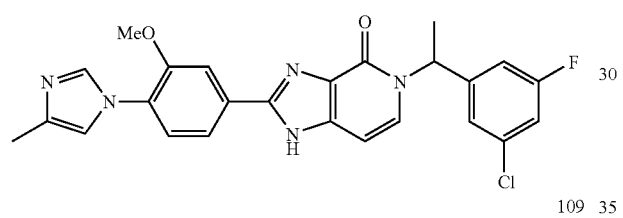
109
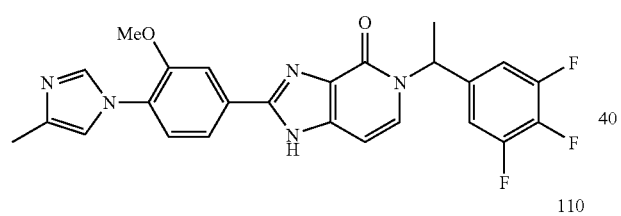
110
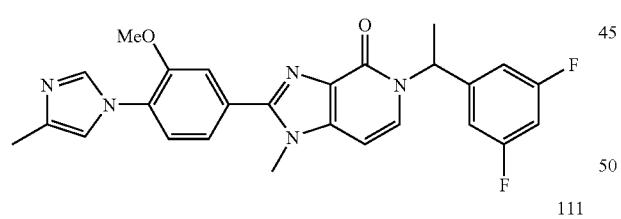
111
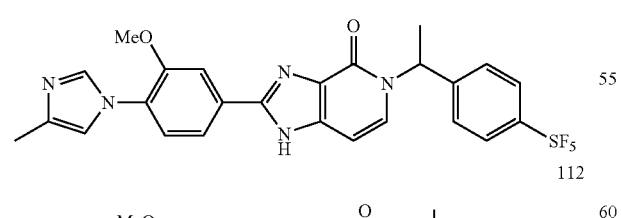
112
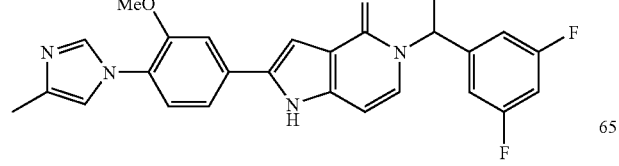
-continued
113
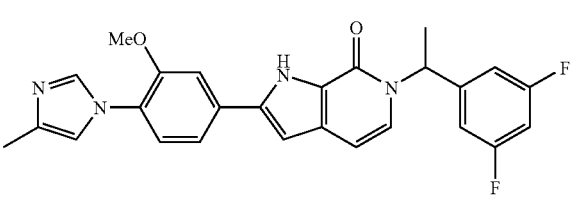
114
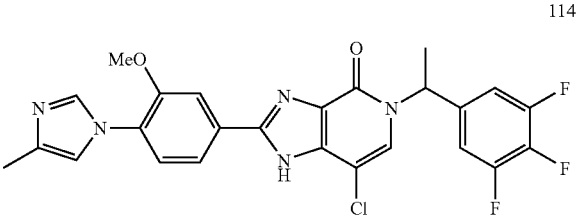 [SMILES: COc1cc(-c2nc3c(=O)n(C(C)c4cc(F)cc(F)c4)ncc3[nH]2)ccc1-n1cnc(C)c1]
115
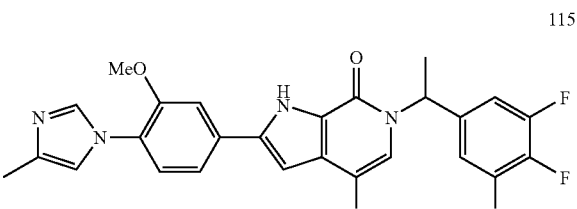
116
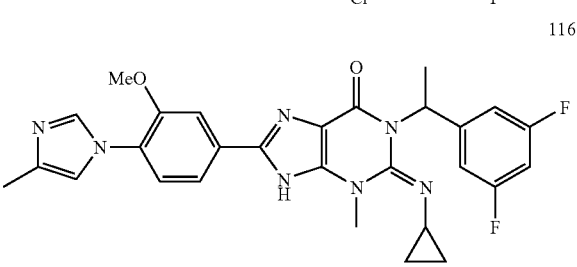
117
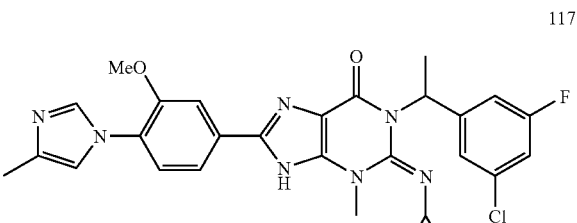
118
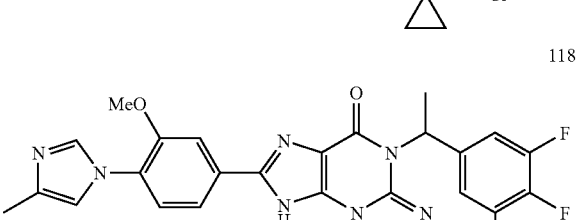
119
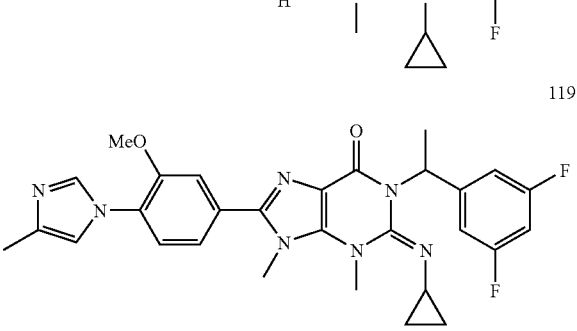

-continued

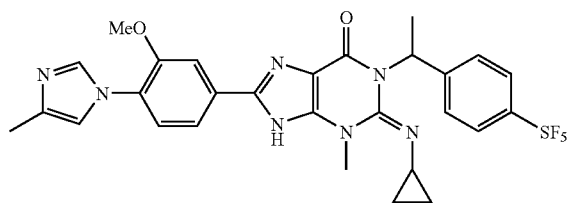

120

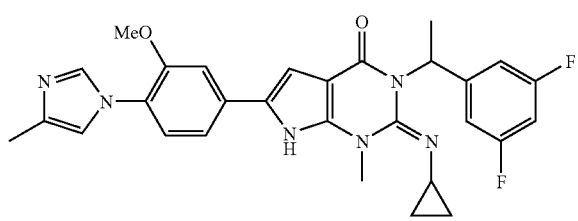

121

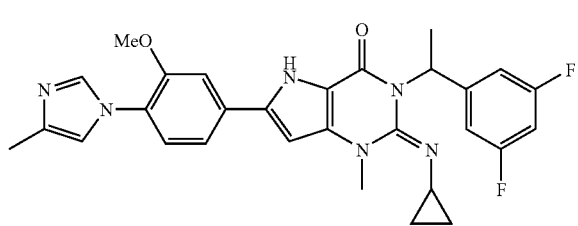

122

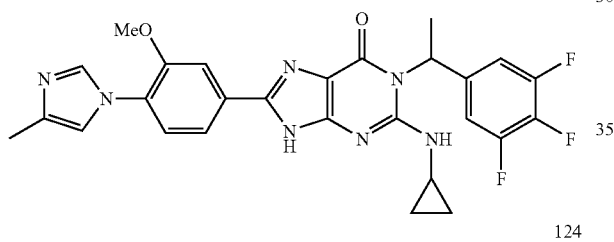

123

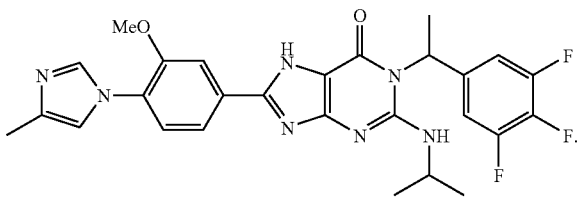

124

Assay:

Secretase Reaction and Aβ Analysis in Whole Cells: HEK293 cells overexpressing APP with Swedish and London mutations is treated with the specified compounds for 5 hour at 37° C. in 100 ml of DMEM medium containing 10% fetal bovine serum. At the end of the incubation, total Aβ, Aβ40 and Aβ42 is measured using electrochemiluminescence (ECL) based sandwich immunoassays. Total Aβ is determined using a pair of antibodies TAG-W02 and biotin-4G8, Aβ40 is identified with antibody pairs TAG-G2-10 and biotin-4G8, while Aβ42 is identified with TAG-G2-11 and biotin-4G8. The ECL signal is measured using Sector Imager 2400 (Meso Scale Discovery).

MS Analysis of Aβ Profile: Aβ profile in conditioned media is determined using surface enhanced laser desorption/ionization (SELDI) mass spectrometry. Conditioned media is incubated with antibody W02 coated PS20 ProteinChip array. Mass spectra of Aβ captured on the array is read on SELDI ProteinChip Reader (Bio-Rad) according to manufacturer's instructions.

CSF Aβ Analysis: Aβ in rat CSF is determined using MSD technology as described above. Aβ40 is measured using antibody pair Tag-G2-10 and biotin-4G8, while Aβ42 is measured using Tag-anti Aβ42 (Meso Scale Discovery) and biotin-4G8. The ECL signal is measured using Sector Imager 2400 (Meso Scale Discovery).

Matrix-assisted laser desorption/ionization mass spectrometric (MALDI MS) analysis of Aβ is performed on a Voyager-DE STR mass spectrometer (ABI, Framingham, Mass.). The instrument is equipped with a pulsed nitrogen laser (337 nm). Mass spectra is acquired in the linear mode with an acceleration voltage of 20 kV. Each spectrum presented in this work represents an average of 256 laser shots. To prepare the sample-matrix solution, 1 μL of immunoprecipitated Aβ sample is mixed with 3 μL of saturated α-cyano-4-hydroxycinnamic acid solution in 0.1% TFA/acetonitrile. The sample-matrix solution is then applied to the sample plate and dried at ambient temperature prior to mass spectrometric analysis. All the spectra are externally calibrated with a mixture of bovine insulin and ACTH (18-39 clip).

While the present invention has been described in conjunction with the specific embodiments set forth above, many alternatives, modifications and other variations thereof will be apparent to those of ordinary skill in the art. All such alternatives, modifications and variations are intended to fall within the spirit and scope of the present invention.

What is claimed is:

1. A compound of the formula:

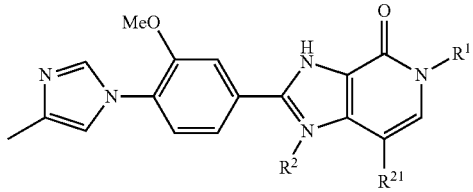

or a pharmaceutically acceptable salt thereof,
wherein $R^1$ is an alkyl group substituted with one phenyl, wherein the phenyl is optionally substituted with 1-3 halo or one $SF_5$ group;
$R^2$ is hydrogen or alkyl; and
$R^{21}$ is hydrogen or halo.

2. The compound according to claim 1 or a pharmaceutically acceptable salt thereof, wherein the alkyl group of $R^1$ is methyl or ethyl.

3. The compound according to claim 1 or a pharmaceutically acceptable salt thereof, wherein the phenyl of $R^1$ is substituted with 1-3 fluoro.

4. The compound according to claim 1 or a pharmaceutically acceptable salt thereof, wherein $R^2$ is methyl.

5. The compound according to claim 1 or a pharmaceutically acceptable salt thereof, wherein $R^{21}$ is chloro.

6. The compound according to claim 1 or a pharmaceutically acceptable salt thereof, wherein the compound is selected from the group consisting of:

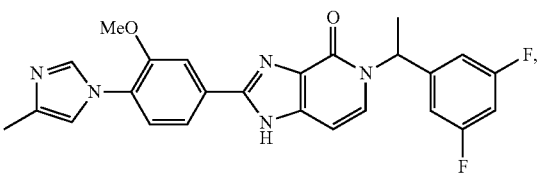

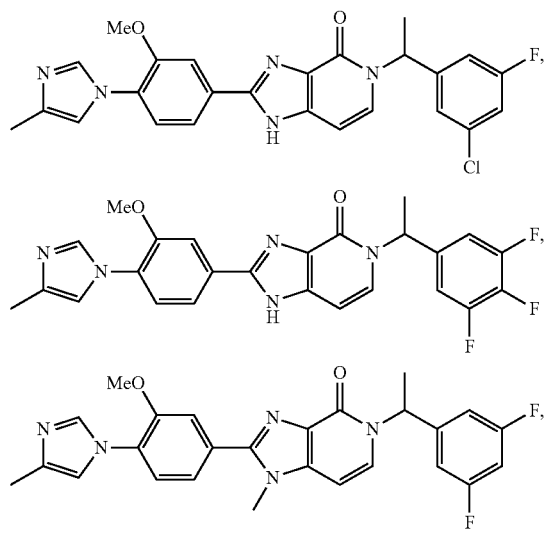

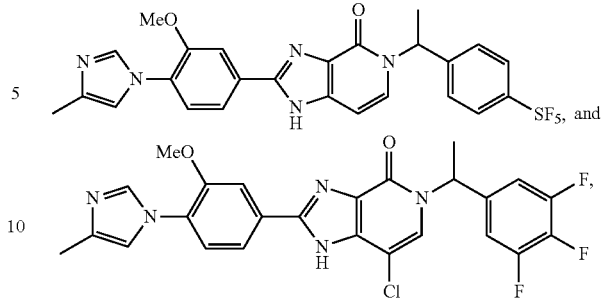

or a pharmaceutically acceptable salt thereof.

7. A pharmaceutical composition comprising a compound according to claim 1 or a pharmaceutically acceptable salt thereof and a pharmaceutically acceptable carrier.

8. A pharmaceutical composition comprising a compound according to claim 6 or a pharmaceutically acceptable salt thereof and a pharmaceutically acceptable carrier.

* * * * *

UNITED STATES PATENT AND TRADEMARK OFFICE
CERTIFICATE OF CORRECTION

| | | |
|---|---|---|
| PATENT NO. | : 8,426,595 B2 | Page 1 of 1 |
| APPLICATION NO. | : 12/747011 | |
| DATED | : April 23, 2013 | |
| INVENTOR(S) | : Huang et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 262 days.

Signed and Sealed this
Fourth Day of November, 2014

Michelle K. Lee
*Deputy Director of the United States Patent and Trademark Office*